US010539552B2

(12) United States Patent
Chen-Izu et al.

(10) Patent No.: US 10,539,552 B2
(45) Date of Patent: Jan. 21, 2020

(54) COMPOSITIONS AND METHODS FOR MEASURING CELLULAR MECHANICAL STRESS

(71) Applicant: The Regents of the University of California, Oakland, CA (US)

(72) Inventors: Ye Chen-Izu, Davis, CA (US); Kit Lam, Davis, CA (US); Leighton T. Izu, Davis, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 174 days.

(21) Appl. No.: 15/121,733

(22) PCT Filed: Mar. 4, 2015

(86) PCT No.: PCT/US2015/018705
§ 371 (c)(1),
(2) Date: Aug. 25, 2016

(87) PCT Pub. No.: WO2015/134589
PCT Pub. Date: Sep. 11, 2015

(65) Prior Publication Data
US 2017/0016885 A1 Jan. 19, 2017

Related U.S. Application Data

(60) Provisional application No. 61/949,049, filed on Mar. 6, 2014.

(51) Int. Cl.
| | | |
|---|---|---|
| *G01N 33/50* | (2006.01) | |
| *G01N 33/543* | (2006.01) | |
| *C08J 3/075* | (2006.01) | |
| *C12M 1/00* | (2006.01) | |
| *C12M 1/42* | (2006.01) | |
| *C12M 1/34* | (2006.01) | |
| *G01N 33/545* | (2006.01) | |

(52) U.S. Cl.
CPC .......... *G01N 33/5061* (2013.01); *C08J 3/075* (2013.01); *C12M 29/10* (2013.01); *C12M 35/02* (2013.01); *C12M 35/04* (2013.01); *C12M 41/46* (2013.01); *G01N 33/502* (2013.01); *G01N 33/545* (2013.01); *G01N 33/5436* (2013.01); *G01N 33/54366* (2013.01); *C08J 2329/04* (2013.01)

(58) Field of Classification Search
CPC ............ C07K 2319/21; C07K 2319/22; C07K 2319/23; C07K 2319/24
See application file for complete search history.

(56) References Cited

U.S. PATENT DOCUMENTS

| | | | |
|---|---|---|---|
| 5,698,405 | A | 12/1997 | Goldenberg |
| 2008/0268514 | A1 | 10/2008 | Muller et al. |
| 2009/0130755 | A1 | 5/2009 | Detamore et al. |
| 2013/0196915 | A1 | 8/2013 | Wang et al. |
| 2013/0224881 | A1 | 8/2013 | Thompson et al. |

FOREIGN PATENT DOCUMENTS

| | | |
|---|---|---|
| CN | 101298592 A | 11/2008 |
| CN | 102505184 A | 6/2012 |
| CN | 102977362 A | 3/2013 |
| CN | 103249433 A | 8/2013 |
| WO | 2003000234 A1 | 1/2003 |
| WO | 2010/106347 | 9/2010 |
| WO | 2010/148346 | 12/2010 |
| WO | 2012047582 A2 | 4/2012 |

OTHER PUBLICATIONS

Definition of "via" downloaded from https://www.merriam-webster.com/dictionary/via on Nov. 30, 2018 (Year: 2018).*
Definition of "kit" downloaded from https://www.thefreedictionary.com/kit on Dec. 4, 2018 (Year: 2018).*
Cheng et al. Biomacromolecules (Jan. 11, 2013) 14: 468-475 (Year: 2013).*
Clapper et al. Biomacromolecules (2008) 9: 1188-1194 (Year: 2008).*
Shu et al. J. Biomed. Materials Research (2004) 68(A): 365-375. (Year: 2004).*
Tan et al. Macromol. Rapid Comm. (2012) 33: 2015-2022, full paper (Year: 2012).*
WO patent application No. PCT/US15/18705, International Search Report and Written Opinion dated Jul. 31, 2015.
WO patent application No. PCT/US15/18705, International Preliminary Report on Patentability dated Sep. 15, 2016.
Chen-Izu, Ye et al., "Hypertension-induced remodeling of cardiac excitation-contraction coupling in ventricular myocytes occurs prior to hypertrophy development," *Am J Physiol Heart Circ Physiol* 293: H3301-H3310, 2007.
Creative Pegworks, Homobifunctional PEG Reagents—X-PEG-X [online] 2013, http://www.creativepegworks.com/bifunctional_PEG.html>.
Donaldson, Olivia et al., "An integrated experimental and modeling approach to propose biotinylated PLGA microparticles as versatile targeting vehicles for drug delivery," *Progress in Biomaterials* 2013, 2:3.
Fahmy, Tarek M. et al., "Surface modification of biodegradable polyesters with fatty acid conjugates for improved drug targeting," *Biomaterials* 26 (2005) 5727-5736.
Fernandez, Pablo et al., "The compaction of gels by cells: a case of collective mechanical activity," *Integr. Biol.*, 2009, 1, 252-259.
Gilbert, Yann et al., "Single-molecule force spectroscopy and imaging of the Vancomycin/D-Ala-D-Ala interaction," *Nano Letters* 2007, vol. 7, No. 3 796-801.

(Continued)

*Primary Examiner* — Susan M Hanley
(74) *Attorney, Agent, or Firm* — Mintz, Levin, Cohn, Ferris, Glovsky & Popeo, P.C.

(57) ABSTRACT

Provided are compositions and methods employing cells encapsulated within and attached to a hydrogel, e.g., for measuring mechanical strain and/or stress of the cell and for investigating the mechano-chemo-transduction mechanisms at cellular and molecular levels.

13 Claims, 25 Drawing Sheets

(56) References Cited

OTHER PUBLICATIONS

Izu, Leighton T. et al., "Mechanical signals to the $Ca^{2+}$ control system," presented at the 2013 Cardiac Physiome Workshop, Bar Harbor, ME, Oct. 17-19, 2013.

Jian, Zhong et al., "Mechanochemotransduction during cardiomyocyte contraction is mediated by localized nitric oxide signaling," *Sci Signal.*; 7(317): ra27. doi:10.1126/scisignal.2005046.

Kirk, Malcolm M. et al., "Role of the transverse-axial tubule system in generating calcium sparks and calcium transients in rat atrial myocytes," *J Physiol* (2003), 547.2 pp. 441-451.

Klumpers, Darinka D. et al., "Cell mediated contraction in 3D cell-matrix constructs leads to spatially regulated osteogenic differentiation," *Integr. Biol.* 2013, 5, 1174.

Liu, Yingkai et al., "Biodegradable PEG hydrogels cross-linked using Biotin-Avidin interactions," *Aust. J. Chem.* 2010, 63, 1413-1417.

McGuigan, Alison P. et al., "Cell encapsulation in sub-mm sized gel modules using replica molding," PLoS ONE 3(5): e2258 doi:10.1371/journal.pone.0002258.

Okamoto, Y. et al., "Separation of cationic polymer particles and characterization of avidin-immobilized particles by capillary electrophoresis," *Electrophoresis*, Mar. 2006; 27(5-6):1031-40, PubMed abstract 16470774.

Petroff, Martin G. et al., "Endogenous nitric oxide mechanisms mediate the stretch dependence of $Ca^{2+}$ release in cardiomyocytes," *Nature Cell Biology* vol. 3, Oct. 2001, pp. 867-873.

Shaw, John et al., "Mechanical analysis of single myocyte contraction in a 3-D elastic matrix," PLoS ONE 8(10): e75492 doi:10.1371/journal.pone.0075492.

Thermo Scientific Pierce Assay Development Technical Handbook, Version 2 (online) 2011, https://tools.lifetechnologies.com/content/sfs/brochures/1602127-Assay-Development-Handbook.pdf>.

Wang, Jingyu et al., "A protein-based hydrogel for in vitro expansion of mesenchymal stem cells," PLoS ONE 8(9): e75727 doi:10.1371/journal.pone.0075727.

Yoshikawa, Hiroshi Y. et al., "Morphology and adhesion strength of myoblast cells on photocurable gelatin under native and non-native micromechanical environments," *J. Phys. Chem. B* 2013, 117, 4081-4088.

Tan et al., "Injectable Nanohybrid 1-15 Scaffold for Biopharmaceuticals Delivery and Soft Tissue Engineering", Macromolecular Rapid Communications, Dec. 13, 2012, vol. 33, No. 23, pp. 2015-2022.

Zhang et al., "Role of Integrins in Cellular Responses to Mechanical Stress", Prog. Biohem Biophys, 2002 pp. 359-362, vol. 19(3).

* cited by examiner

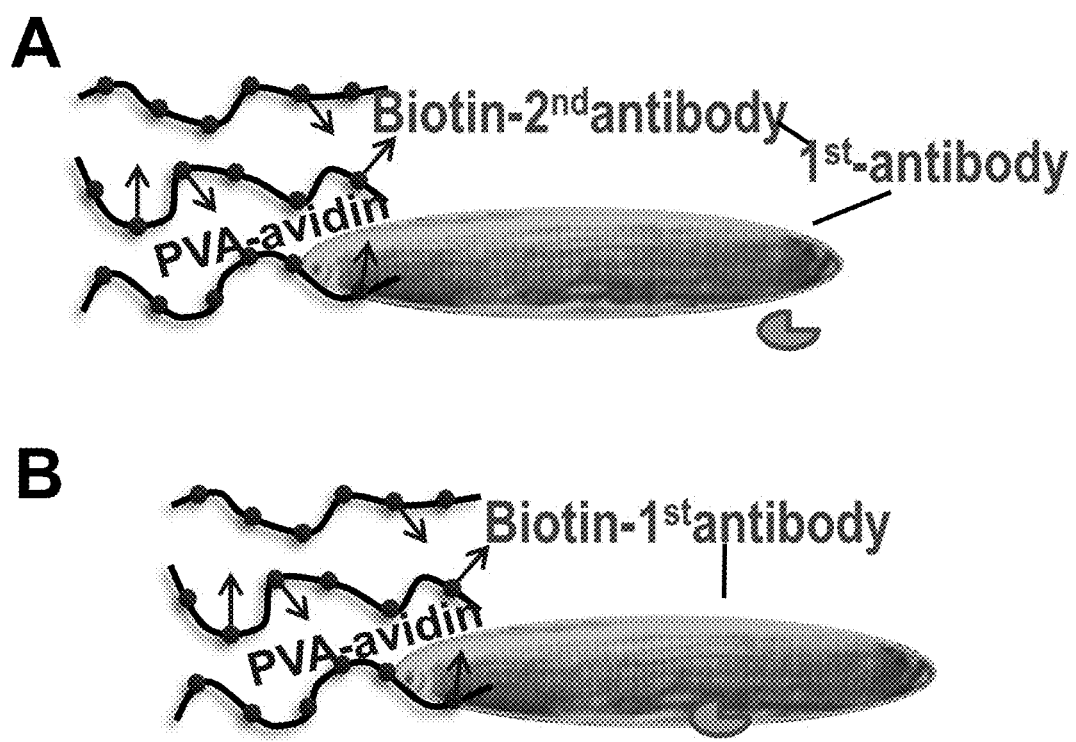
Fig. 7A-B

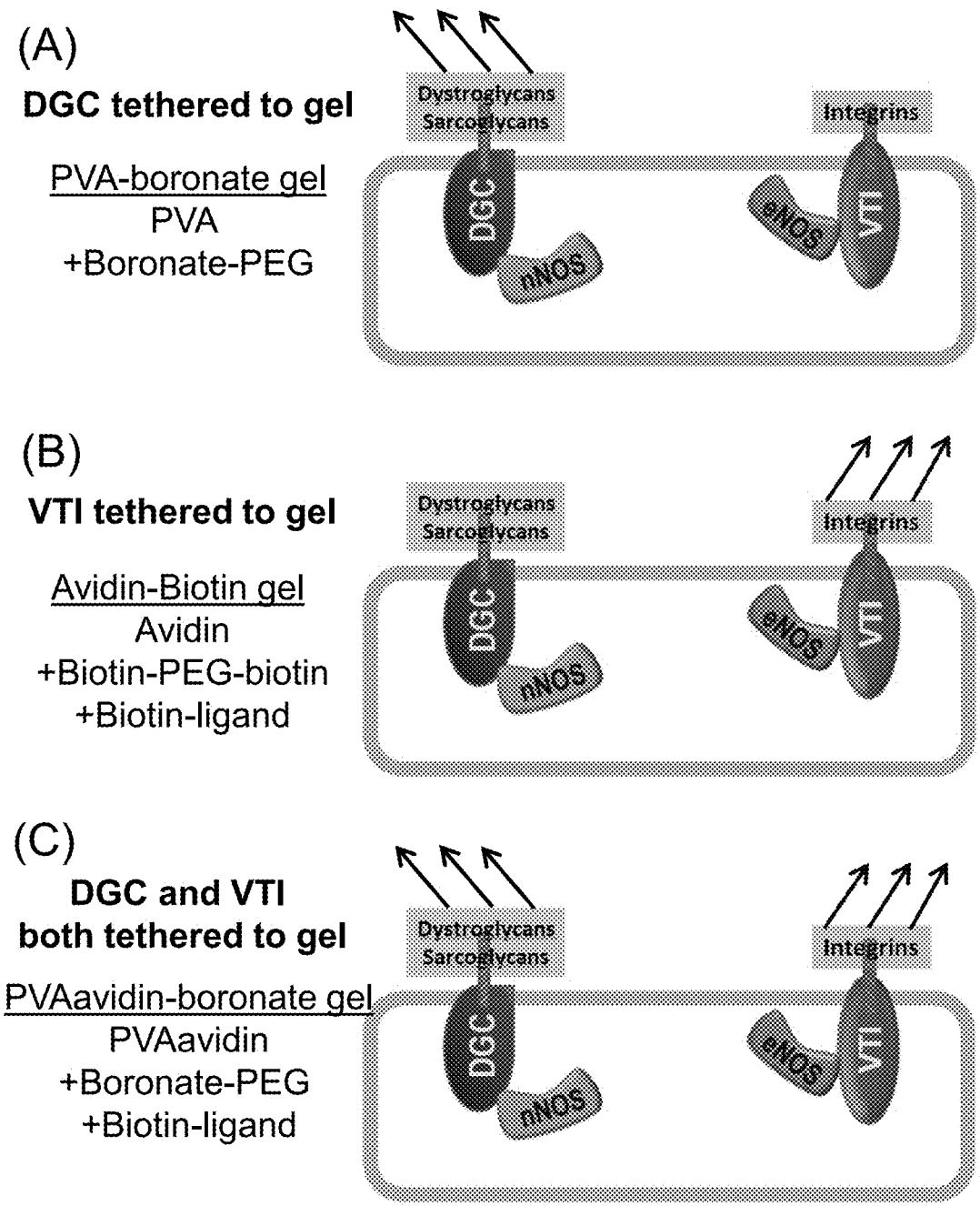
Fig. 8A-C

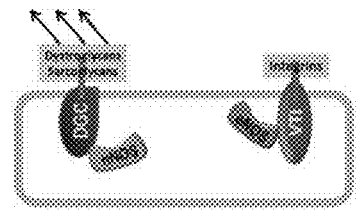
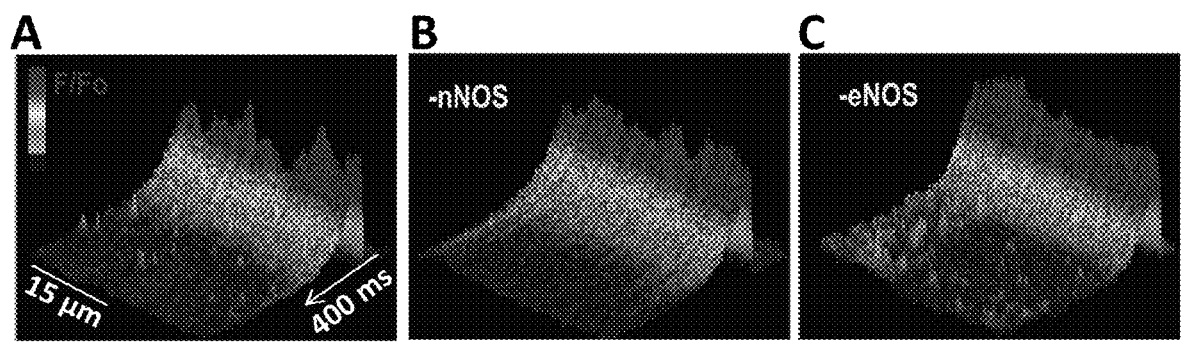
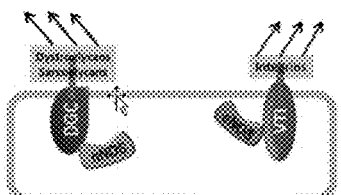
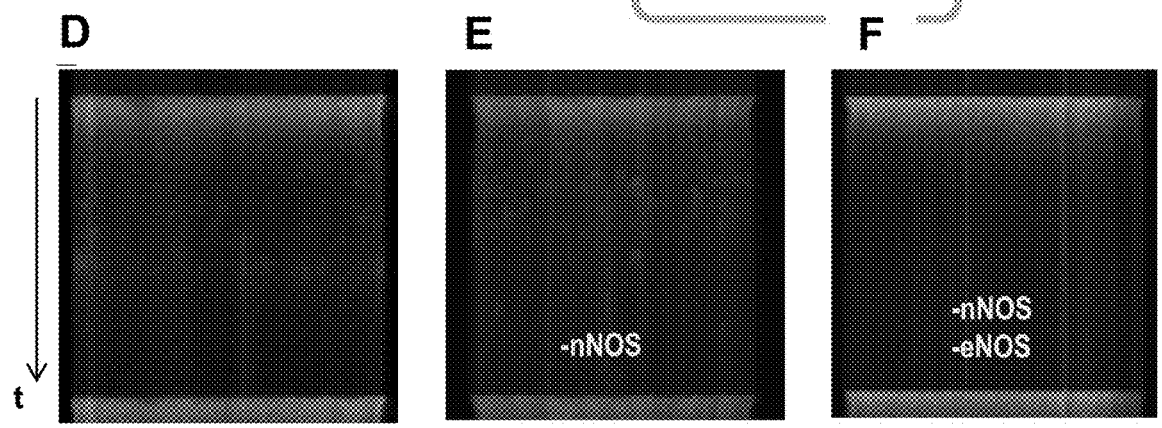
Figs. 9A-F

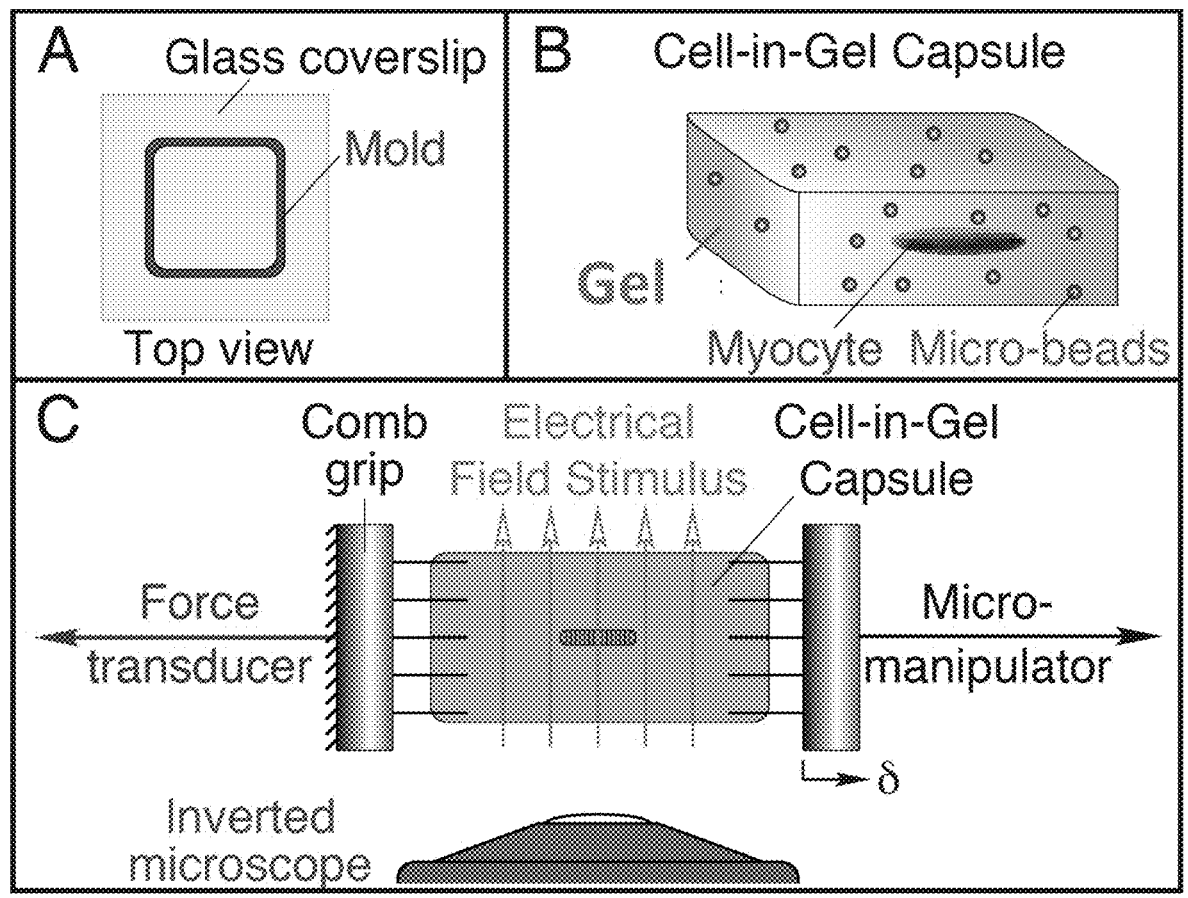
*Fig. 10A-C*

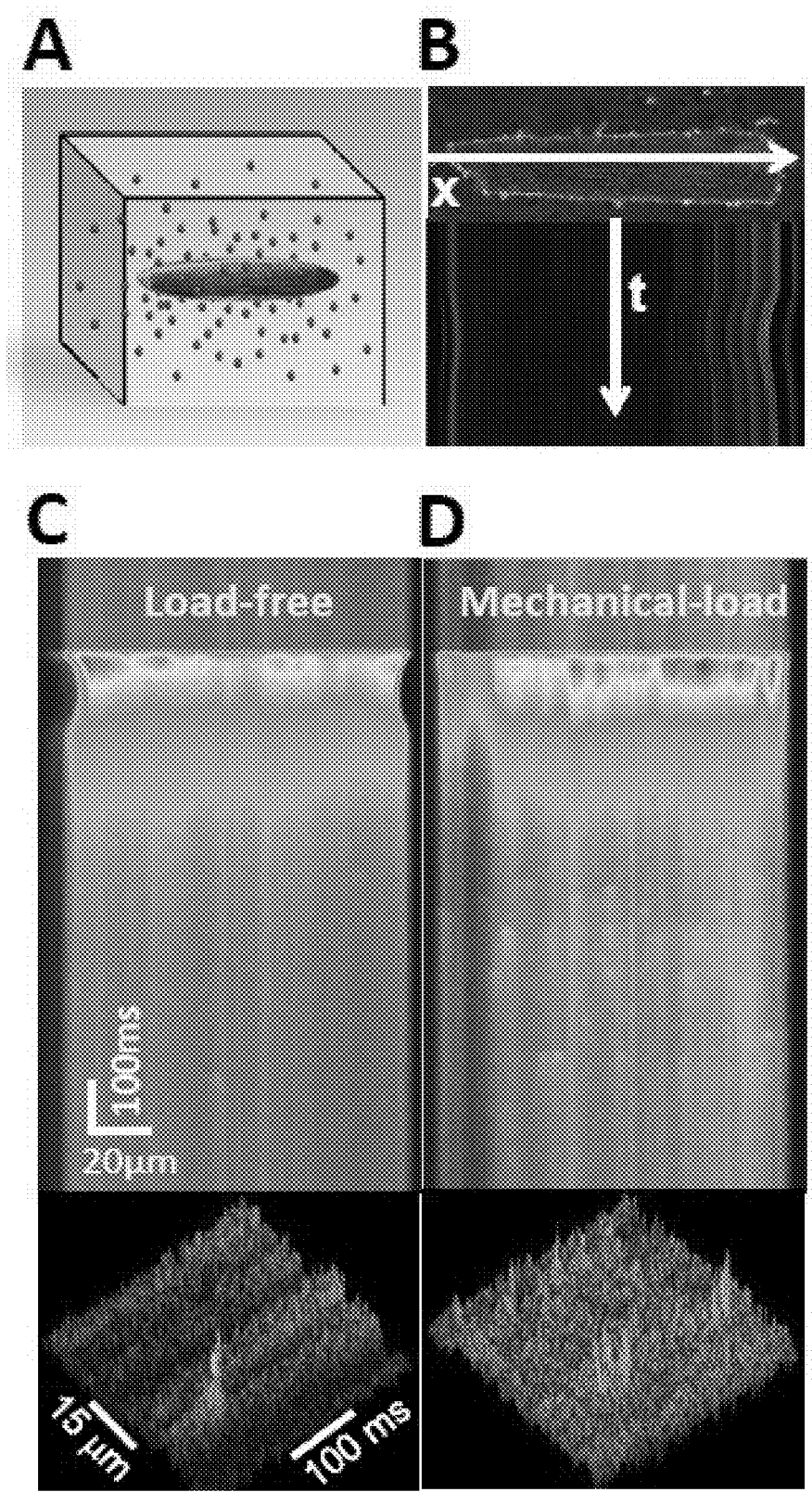
Fig. 11A-D

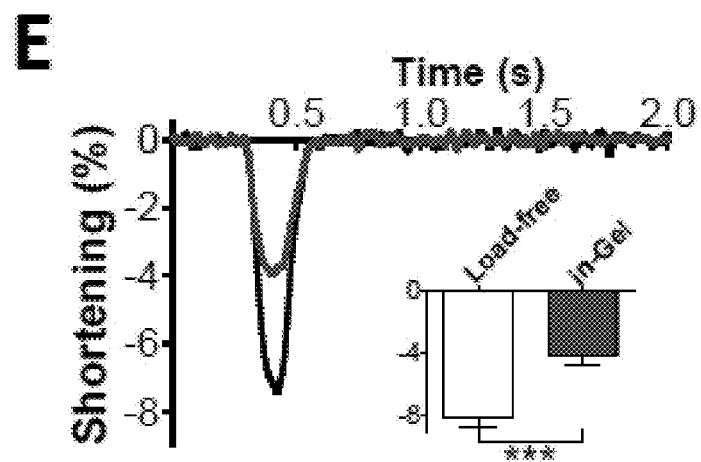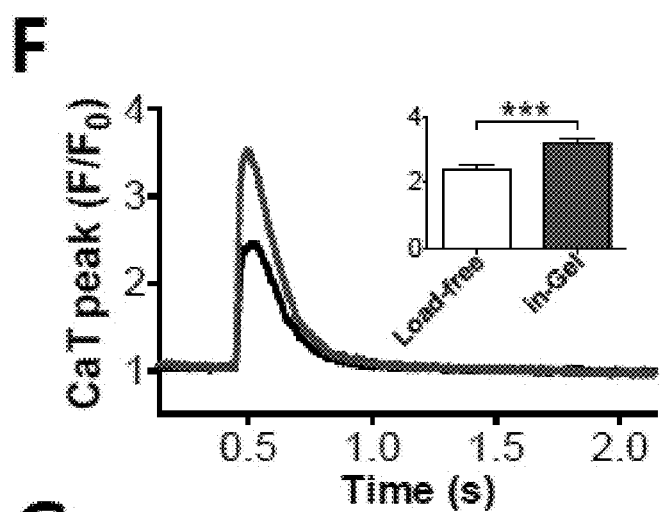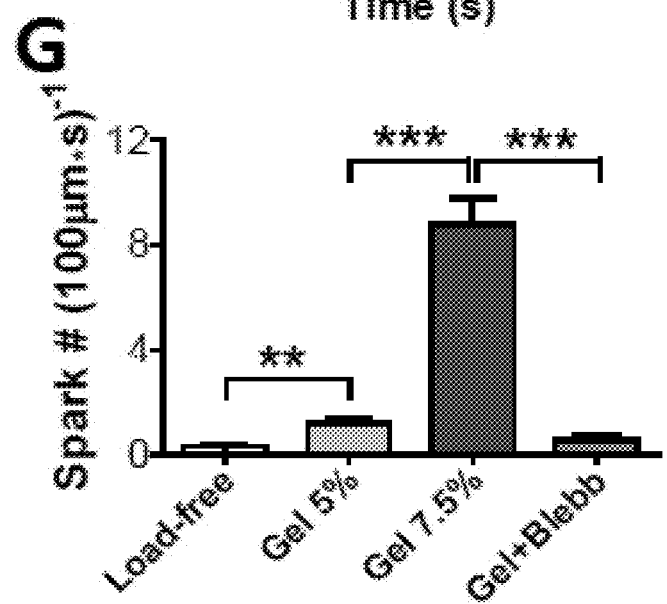
Fig. 11E-G

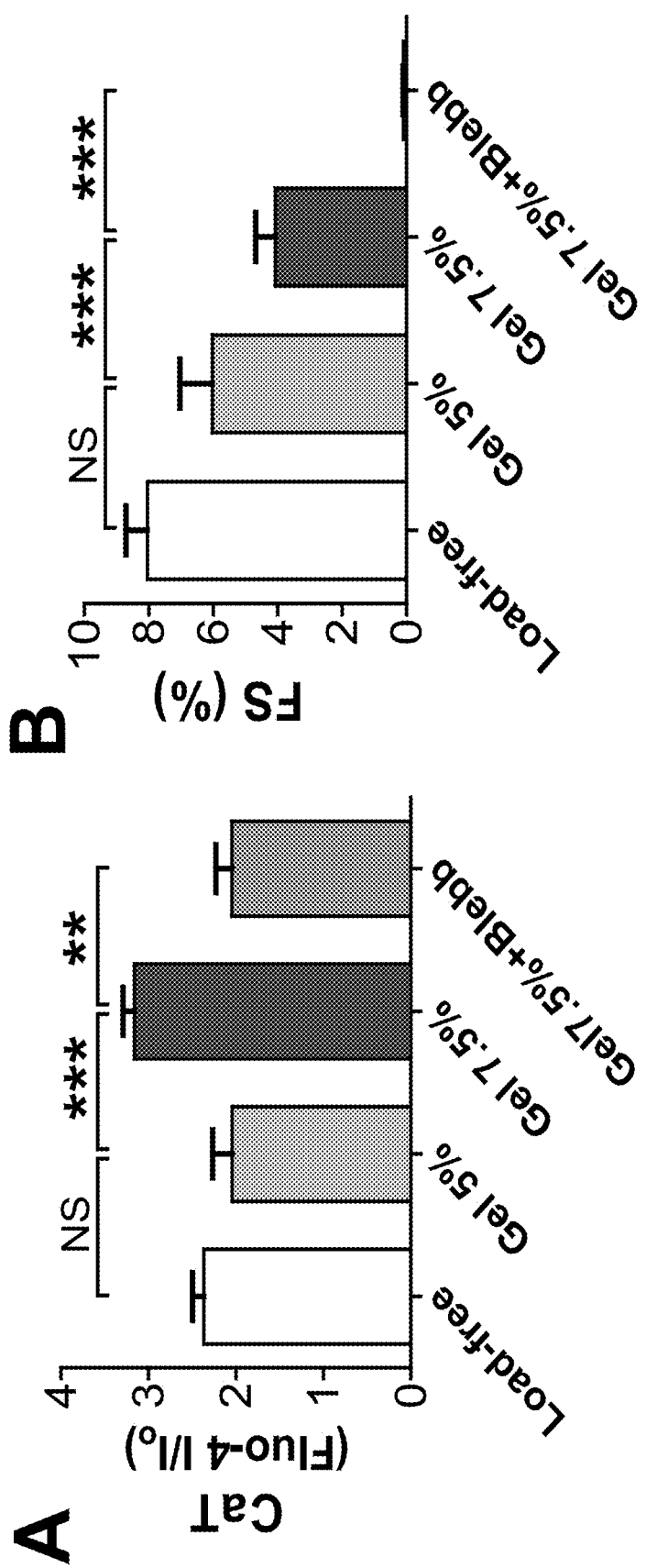
Fig. 13A-B

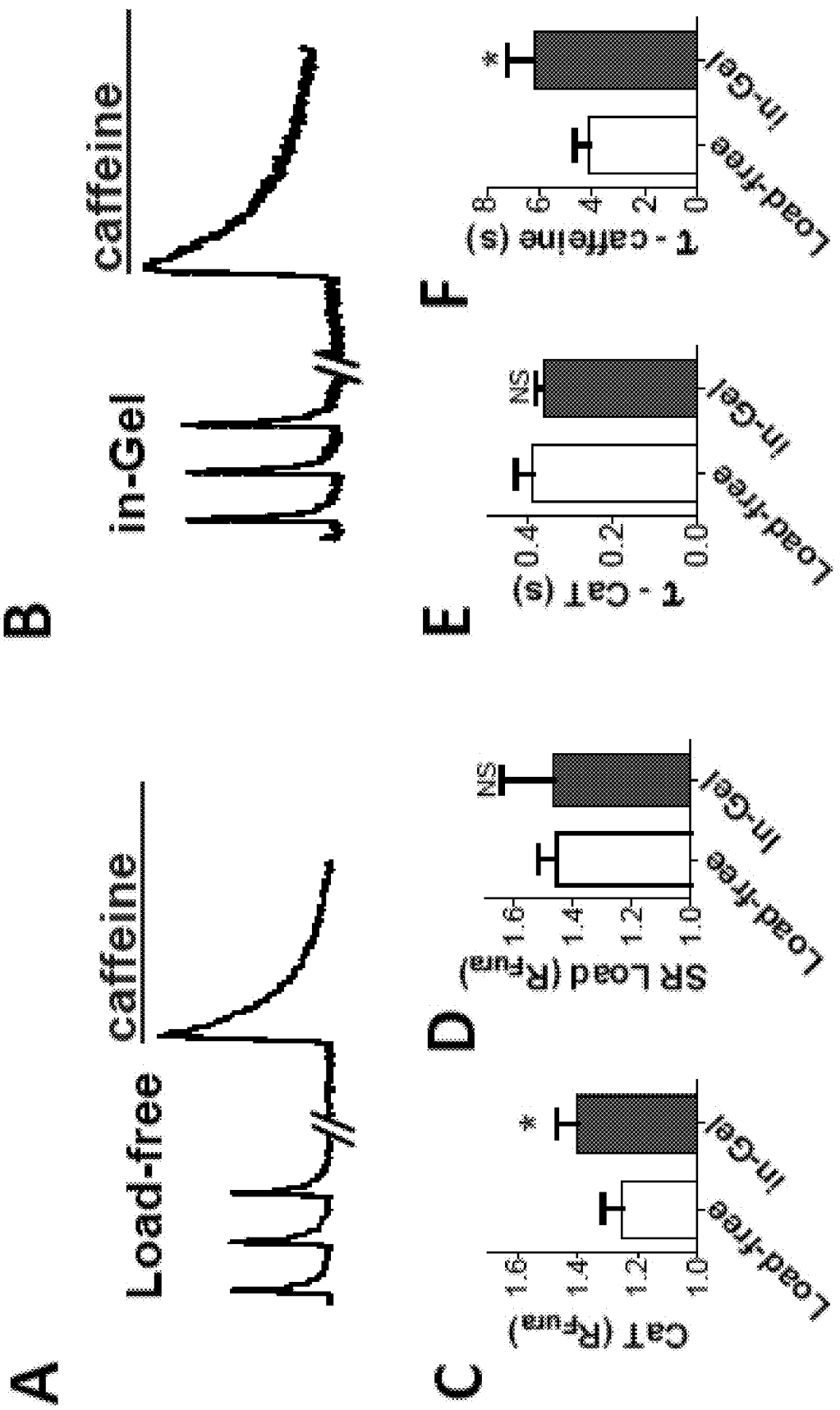
Fig. 14A-F

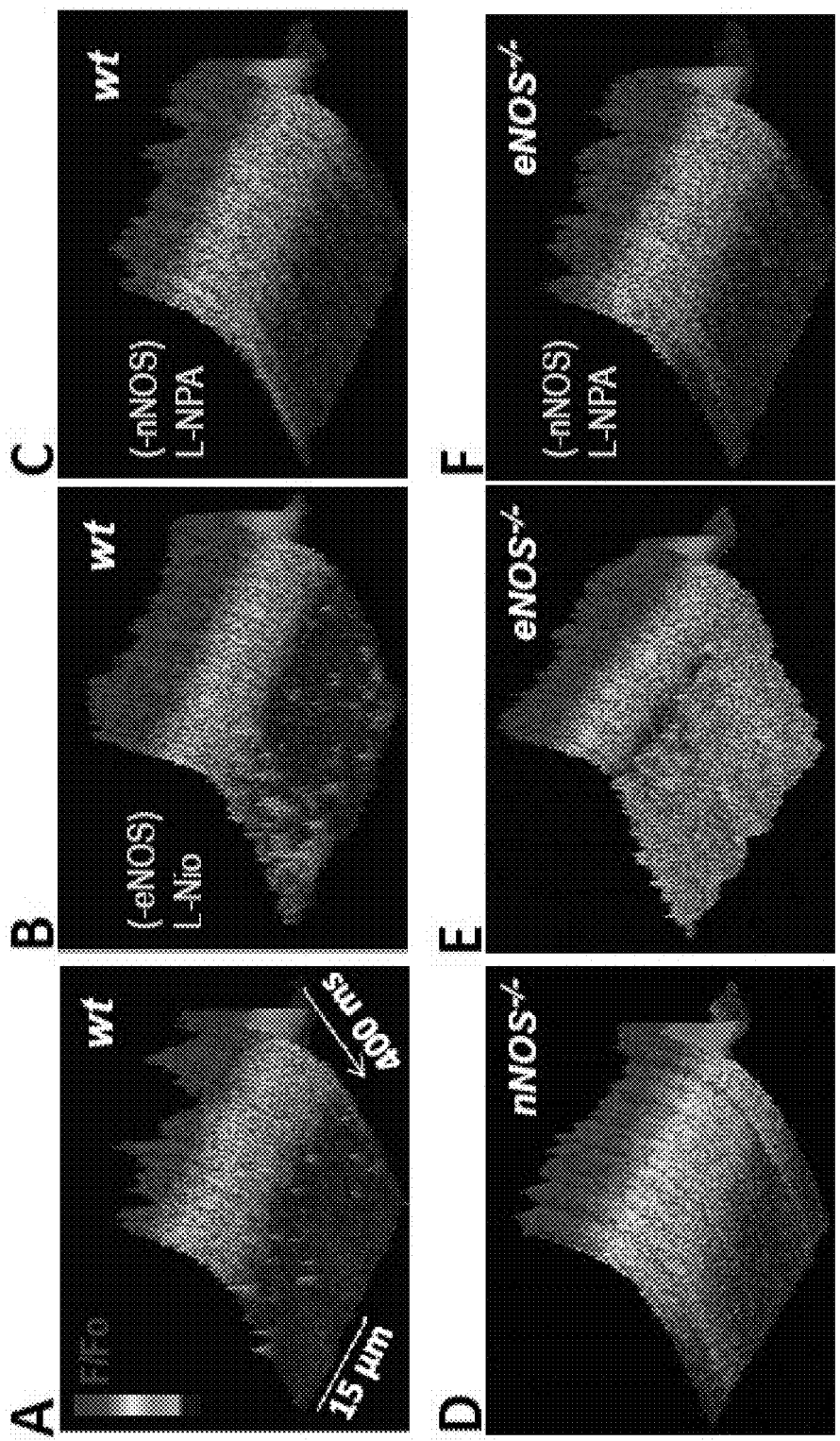
Fig. 15A-F

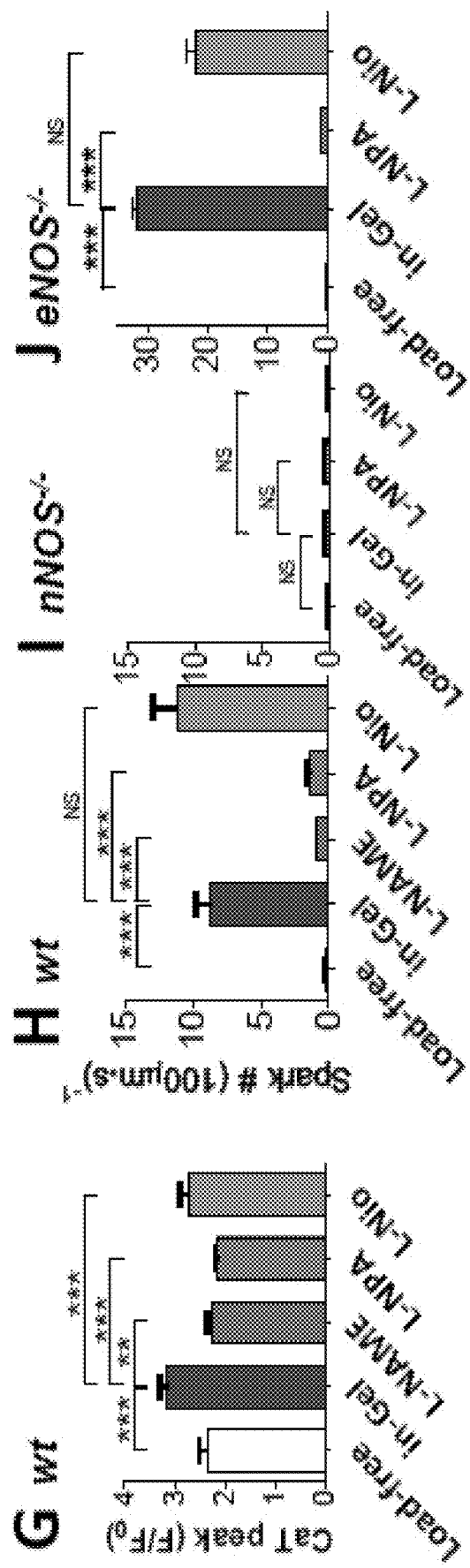
Fig. 15G-J

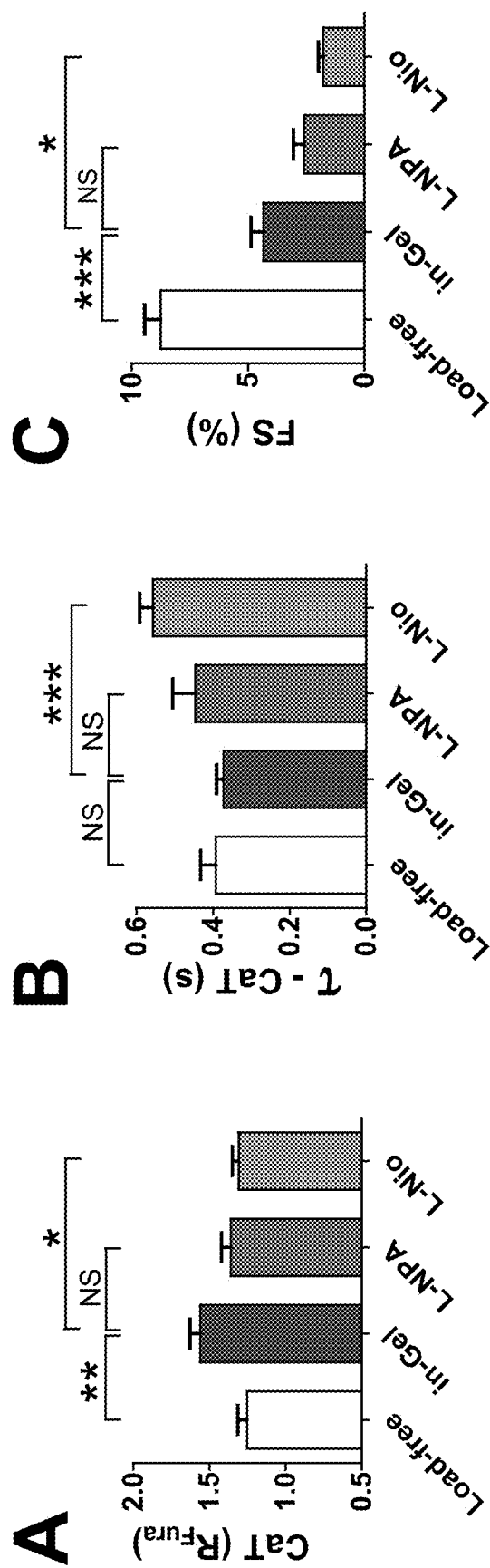
Fig. 16A-C

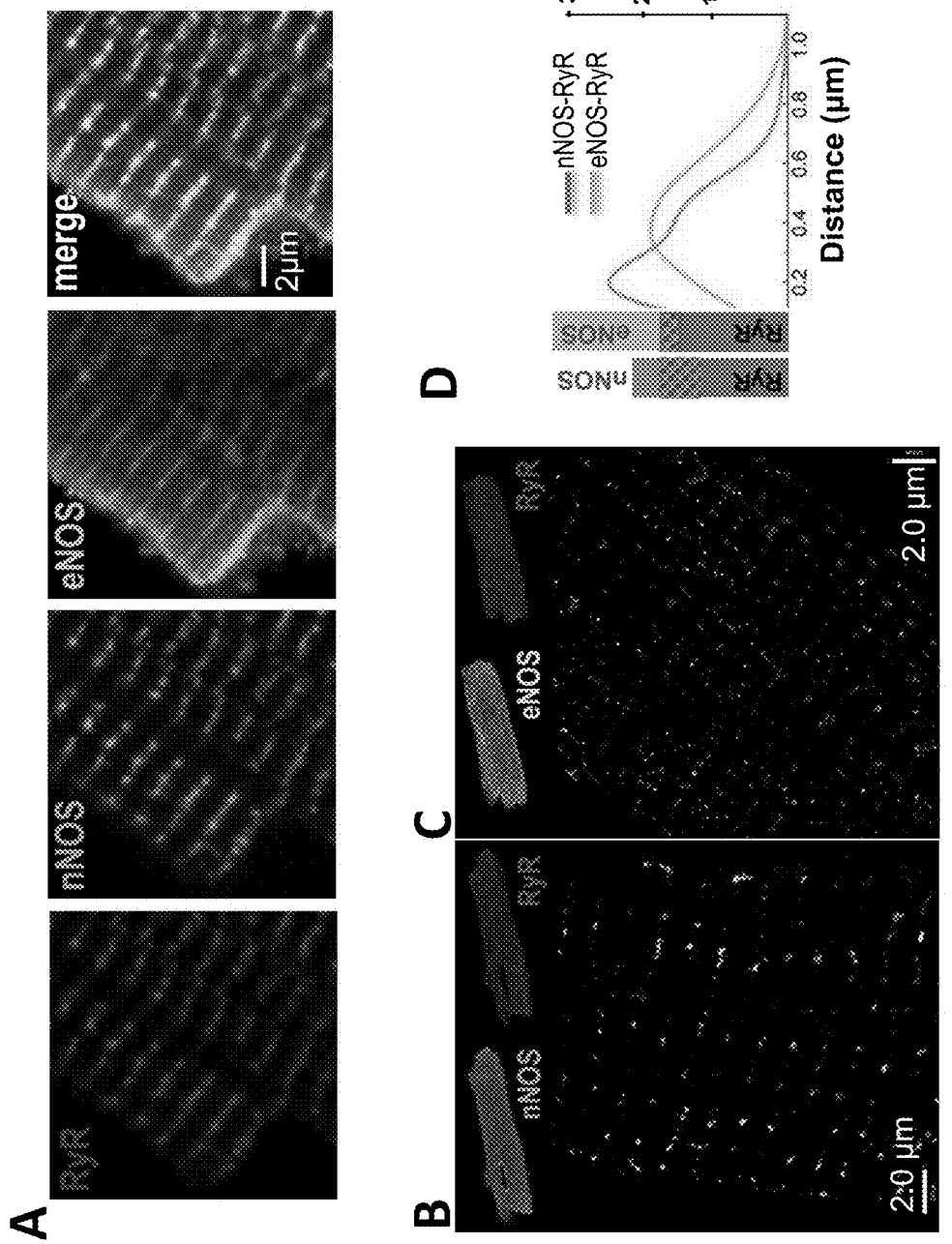
Fig. 17A-D

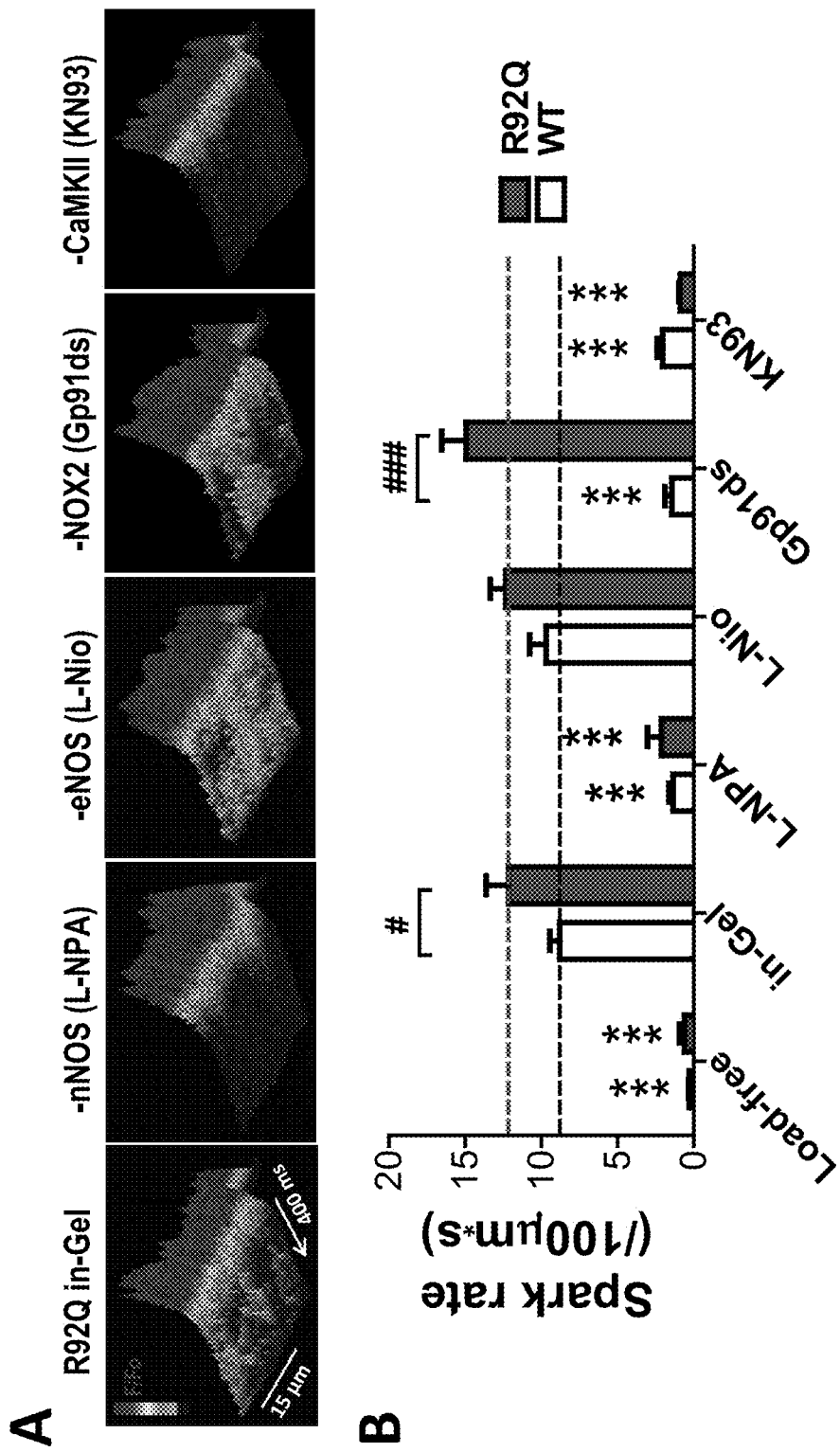
Fig. 19A-B

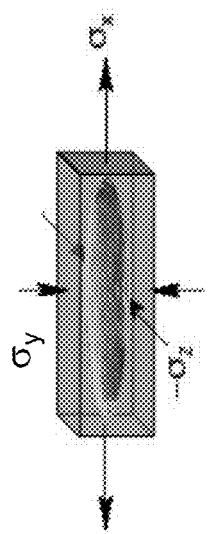
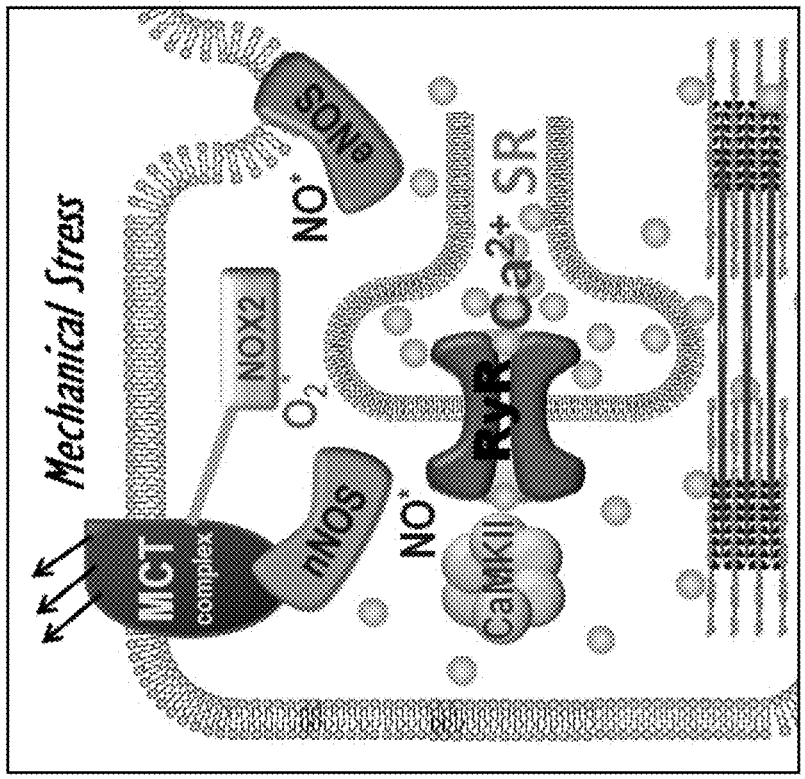
Fig. 19C

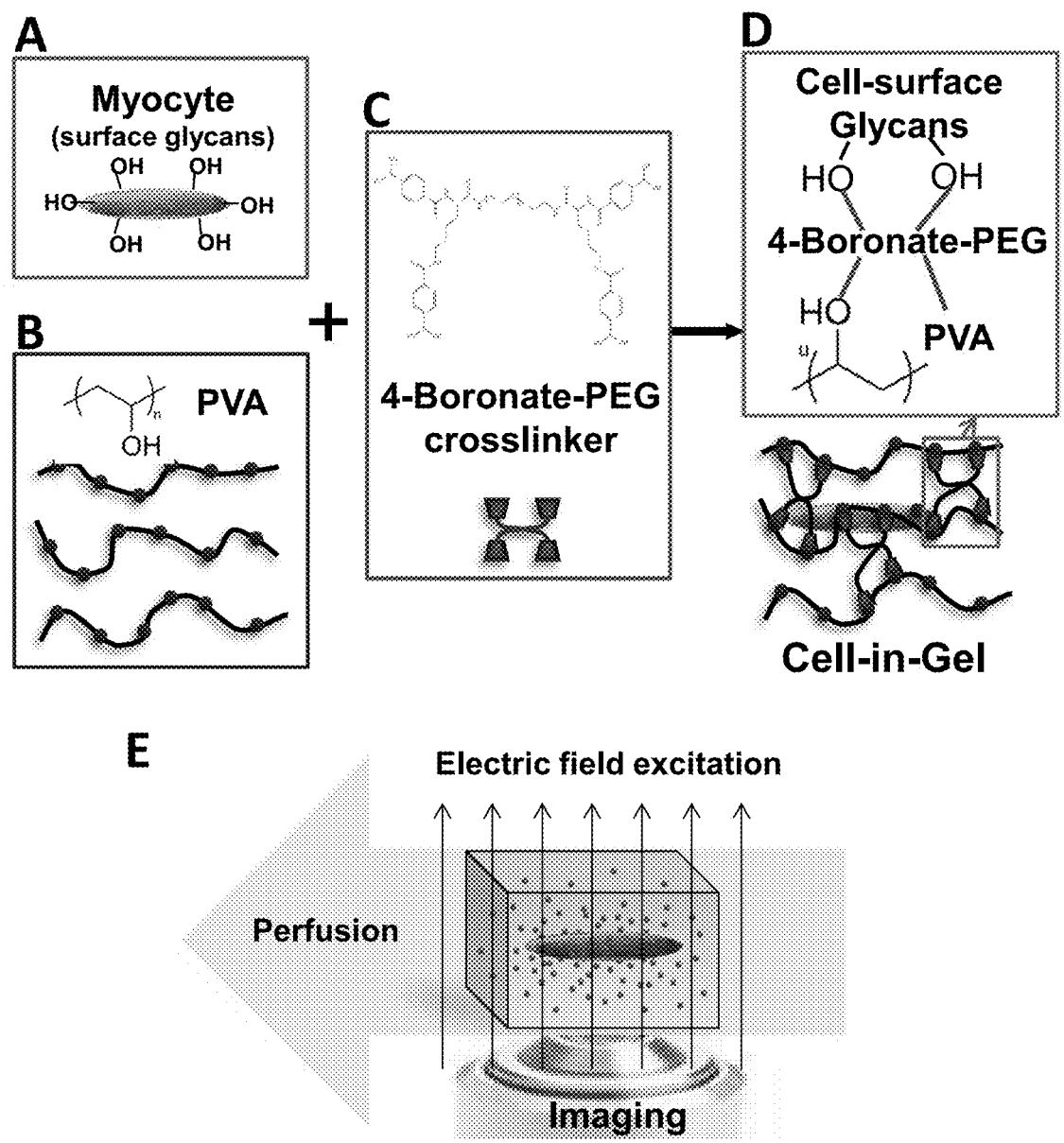
Fig. 20A-E

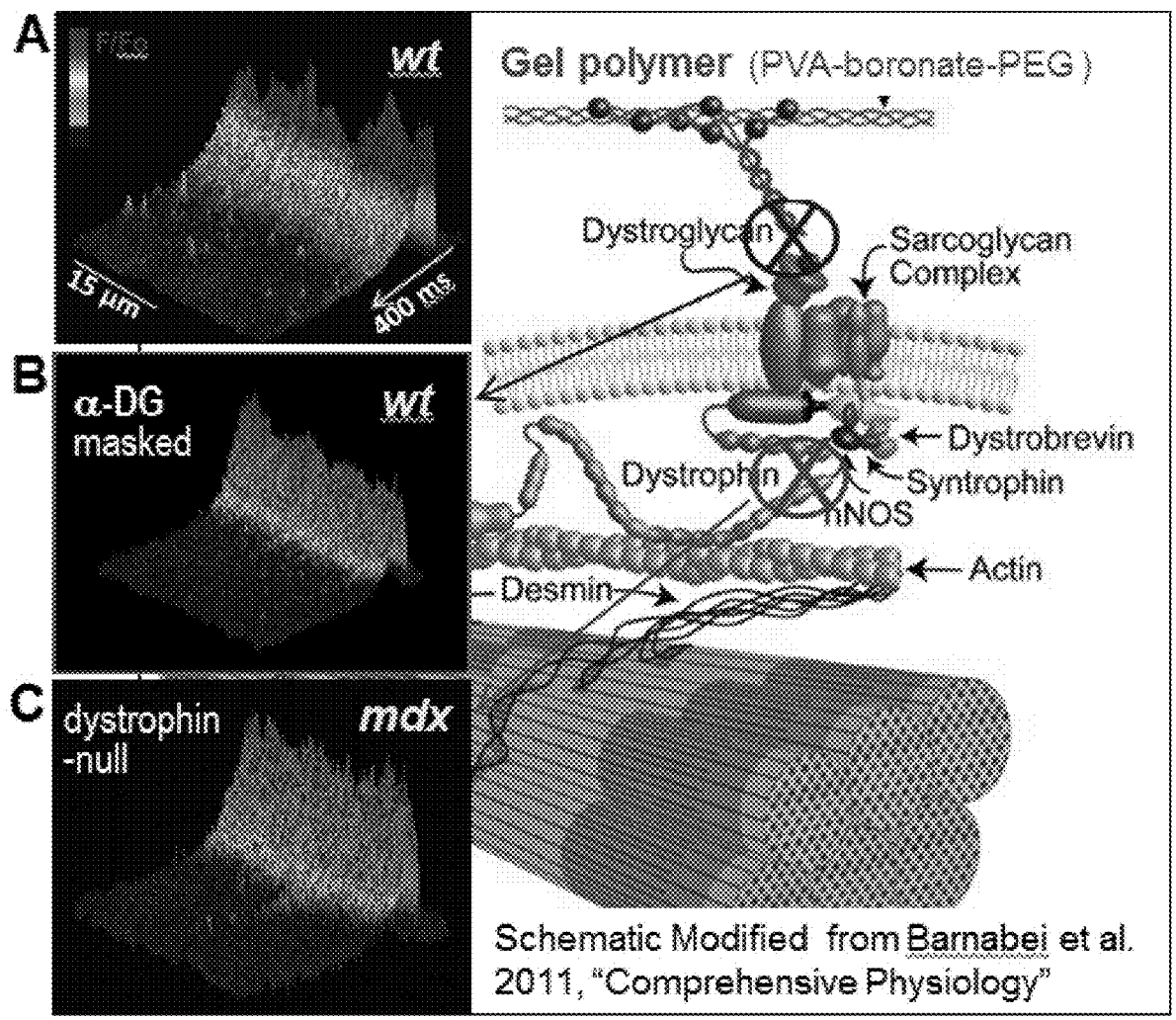
Fig. 21A-C

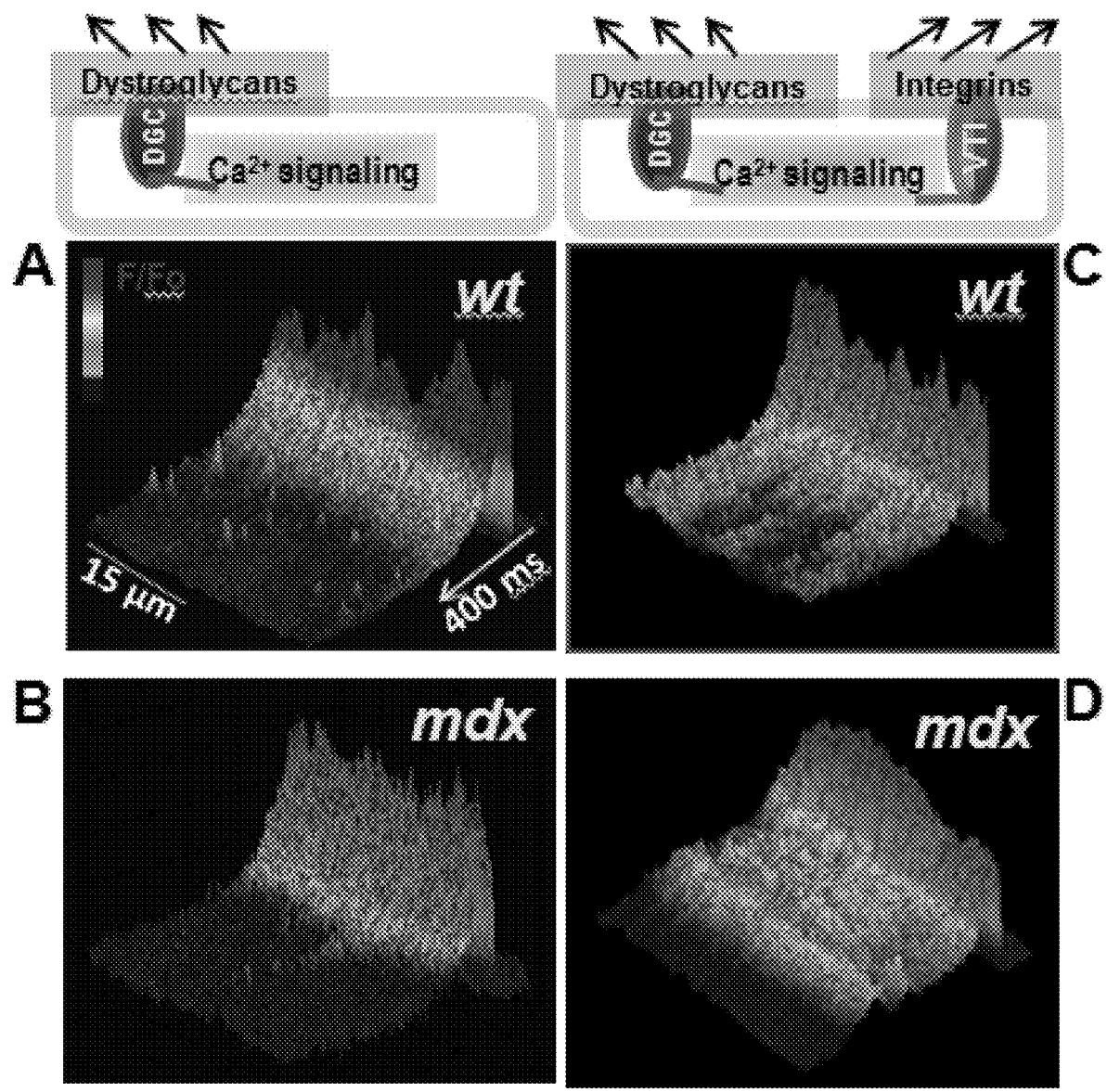
*Fig. 22A-D*

COMPOSITIONS AND METHODS FOR MEASURING CELLULAR MECHANICAL STRESS

CROSS-REFERENCE TO RELATED APPLICATIONS

This application is the U.S. national phase under 35 U.S.C. § 371 of Intl. Appl. No. PCT/US2015/018705, filed on Mar. 4, 2015, which claims the benefit under 35 U.S.C. § 119(e) of U.S. Provisional Appl. No. 61/949,049, filed on Mar. 6, 2014, which are hereby incorporated herein by reference in their entireties for all purposes.

FIELD

Provided are compositions and methods employing cells encapsulated within and attached to a hydrogel, e.g., for measuring mechanical strain and/or stress of the cell and for investigating the mechano-chemo-transduction mechanisms at cellular and molecular levels.

BACKGROUND

It is a fundamental requirement for biological cells to sense and respond to mechanical stress. In the heart, high peripheral resistance (high blood pressure, pressure-overload) is countered by increasing contractility of the myocardium, known as the Anrep effect; enlarged diastolic volume (volume overload) is also countered by increasing contractility, known as the Frank-Starling mechanism. While the heart senses mechanical stress and adjusts contractility to meet varying hemodynamic needs, excessive strain and stress (pressure-overload, volume-overload) also lead to cardiac dysfunction and heart disease development. The mechanical integrity of a cardiac myocyte is maintained by a network of structural proteins including the costamere (elaborated version of focal adhesion complex) that encircles the z-disks to provide structural support (FIG. 1). The costamere comprises the dystrophin-glycoprotein complex (DGC) and the vinculin-talin-integrin complex (VTI). The importance of these mechanical stress bearing and sensing proteins are demonstrated in various Muscular Dystrophy, in which mutations in DGC or VTI lead to cardiac dysfunction and dilated cardiomyopathy. Although these phenomena are well known for over a century, the cellular and molecular mechanisms that transduce mechanical strain and stress to intracellular biochemical reactions, so called mechano-chemo-transduction (MCT) mechanism, remains poorly understood to date. As result, effective therapies are still lacking for treating mechanical stress-induced heart diseases such as Muscular Dystrophy Cardiomyopathy and Hypertension induced Cardiac Arrhythmias and Heart Failure.

SUMMARY

In one aspect, provided are compositions comprising a cell encapsulated in a hydrogel. In varying embodiments, the hydrogel is comprised of a first binding partner of a binding partner pair or a first binding partner of the binding partner pair conjugated to a biocompatible polymer, wherein the first binding partner is cross-linked with Y—X—Y cross-linker, wherein X is a linear hydrophilic polymer and Y is a second binding partner of the binding partner pair, and wherein the cell is attached directly or indirectly to the first binding partner. In some embodiments, the hydrogel is comprised of a first binding partner of a binding partner pair conjugated to a biocompatible polymer, wherein the biocompatible polymer is cross-linked with a boronate-X-boronate crosslinker, wherein X is a linear hydrophilic polymer, and wherein the cell is attached directly or indirectly to the first binding partner. In varying embodiments, the binding partner pair is selected from the group consisting of avidin/biotin, glutathione/glutathione S-transferases (GST), maltose-binding protein (MBP)/maltose, Histag/Imidazole plus Zn2+, and vancomycin/D-alanine-D-alanine (DADA), wherein either member of the binding partner pair can be the first binding partner or the second binding partner. See, e.g., Rao, et al., Science. (1998) 280(5364):708-11. Additional binding partner pairs of use are described, e.g., in Lichty, et al., *Protein Expression and Purification* (2005) 41:98-105.

In one aspect, provided are compositions comprising a cell encapsulated in a hydrogel. In varying embodiments, the hydrogel is comprised of avidin or an avidin-polymer conjugate cross-linked with a biotin-X-biotin crosslinker, wherein X is a linear hydrophilic polymer, wherein the cell is attached directly or indirectly to the avidin. In varying embodiments, the hydrogel is comprised of avidin conjugated to a biocompatible polymer, wherein the biocompatible polymer is cross-linked with a boronate-X-boronate crosslinker, wherein X is a linear hydrophilic polymer, and wherein the cell is attached directly or indirectly to the avidin. In some embodiments, the cell is attached to the avidin via a biotin molecule. In some embodiments, the cell is attached to the avidin via a biotin molecule conjugated to a ligand.

In another aspect, provided are compositions comprising a cell encapsulated in a hydrogel. In varying embodiments, the hydrogel is comprised of biotin or biotin conjugated to a biocompatible polymer, wherein the biotin is cross-linked with an avidin-X-avidin crosslinker, wherein X is a linear hydrophilic polymer, wherein the cell is attached directly or indirectly to the biotin. In some embodiments, the hydrogel is comprised of biotin conjugated to a biocompatible polymer, wherein the biocompatible polymer is cross-linked with a boronate-X-boronate crosslinker, wherein X is a linear hydrophilic polymer, and wherein the cell is attached directly or indirectly to the biotin. In some embodiments, the cell is attached to the biotin via an avidin molecule. In some embodiments, the cell is attached to the biotin via an avidin molecule conjugated to a ligand.

In varying embodiments of the compositions, the boronate in the boronate-X-boronate crosslinker is selected from the group consisting of diboronate, triboronate, tetraboronate and mixtures thereof. In some embodiments, the avidin is selected from avidin, streptavidin, neutravidin and captavidin. In varying embodiments, the vancomycin and the D alanine-D-alanine (DADA) are monovalent, divalent or trivalent. In varying embodiments, the hydrogel is comprised of a ligand conjugated to a biocompatible polymer, wherein the biocompatible polymer is cross-linked with a boronate-X-boronate crosslinker, wherein X is a linear hydrophilic polymer, wherein the cell is attached directly or indirectly to the ligand. In some embodiments, the biocompatible polymer comprises an average molecular weight in the range of about 50-150 kDa, e.g., about 80-100 kDa, e.g., about 50 kDa, 60 kDa, 70 kDa, 80 kDa, 90 kDa, 100 kDa, 110 kDa, 120 kDa, 130 kDa, 140 kDa or 150 kDa. In varying embodiments, the biocompatible polymer comprises functional moieties for cross-linking selected from the group consisting of hydroxyl, diol (e.g., cis-diol), carboxyl, amino, amino-oxy, azide, or alkyne. In varying embodiments, the biocompatible polymer comprises cis-diol moieties for cross-linking. In some embodiments, the biocompatible polymer is selected from the group consisting of polyvinyl alcohol (PVA), agarose and alginate. In some embodiments, the crosslinker comprises a molecular weight in the range of about 1-50 kDa, e.g., about 10-30 kDa, e.g., about 15-25 kDa, e.g., about 5 kDa, 10 kDa, 15 kDa, 20 kDa, 25 kDa, 30 kDa, 35 kDa, 40 kDa, 45 kDa or 50 kDa. In some embodiments, X is a linear hydrophilic polymer, e.g., polyethylene glycol (PEG), poly(propylene glycol) (PPG), alginate, agarose, chitosan, and linear oligosaccharides. In some embodiments, the wt./wt. ratio of the crosslinker to the polymer is in the range of about 0.2 to about 5.0, e.g., 0.2 to about 2.0, e.g., about 0.5 to about 1.5. In some embodiments, the hydrogel comprises a stiffness or Young's modulus value in the range of about 0.1 kPa to about 100 kPa. In varying embodiments, the hydrogel is optically transparent. In some embodiments, the ligand binds to a cell surface molecule. In some embodiments, the surface molecule is selected from the group consisting of an integrin, a glycoprotein, a glycan, and a cell surface receptor. In some embodiments, the ligand is selected from a polypeptide, a linear peptide, a circularized peptide, a peptidomimetic, an antigen binding molecule, an antibody and an antibody fragment. In some embodiments, the ligand is a polypeptide selected from the group consisting of collagen, laminin, fibronectin, fibrinogen, vitronectin, VCAM-1 and cadherin, and subsequences thereof. In some embodiments, the integrin is selected from the group consisting of an $\alpha 3\beta 1$ integrin, an $\alpha 4\beta 1$ integrin, and an $\alpha v\beta 3$ integrin. In some embodiments, the cell is a myocyte. In some embodiments, the cell is a cardiac myocyte, a skeletal muscle myocyte or a smooth muscle myocyte. In some embodiments, the myocyte is a cardiac myocyte. In some embodiments, the encapsulated cell is not contacting or capable of contacting a solid surface or another cell.

In another aspect, provided is a device comprising the compositions as described above and herein. In varying embodiments, the device comprises one or more perfusion chambers. In varying embodiments, the one or more perfusion chambers comprise a modified Tyrode solution comprising pyruvic acid substituted for glucose. In varying embodiments, the modified Tyrode solution comprises a $Ca^{2+}$ concentration is sufficiently low to allow a myocyte to be in a relaxed state. In varying embodiments, the modified Tyrode solution comprises a $Ca^{2+}$ concentration that is less than about 1 mM, e.g., less than about 100 µM, 75 µM, 50 µM, 40 µM or 30 µM and at least about 10 µM. In varying embodiments, the encapsulated cell is not in contact with a solid surface of the device or another cell within the hydrogel. In varying embodiments, the gel is tethered in at least two dimensions. In varying embodiments, the device comprises grips that tether the gel, wherein the grips can pull on the gel, thereby introducing mechanical strain and/or stress on the gel and the cell encapsulated in the gel. In varying embodiments, the gel is in mechanical communication with a force transducer and a tension manipulator. In varying embodiments, the gel is within an electric field controlled by an electrical stimulator that applies electrical signals to the cell encapsulated in the gel. In varying embodiments, the device is in communication with an imaging system. In varying embodiments, the device is in communication with a computer. In varying embodiments, the computer records mechanical strain and/or stress imposed on the cell and the gel. In varying embodiments, the computer records cellular images.

In a further aspect, provided is a system. In some embodiments, the system comprises:

i) one or more perfusion chambers, each perfusion chamber comprising a composition as described above and herein;

ii) first and second grips in contact with the gel, wherein the first and second grips can introduce tension on the gel in at least two dimensions;

iii) a force transducer connected to the first grip and a tension manipulator connected to the second grip, wherein the force transducer senses mechanical tension imposed on the gel which can be used to calculate the stress in the cell and the gel;

iv) a computer in communication with the force transducer, wherein the computer can store the mechanical tension readings sensed by the force transducer. In varying embodiments, the system further comprises an imaging system that can capture images of the cell encapsulated in the gel, wherein the imaging system is in communication with one or both of the force transducer and the computer. In varying embodiments, the system further comprises an electrical stimulator that applies electrical signals to the cell encapsulated in the gel. In varying embodiments, the perfusion chamber comprises a modified Tyrode solution comprising pyruvic acid substituted for glucose. In varying embodiments, the modified Tyrode solution comprises a $Ca^{2+}$ concentration is sufficiently low to allow a myocyte to be in a relaxed state. In varying embodiments, the modified Tyrode solution comprises a $Ca^{2+}$ concentration that is less than 1 mM, e.g., less than 100 µM, 75 µM, 50 µM and at least about 10 µM. In varying embodiments, the computer is programmed to control and/or govern administration of a test stimulus to the perfusion chamber.

In another aspect, provided are methods of monitoring mechanical strain and/or stress on a cell. In some embodiments, the methods comprise:

a) encapsulating a cell in a composition as described above and herein;

b) obtaining a first measurement of the mechanical strain and/or stress on the cell;

c) exposing the cell to a test stimulus;

d) obtaining a second measurement of the mechanical strain and/or stress on the cell; and e) comparing the first and second measurements. In varying embodiments, the cell is a myocyte. In varying embodiments, the myocyte is a cardiac myocyte, a skeletal muscle myocyte or a smooth muscle myocyte. In varying embodiments, the myocyte is a cardiac myocyte. In varying embodiments, myocyte contraction is measured. In varying embodiments, the methods further comprise continuously recording and measuring the mechanical strain and/or stress on the cell. In varying embodiments, the methods further comprise introducing mechanical strain and/or stress on the gel prior to exposing the cell to the test stimulus. In varying embodiments, the methods further comprise introducing mechanical strain and/or stress on the gel before, during and/or after exposing the cell to the test stimulus. In varying embodiments, the test stimulus is physical, chemical or pharmacological. In varying embodiments, the first and/or second measurements of mechanical strain and/or stress on the cell are recorded in a computer readable medium.

In another aspect, provided are methods of producing the cell-in-gel compositions described above and herein. In some embodiments, the methods comprise:

a) incubating one or more cells with a second binding partner of a binding partner pair-ligand conjugate under conditions allowing the ligand to bind to one or more cell surface molecules on the one or more cells;

b) contacting the cells bound to the second binding partner-ligand conjugate with a first binding partner of a binding partner pair or a biocompatible polymer comprising the first binding partner under conditions sufficient for the first binding partner to bind the second binding partner of the second binding partner-ligand conjugate; and c) contacting the cells from step b) with a Y—X—Y crosslinker under conditions sufficient to crosslink the first binding partner, wherein X is a linear hydrophilic polymer and Y is the second binding partner of the binding partner pair, thereby encapsulating the cells in a hydrogel.

In some embodiments, the methods comprise:

a) incubating one or more cells with a second binding partner of a binding partner pair-ligand conjugate under conditions allowing the ligand to bind to one or more cell surface molecules on the one or more cells;

b) contacting the cells bound to the second binding partner of a binding partner pair-ligand conjugate with a biocompatible polymer conjugated to a first binding partner of a binding partner pair under conditions sufficient for the first binding partner to bind to the second binding partner-ligand conjugate; and c) contacting the cells from step b) to a boronate-X-boronate crosslinker under conditions sufficient to crosslink the biocompatible polymer, wherein X is a linear hydrophilic polymer, thereby encapsulating the cells in a hydrogel.

In varying embodiments of the methods of producing, the binding partner pair is selected from the group consisting of avidin/biotin, glutathione/glutathione S-transferases (GST), maltose-binding protein (MBP)/maltose, Histag/Imidazole plus Zn2+, and vancomycin/D-alanine-D-alanine (DADA).

In some embodiments, the methods comprise:

a) incubating one or more cells with a biotin-ligand conjugate under conditions allowing the ligand to bind to one or more cell surface molecules on the one or more cells;

b) contacting the cells bound to the biotin-ligand conjugate with avidin or a biocompatible polymer comprising or conjugated to avidin under conditions sufficient for the avidin to bind the biotin of the biotin-ligand conjugate; and c) contacting the cells from step b) with a biotin-X-biotin crosslinker under conditions sufficient to crosslink the avidin, wherein X is a linear hydrophilic polymer, thereby encapsulating the cells in a hydrogel.

In some embodiments, the methods comprise:

a) incubating one or more cells with a biotin-ligand conjugate under conditions allowing the ligand to bind to one or more cell surface molecules on the one or more cells;

b) contacting the cells bound to the biotin-ligand conjugate with a biocompatible polymer conjugated to avidin under conditions sufficient for the avidin to bind to the biotin-ligand conjugate; and c) contacting the cells from step b) to a boronate-X-boronate crosslinker under conditions sufficient to crosslink the biocompatible polymer, wherein X is a linear hydrophilic polymer, thereby encapsulating the cells in a hydrogel.

In some embodiments, the methods comprise:

a) incubating one or more cells with an avidin-ligand conjugate under conditions allowing the ligand to bind to one or more cell surface molecules on the one or more cells;

b) contacting the cells bound to the avidin-ligand conjugate with biotin or a biocompatible polymer comprising biotin under conditions sufficient for the biotin to bind the avidin of the avidin-ligand conjugate; and c) contacting the cells from step b) with an avidin-X-avidin crosslinker under conditions sufficient to crosslink the biotin, thereby encapsulating the cells in a hydrogel. In varying embodiments, X is a linear hydrophilic polymer, e.g., polyethylene glycol (PEG), poly(propylene glycol) (PPG), alginate, agarose, chitosan, and linear oligosaccharides.

In some embodiments, the methods comprise:

a) incubating one or more cells with an avidin-ligand conjugate under conditions allowing the ligand to bind to one or more cell surface molecules on the one or more cells;

b) contacting the cells bound to the avidin-ligand conjugate with a biocompatible polymer conjugated to biotin under conditions sufficient for the biotin to bind to the avidin-ligand conjugate; and c) contacting the cells from step b) to a boronate-X-boronate crosslinker under conditions sufficient to crosslink the biocompatible polymer, thereby encapsulating the cells in a hydrogel. In varying embodiments, X is a linear hydrophilic polymer, e.g., polyethylene glycol (PEG), poly(propylene glycol) (PPG), alginate, agarose, chitosan, and linear oligosaccharides.

In varying embodiments of the methods for producing a hydrogel, the one or more cells are encapsulated with or without mechanical mixing. As discussed above and herein, X can be any hydrophilic linear polymer. In varying embodiments, X is a linear hydrophilic polymer, e.g., polyethylene glycol (PEG), poly(propylene glycol) (PPG), alginate, agarose, chitosan, and linear oligosaccharides. Further embodiments of the methods for producing a hydrogel are described above and herein.

In another aspect, provided are kits. In some embodiments, the kits comprise: i) a solution comprising a first binding partner of a binding partner pair or a biocompatible polymer conjugated to the first binding partner; and ii) a solution comprising a Y—X—Y crosslinker; wherein X is a linear hydrophilic polymer and Y is a second binding partner of the binding partner pair. In some embodiments, the kits comprise: i) a solution comprising a biocompatible polymer conjugated to a first binding partner of a binding partner pair; and ii) a solution comprising a boronate-X-boronate crosslinker; wherein X is a linear hydrophilic polymer. In varying embodiments, the binding partner pair is selected from the group consisting of avidin/biotin, glutathione/glutathione S-transferases (GST), maltose-binding protein (MBP)/maltose, Histag/Imidazole plus Zn2+, and vancomycin/D-alanine-D-alanine (DADA), and either member of the binding partner pair can be the first binding partner or the second binding partner. In some embodiments, the kits comprise: i) a solution comprising avidin or a biocompatible polymer conjugated to avidin; and ii) a solution comprising a biotin-X-biotin crosslinker; wherein X is a linear hydrophilic polymer. In some embodiments, the kits comprise: i) a solution comprising a biocompatible polymer conjugated to avidin; and ii) a solution comprising a boronate-X-boronate crosslinker; wherein X is a linear hydrophilic polymer. In some embodiments, the kits comprise: i) a solution comprising biotin or a biocompatible polymer conjugated to biotin; and; ii) a solution comprising an avidin-X-avidin crosslinker; wherein X is a linear hydrophilic polymer. In some embodiments, the kits comprise: i) a solution comprising a biocompatible polymer conjugated to biotin; and ii) a solution comprising a boronate-X-boronate crosslinker; wherein X is a linear hydrophilic polymer. In some embodiments, the boronate in the boronate-X-boronate crosslinker is selected from the group consisting of diboronate, triboronate, tetraboronate, and mixtures thereof. In some embodiments, the kits further comprise a a solution comprising biotin-ligand conjugate. In some embodiments, the avidin is selected from avidin, streptavidin, neutravidin and captavidin. In some embodiments, the biocompatible polymer comprises an average molecular weight in the range of about 50-150 kDa, e.g., about 80-100 kDa, e.g., about 50 kDa, 60 kDa, 70 kDa, 80 kDa, 90 kDa, 100 kDa, 110 kDa, 120 kDa, 130 kDa, 140 kDa or 150 kDa. In some embodiments, the biocompatible polymer comprises cis-diol moieties for cross-linking. In some embodiments, the biocompatible polymer is selected from the group consisting of polyvinyl alcohol (PVA), agarose and alginate. In some embodiments, the crosslinker comprises a molecular weight in the range of about 1-50 kDa, e.g., about 10-30 kDa, e.g., about 15-25 kDa, e.g., about 5 kDa, 10 kDa, 15 kDa, 20 kDa, 25 kDa, 30 kDa, 35 kDa, 40 kDa, 45 kDa or 50 kDa. In some embodiments, X is a linear hydrophilic polymer, e.g., poly-ethylene glycol (PEG), poly(propylene glycol) (PPG), alginate, agarose, chitosan, and linear oligosaccharides.

Definitions

As used herein, the term "cell adhesion matrix" refers to a 3-dimensional matrix culture system that emulates physical and molecular features of the extracellular microenvironment. The cell adhesion matrix of the present invention is formed by crosslinking biocompatible polymer chains using crosslinkers having at least two functional groups to bind to two adjacent functional groups of the biocompatible polymer chains.

As used herein, the term "contacting" refers to the process of bringing into contact at least two distinct species such that they can react. It should be appreciated, however, the resulting reaction product can be produced directly from a reaction between the added reagents or from an intermediate from one or more of the added reagents which can be produced in the reaction mixture.

As used herein, the term "polyvinyl alcohol chains" refers to polymer chains of polyvinyl alcohol. The poly(vinyl alcohol) chains can have any molecular weight, and are described in more detail below.

As used herein, the term "crosslinked" refers to the state of having numerous biocompatible polymer chains interconnected to each other via the boronic acid crosslinkers such that they become a single structure. The chemical functionality that links the individual biocompatible polymer chains that are crosslinked, is termed a "crosslinker". A crosslinker is typically a multifunctional compound that reacts with at least one functional group on one biocompatible polymer chain and one reactive functional group on another biocompatible polymer chain, thereby linking the two biocompatible polymer chains to each other. The crosslinkers of the present invention can have more than two crosslinking groups.

As used herein, the term "boronic acid crosslinker" refers to a chemical moiety having at least two boronic acid groups that can crosslink biocompatible polymer chains by binding to two adjacent hydroxy groups on the biocompatible polymer chains. The boronic acid crosslinker can also include a linker having a biocompatible polymer (see within). The boronic acid can be any boronic acid species, such as carboxy phenyl boronic acid.

As used herein, the term "Linker" refers to a chemical moiety that links the carboxy phenyl boronic acid groups together. Linkers useful in the present invention have a biocompatible polymer. The term "biocompatible polymer" refers to a polymer that is nontoxic in animals. Examples of biocompatible polymers include, but are not limited to, poly(ethylene glycol), poly(propylene glycol) and others. Polyether polymers useful as crosslinkers include without limitation poly(ethylene glycol) (PEG), poly(propylene glycol) (PPG), poly(propylene glycol) (PPG), alginate, agarose, chitosan, and linear oligosaccharides. The PEG and PPG can be modified with a branching moiety. The term "branching moiety" refers to a chemical moiety that links to the polyether polymer via one functional group, and provides at least two other functional groups for linking to the boronic acid groups. Examples of branching moieties include, but are not limited to, lysine, serine, threonine, tyrosine, and cysteine. Other branching moieties can be a lysine derivative, having a carboxylic acid group and both an alpha and omega amine. Other branching moieties are known to one of skill in the art.

BRIEF DESCRIPTION OF THE DRAWINGS

FIGS. 7A-B illustrate a schematic of using biotin-antibody to tether cell-surface molecules to a PVA-avidin gel. The biotin conjugated primary antibody (biotin-1$^{st}$ antibody) can directly bind to the cell-surface molecule. The biotin conjugated secondary antibody (biotin-second antibody) can bind to a first or primary antibody which directly bind to the cell-surface molecule.

FIGS. 8A-C illustrate a schematic of using various gel compositions and biotin-ligands to tether DGC and VTI on the surface of a myocyte.

FIGS. 9A-F illustrate mechano-chemo-transduction (MCT) from DGC to nNOS and from VTI to eNOS. The upper panels (3D display of confocal images) show that imposing mechanical stress on DGC activated mechano-chemo-transduction to generate $Ca^{2+}$ sparks (A); inhibiting nNOS blocked MCT so there was no sparks (B); inhibiting eNOS did not block MCT so sparks were still present (C). The lower panels (2D display of confocal images) show that imposing mechanical stress on DGC and VTI activated mechano-chemo-transduction to generate $Ca^{2+}$ sparks (D); inhibiting nNOS alone was insufficient to block MCT so sparks were still present (E); inhibiting both nNOS and eNOS blocked MCT so there was no sparks (F). Therefore, DGC pathway activates nNOS whereas VTI pathway activates eNOS.

FIGS. 10A-C illustrate a schematic of a Cell-in-Gel device.

FIGS. 11A-G illustrate mechanical stress effects on $Ca^{2+}$ handling during systole and diastole. (A) Schematic of a myocyte embedded in 3D hydrogel matrix containing red fluorescence beads. (B) Confocal imaging of the myocyte and beads demonstrating cell contraction and gel deformation as seen in the movement of the cell's edge and the red fluorescent beads embedded in gel. (C) Cell contracting in normal Tyrode solution provides load-free control. (D) Cell contracting in-gel under mechanical-load. (E) Fractional shortening of cell contraction in-gel (n=17 Cells) compared with load-free control (n=17). (F) Systolic $Ca^{2+}$ transient (CaT) peak in cell-in-gel (n=17) compared with load-free control (n=17). (G) Diastolic $Ca^{2+}$ spark frequency in the cells for load-free (n=18), in soft gel made of 5% crosslinker (Gel5%, n=9), in gel with 7.5% crosslinker (Gel7.5%, n=18), and after blebbistatin treatment (n=5). One-way ANOVA with Bonferroni post-test was used for pair-wise comparison: P<0.001***.

FIGS. 13A-B illustrate mechanical stress effects on the systolic $Ca^{2+}$ transient and contraction. The myocyte contraction and systolic $Ca^{2+}$ transient (CaT) were measured using Fluo-4 confocal imaging. Shown are (A) the peak CaT and (B) the fractional shortening (FS=% of sarcomere length change) in the myocytes contracting load-free (n=18 cells), in softer gel made of 5% crosslinker (Gel5%, n=9), in harder gel with 7.5% crosslinker (Gel7.5%, n=18), and after blebbistatin treatment (n=5). One-way ANOVA with Bonferroni post-test is used for pair-wise comparison: P<0.05*, P<0.01 P<0.001* deemed significant, and P>0.05 non-significant (NS).

FIGS. 14A-F illustrate mechano-chemo-transduction effects on the systolic $Ca^{2+}$ transient and the SR load in myocyte contraction in-Gel. The temporal response of mechano-chemo-transduction was studied by monitoring the $Ca^{2+}$ signaling in the myocyte before, during, and after pacing. (A) The in-Gel myocyte had very few $Ca^{2+}$ sparks before pacing; then, after an initial delay (insert a), developed a large number of $Ca^{2+}$ sparks during paced contraction (insert b); when pacing stopped the $Ca^{2+}$ sparks cleared out immediately (insert c). (B) The $Ca^{2+}$ spark rate in the myocyte contracting in-gel versus load-free during the pacing protocol. (C) Representative recordings of the $Ca^{2+}$ transient (CaT) in the cell under load-free vs. in-gel contraction measured using Fura-2 ratio ($R_{fura}$). Scale bar: R=0.5, t=2s. (D) The peak systolic $Ca^{2+}$ transient is higher in-gel (n=29 Cells) than load-free (n=19). (E) The SR content was measured by applying caffeine (20 mM) at $\Delta T$=15s after stop of pacing to rapidly release $Ca^{2+}$ from SR. The SR content was similar for the cells in-gel (n=9) and load-free (n=17). (F) The tau of $Ca^{2+}$ transient did not change in-gel (n=29 Cells) from load-free (n=19). The tau of caffeine-induced $Ca^{2+}$ transient decline was longer in-gel (n=9) than load-free (n=17). Unpaired Student's t-test: P<0.05*, P<0.001***.

FIGS. 15A-J illustrate the differential role of nNOS versus eNOS in mechano-chemo-transduction. All data shown are from myocyte contracting in-Gel unless labeled Load-free. (A) $Ca^{2+}$ activities in wild-type (wt) myocyte. Effect of inhibiting (B) eNOS vs (C) nNOS. (D) nNOS$^{-/-}$ myocyte was devoid of $Ca^{2+}$ sparks. (E) eNOS$^{-/-}$ myocyte has frequent $Ca^{2+}$ sparks. (F) Inhibiting nNOS in the eNOS$^{-/-}$ myocyte suppressed sparks. (G) The peak $Ca^{2+}$ transient in wild-type (wt) myocyte contraction in-gel and the effect of inhibiting NOS isoforms. (H) The Mean±SEM values of $Ca^{2+}$ spark rate and the inhibitor effects in wild-type cells for load-free (n=18 cells), in-gel (n=18), and the effect of L-NAME 10 mM (n=9), L-NPA 5 µM (n=9), and L-Nio 10 µM (n=10), respectively. (I) The $Ca^{2+}$ spark rate in nNOS–/– knockout: n=8, 10, 10, 9 cells for each group from left to right. (J) The $Ca^{2+}$ spark rate in eNOS–/– knockout: n=10, 13, 6, 6 cells for each group from left to right. One-way ANOVA with Bonferroni post-test was used for pair-wise comparison: P<0.001***.

FIGS. 16A-C illustrates the effect of inhibiting nNOS or eNOS on myocytes. The $Ca^{2+}$ transient and myocyte contraction were simultaneously measured using Fura-2 ratio (Rfura) and the sarcomere detection method. (A) The peak systolic $Ca^{2+}$ transient (CaT), (B) Tau of the $Ca^{2+}$ transient decline, and (C) fractional shortening contraction (FS=% of sarcomere shortening) in the myocytes contracting load-free (n=22), in-Gel (n=18) and after using L-NPA to inhibit nNOS (n=7) or using L-Nio to inhibit eNOS (n=12). One-Way ANOVA test show significant difference in CaT (p<0.05), Tau (p<0.01), and FS (p<0.001); Bonferroni post-test is used for pair-wise comparison between the in-Gel group and the others: P<0.05*, P<0.01, P<0.001* deemed significantly different with the confidence level of 95%.

FIG. 17A-D illustrate expression and distribution of RyR, nNOS, eNOS in wild-type myocyte. (A) shows sample confocal images acquired with a 60X water immersion objective, NA=1.2, Zoom=10. Super-resolution structured illumination microscopt (SIM) imaging of nNOS (green) and RyR (red) in (B), and eNOS (cyan) and RyR (red) in (C); n=5 for each group. (D) Co-localization of nNOS-RyR and eNOS-RyR pairs is depicted as the overlapping voxel volume (bars). Intermolecular distance between nNOS-RyR and eNOS-RyR shows the histogram (probability density function, PDF) of the nearest neighbor distance (curves). Mann-Whitney test is used to compare the nNOS-RyR distance versus the eNOS-RyR distance histograms, and the difference is found significant with p<0.0001.

FIGS. 19A-C illustrate mechano-chemo-transduction in healthy heart and in cardiomyopathy. (A) Sample images of $Ca^{2+}$ signals in R92Q myocytes during pacing at 1 Hz at body temperature, and the effect of inhibiting nNOS, eNOS, NOX2, or CaMKII. (B) Comparing the $Ca^{2+}$ spark rate in WT versus R92Q myocytes. WT: load-free (n=18 cells), Cell-in-Gel (n=47), and the effect of drugs on Cell-in-Gel: L-NPA 5 µM (n=9), L-Nio 10 µM (n=9), Gp91ds 1 µM (n=31), KN93 1 µM (n=10). R92Q: load-free (n=12), Cellin-Gel (n=20), and the effect of drugs on Cell-in-Gel: L-NPA 5 μM (n=32), L-Nio 10 μM (n=12), Gp91ds 1 μM (n=16), KN93 1 μM (n=23). Two-way ANOVA test show significant difference in the spontaneous $Ca^{2+}$ spark rate between the R92Q versus WT strains (p<0.0001), significant drug effects (p<0.0001), and also significant interaction (p<0.0001). Bonferroni post-test show significant difference for the drug effect compared to Cell-in-Gel without drug (p<0.001***) on each strain; also show significantly higher spark rate in R92Q than WT for Cell-in-Gel condition (p<0.05#) and for Gp91ds effect (p<0.001###). (C) Schematic of mechano-chemo-transduction pathways.

FIGS. 20A-E illustrate PVA-Crosslinker system for embedding single myocyte in 3D elastic matrix. Schematic of a myocyte embedded in 3D PVA hydrogel matrix (Cell-in-Gel). First, the cell (A) was mixed with PVA solution (B); then 4-boronate-PEG crosslinker (C) was added. The boronate crosslinks the cis-diols of the cell surface glycans to the PVA gel, thereby embedding the cell in the PVA gel with the cell surface tethered to the gel (D). (E) This Cell-in-Gel system allows solution exchange by perfusion to study drug effects, electric field stimulation to study myocytes excitation-contraction coupling, and microscopic imaging to study the structure and function of embedded myocytes. Displacement in the gel can be tracked by embedded submicron fluorescent beads.

FIGS. 21A-C illustrate Disrupting the chain-of-command in DGC alters $Ca^{2+}$ signal. (A) Mechanical stress induced Ca2+ sparks when DGC is tethered; (B) Masking a-DG abolished Ca2+ sparks; (C) Dystrophin-null mutation also abolishes $Ca^{2+}$ sparks.

FIGS. 22A-D illustrate that DGC and VTI collectively form costamere to confer mechano-chemo-transduction. Defective DGC unbalances M-C transduction.

DETAILED DESCRIPTION

1. Introduction

Figure 1:
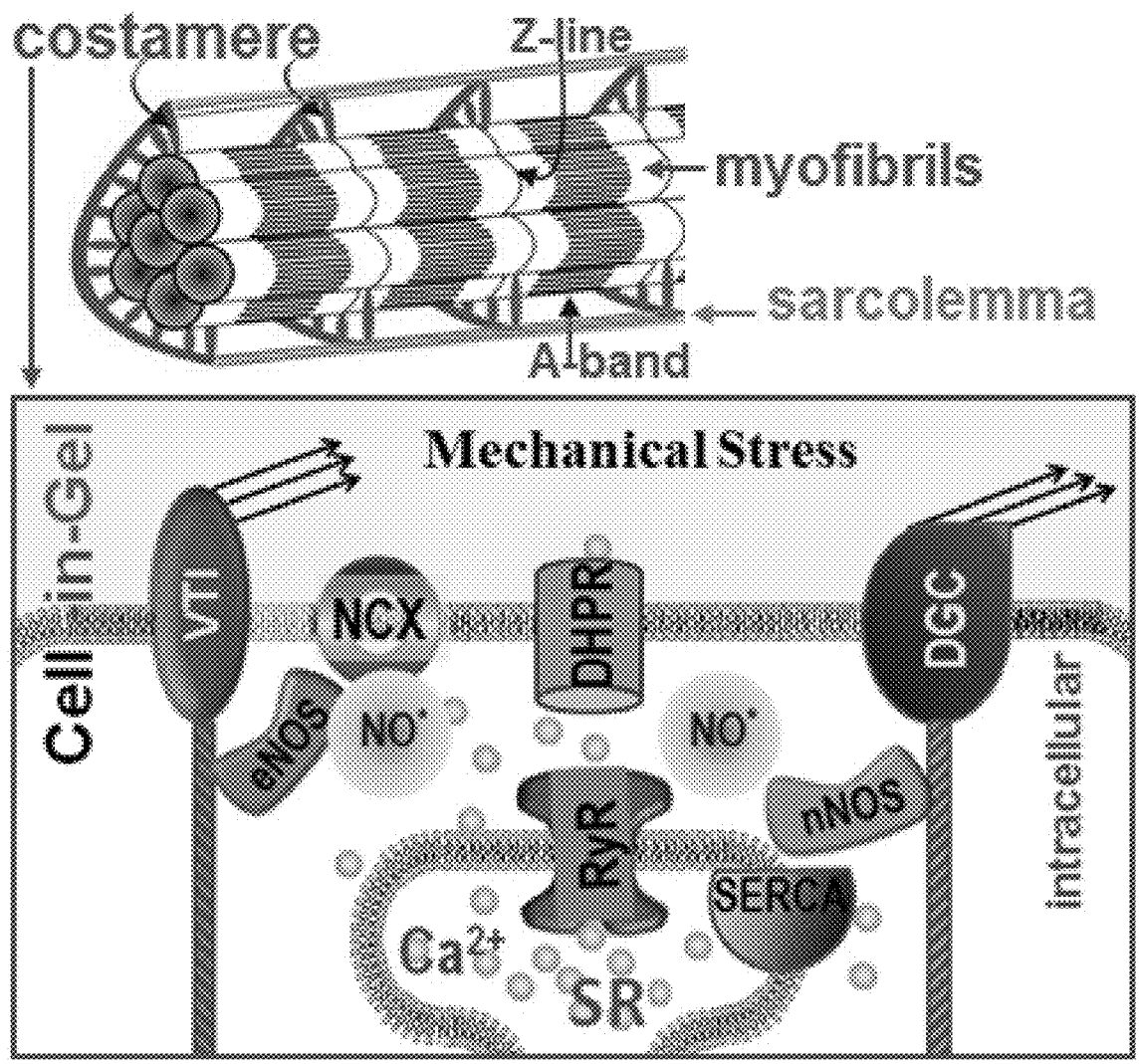
FIG. 1 illustrates a muscle cell structure and the costamere complex (green beams in the upper panel) that encircles the z-line to provide structural support. Costamere comprises dystrophin-glycoprotein complex (DGC) and the vinculin-talin-integrin complex (VTI). Our studies show mechano-chemo-transduction (MCT) pathways from DGC and VTI to nitric oxide synthase 1 (or nNOS) and nitric oxide synthase 3 (or eNOS) and to $Ca^{2+}$ handling proteins.

The compositions, devices, systems, methods and kits described herein enhance the understanding of the mechano-chemo-transduction (MCT) mechanism. They achieve at least two important capabilities: one is to control mechanical stress at the single cell level in 3-D environment mimicking the myocardium; the other is to tug on specific cell-surface mechanosensors during myocyte contraction. These technical capabilities are useful for interrogating the MCT mechanisms at the cellular and molecular levels. In contrast to the present compositions, devices, systems, methods and kits, currently available techniques do not have both capabilities.

Provided herein is a 'Cell-in-Gel' system to embed single live cells, including myocytes, in a 3D elastic gel that mimics the in vivo mechanical environment. This system differs from the currently used techniques in two important ways. First, the cell (e.g., myocyte) contracts against the elastic gel which imposes not only longitudinal tension and transverse compression on the cell but also shear and normal stresses on the cell surface. Second, the Cell-in-Gel system enables tethering of specific mechanosensors on the cell surface (e.g., integrins, glycoproteins) to the gel matrix to interrogate how the MCT complexes transduce mechanical stress to affect intracellular $Ca^{2+}$ dynamics.

Multidisciplinary expertise in synthetic chemistry, muscle mechanics, and cellular and molecular biology have been combined to develop the Cell-in-Gel system and to deploy a set of versatile and easy-to-use tools to control mechanical stress at single cell and molecular levels. Further provided are hardware and software to impose mechanical stress at the single cell and molecular level and to interrogate the mechano-chemo-transduction mechanisms.

We have engineered the present Cell-in-Gel system that allows embedding of live myocytes in 3D elastic hydrogel that mimics the in vivo environment. This system enables controlling the mechanical stress on the single myocyte during contraction and monitoring the cellular and molecular changes in response to various stress levels. For usefulness and versatility, the Cell-in-Gel system has at least the following desirable properties (see, FIG. 20).

(a) The Cell-in-Gel system can be made using known synthetic components (instead of natural products with impure components such as Matrigel or ECM extracts), and thereby provide well-defined chemistry to interrogate the cellular and molecular mechanisms of mechano-chemo-transduction.

(b) The chemical compositions of the gel are non-toxic and non-damaging to the living cells. Isolated cardiac myocytes (and other myocytes) are especially fragile. The chemical components for assembling the gel are non-toxic at physiological pH and temperature. This enables using the Cell-in-Gel system to study the live cell functions.

(c) It is easy and fast (within minutes) to embed cells in the gel to make it feasible for obtaining data from fragile cells in a reasonable time frame (within hours and days).

(d) The stiffness (Young's modulus) of the gel is readily tunable by adjusting the ratio of the gel component and the crosslinker. This enables fine-tuning the level of mechanical stress applied on the cell.

(e) The gel matrix is porous to allow rapid solution exchange and drug application for experimental studies.

(f) The gel is optically transparent to allow imaging on microscopes.

(g) The gel contains versatile 'hooks' that allow tethering of specific cell-surface molecules, which enables controlling the mechanical stress on distinct cell-surface molecules (mechanosensors etc.).

A major hindrance to studying MCT mechanisms is a lack of technology to achieve two important capabilities: one is to control mechanical stress at the single cell level in 3-D environment mimicking the myocardium; the other is to tug on specific cell-surface mechanosensors during myocyte contraction in order to interrogate their role in MCT. However, all currently available techniques fall short of having both capabilities.

The Cell-in-Gel system has at least two major advantages over existing techniques (stretching cells using carbon fibers or glass rods). (1) Live cardiomyocytes are embedded in a 3-D hydrogel (elastic matrix composed of crosslinking polymers) so they experience 3-D mechanical stresses (longitudinal tension, transverse compression, shear stress) during contraction, mimicking the in vivo environment. (2) The gel chemistry allows tethering specific cell-surface mechanosensors (e.g., dystroglycans, integrins) to the gel matrix to impose mechanical stress on them during cell contraction. The Cell-in-Gel system enables the study of mechano-chemo-transduction complexes, their downstream signaling, and functional consequences in live cardiomyocytes and other cell types.

We have used the Cell-in-Gel system to evaluate that two macromolecular complexes in cardiomyocytes-DGC and VTI-transduce mechanical stress to modulate the $Ca^{2+}$ signaling system on a beat-to-beat basis, which enhances $Ca^{2+}$ transient and contractility in response to mechanical load, but this same mechanism can also cause $Ca^{2+}$ dysregulation under excessive load. Resolving this mechanism is important to understanding how the heart responds to mechanical load to auto-regulate contractility, how excessive loads cause heart diseases, and how DGC mutations in muscular dystrophy lead to $Ca^{2+}$ dysregulation and cardiac dysfunction. The Cell-in-Gel system provides a powerful new tool for the research and development of effective drug therapies for treating mechanical stress induced heart diseases.

2. Compositions a. Generally

The hydrogels encapsulating or embedding the cells are generally biocompatible, non-toxic to the cells, do not damage the cells, do not affect cell function and allow cells to perform their natural physiological function. The hydrogels further have chemical moieties that allow binding or tethering of the hydrogel, directly or indirectly (e.g., through a cross-linker), to one or more surface molecules on the cell. In varying embodiments, the hydrogels are functionalized with a first or second binding partner of a binding partner pair molecules. The first or second binding partner of the binding partner pair can be bound or attached to the encapsulated cell directly or indirectly (e.g., through the complementing partner of the binding partner pair (e.g., first binding partner is complementing to second binding partner and second binding partner is complementing to first binding partner) or a ligand conjugate with the complementing binding partner, wherein the ligand binds to a cell surface molecule). When functionalized with a first or second binding partner of the binding partner pair, the binding partner molecules also can be linked to each other in the hydrogel, e.g., via a Y—X—Y crosslinker, wherein X is a hydrophilic linear polymer (e.g., polyethylene glycol (PEG), poly(propylene glycol) (PPG), alginate, agarose, chitosan, and linear oligosaccharides) and Y is a first or second binding partner of the binding partner pair. The 3D hydrogels have a stiffness that mimics the in vivo mechanical environment and allows for measuring the strain and stress imposes on a cell tethered or attached to the hydrogel.

b. Binding Partner Pairs

Any binding partner pair known in the art can be used in the compositions described herein. In varying embodiments, the binding partner pair is selected from the group consisting of avidin/biotin, glutathione/glutathione S-transferases (GST), maltose-binding protein (MBP)/maltose, Histag/Imidazole plus Zn2+, and vancomycin/D-alanine-D-alanine (DADA), wherein either member of the binding partner pair can be the first binding partner or the second binding partner. In some embodiments, the avidin is selected from avidin, streptavidin, neutravidin, captavidin, and mixtures thereof. In varying embodiments, the vancomycin and the D alanine-D-alanine (DADA) are monovalent, divalent or trivalent.

c. Polymer

In varying embodiments, the hydrogel has a matrix constructed by a biocompatible polymer. Generally, biocompatible polymers useful are those that are non-toxic to animals, particularly mammals, particularly to the one or more cells encapsulated or embedded in the gel. Illustrative of biocompatible polymers include agarose, alginate, polyvinyl alcohols (PVA), polyethers such as poly(ethylene glycol) and poly(propylene glycol), as well as cellulose, polysaccharides, and polyesters.

In varying embodiments, the polymer has chemical moieties that allow for tethering or attaching to encapsulated cells and/or intracrosslinking of the polymer molecules that comprise the hydrogel. Biocompatible polymers having any functional moieties useful for covalent bonding or chemical crosslinking find use. In varying embodiments, the functional moiety is a hydroxyl, a diol (e.g., cis-diol), a carboxyl group, an amino group, an amino-oxy group, an azide, or an alkyne. In varying embodiments, the biocompatible polymer molecules have an average molecular weight in the range of about 50-150 kDa, e.g., about 80-100 kDa, e.g., about 50 kDa, 60 kDa, 70 kDa, 80 kDa, 90 kDa, 100 kDa, 110 kDa, 120 kDa, 130 kDa, 140 kDa or 150 kDa. Illustrative polymers and cell adhesion matrices of use include polyvinyl alcohols (PVA), polymers described in Int. Publication No. WO 2010/148346, agarose and alginate. Int. Publication No. WO 2010/148346 is hereby incorporated herein by reference in its entirety for all purposes.

For embodiments employing polyvinyl alcohols (PVA), poly(vinyl alcohol) chains used in the hydrogel can be any suitable size. For example, in varying embodiments, the poly(vinyl alcohol) chains have an average molecular weight of from about 500 to about 150,000, or from about 50,000 to about 150,000, or from about 75,000 to about 125,000, or from about 85,000 to about 105,000.

d. Crosslinker

The hydrogels generally contain crosslinker molecules. Any biocompatible crosslinker molecules find use. In varying embodiments, the crosslinker is bivalent, trivalent or tetravalent.

In varying embodiments, the crosslinker molecules link polymer molecules to polymer molecules and/or link or tether polymer molecules to the embedded or encapsulated cells. Polymer molecules can be linked through the attached first or second binding partners of a binding partner pair or through other available chemical functional groups. In varying embodiments, first or second binding partners of the binding partner pair attached to the polymer are linked via a Y—X—Y crosslinker, wherein X is a linear hydrophilic polymer and Y is the complementing binding partner of the binding partner pair. In varying embodiments, avidin molecules on the polymer are linked via a biotin-X-biotin crosslinker, wherein X is a linear hydrophilic polymer. In varying embodiments, biotin molecules on the polymer are linked via an avidin-X-avidin crosslinker, wherein X is a linear hydrophilic polymer. A polymer having hydroxyl or diol functional groups can be cross-linked with a boronate-X-boronate crosslinker, wherein X is a linear hydrophilic polymer. In some embodiments, the boronate in the boronate-X-boronate crosslinker is selected from the group consisting of diboronate, triboronate, tetraboronate, and mixtures thereof.

In varying embodiments, X refers to a linear hydrophilic polymer selected from polyethylene glycol (PEG), poly(propylene glycol) (PPG), alginate, agarose, chitosan, and linear oligosaccharides. Crosslinking polymers of use are discussed, e.g., in Song, et al, *Bioorganic & Medicinal Chemistry Letters* 14 (2004) 161-165, which is hereby incorporated herein by reference in its entirety for all purposes. In varying embodiments, the crosslinker comprises a molecular weight in the range of about 1-50 kDa, e.g., about 10-30 kDa, e.g., about 15-25 kDa, e.g., about 5 kDa, 10 kDa, 15 kDa, 20 kDa, 25 kDa, 30 kDa, 35 kDa, 40 kDa, 45 kDa or 50 kDa. Useful poly(ethylene glycol) polymers can be any suitable size. For example, the poly(ethylene glycol) polymer can have a molecular weight of from about 500 to about 50,000, or from about 500 to about 5,000, or from about 1,500 to about 2,500. Other poly(ethylene glycol) polymers are useful, including those described in WO 2010/148346.

In varying embodiments, ligand conjugates of the first or second binding partner of the binding partner pair can be used to tether cell surface molecules specifically bound by the ligand on the surface of a cell to complementing binding partners conjugated to the polymer. In varying embodiments, biotin-ligand conjugates can be used to tether cell surface molecules specifically bound by the ligand on the surface of a cell to avidin molecules conjugated to the polymer. In varying embodiments, avidin-ligand conjugates can be used to tether cell surface molecules specifically bound by the ligand on the surface of a cell to biotin molecules conjugated to the polymer.

The stiffness of the gel is tunable by adjusting the mixing ratio of the crosslinker and PVA. In varying embodiments, the wt./wt. ratio of the polymer:crosslinker is in the range of about 0.1 to about 10. In varying embodiments, e.g., when the cell is a myocyte, the wt./wt. ratio of the polymer:crosslinker is in the range of about 0.5 to about 5. A hydrogel with a relatively higher proportion or concentration of crosslinker will have a relatively higher stiffness or Young's modulus value. In varying embodiments, the hydrogel has a stiffness or Young's modulus value in the range of about 0.5 kPa to about 100 kPa. Stiffness in cardiac tissue can increase to 100 kPa or more under pathological conditions such as fibrosis and infarction.

e. Ligand

The ligand of the ligand conjugates with the first or second binding partner of the binding partner pair is generally a ligand that binds to a cell surface molecule, to allow tethering of selected cell surface molecules to the hydrogel. In varying embodiments, the ligand is selected from a polypeptide, a linear peptide, a circularized peptide, a peptidomimetic, an antigen binding molecule (e.g., nanobodies, Adnectins, Avimers, Anticalins, antibody mimics, etc.), an antibody, an antibody fragment (e.g., Fab fragments, Fab' fragments, Fab'-SH fragments, F(ab')2 fragments, Fd fragments, Fv fragments, diabodies, single-chain Fv (scFv) molecules, single-chain polypeptides containing only one light chain variable domain, single-chain polypeptides containing the three CDRs of the light-chain variable domain, single-chain polypeptides containing only one heavy chain variable region, and single-chain polypeptides containing the three CDRs of the heavy chain variable region), a carbohydrate or any other molecule that binds to the surface of the cell. In varying embodiments, the ligand binds to an integrin, a glycoprotein or a glycan. For example, the ligand may bind to an integrin selected from the group consisting of an $\alpha 3\beta 1$ integrin, an $\alpha 4\beta 1$ integrin, and an $\alpha v\beta 3$ integrin. In some embodiments, the ligand is a polypeptide selected from the group consisting of collagen, laminin, fibronectin, fibrinogen, vitronectin, VCAM-1, and cadherin, and subsequences thereof.

In varying embodiments, the ligand is an antibody that binds to a cell surface molecule. In varying embodiments, the ligand in the conjugate with the first or second binding partner of the binding partner pair is a secondary antibody that binds to a primary antibody that binds to or is bound to a cell surface molecule on the cell.

In varying embodiments, the ligand is a peptide that binds to an integrin. In some embodiments, the ligand can be a cell adhesion ligand such as a peptide, protein, peptidomimetic or antibody, or a reporter substrate such as a fluorescent substrate. Examples of useful cell adhesion ligands include without limitation RGD ligands, LXY3, MSE, HYD1 and LLP-2A. These ligands, and others useful in the present invention, bind to various integrin types, including $\alpha_6\beta_1$, $\alpha_3\beta_1$, $\alpha_4\beta_1$, $\alpha_3\beta_1$, $\alpha_v\beta_3$, $\alpha_1$, $\alpha_2$, among others. Further illustrative peptides that find use are described, e.g., in Xiao, et al., *Molecular Cancer Therapeutics*. (2010) 9:2714-23; Yao, et al., *Journal of Medicinal Chemistry*. (2009) 52:126-33; Peng, et al., *Nat Chem Biol*. (2006) 2:381-9; Pennington, et al., *Molecular Diversity* (1996) 2: 19-28; DeRoock, et al., *Cancer Research*, (2001) 61:3308-3313; Park, et al., *Letters in Peptide Science*, (2002) 8:171-178; Aina, et al., *Molecular Cancer Therapeutics*, (2005) 4: 806-813; Aina, et al., *Molecular Imaging*, (2005) 4: 439-447; Liu, *Biopolymers (Peptide Science)* (2006) 84: 595-604; Carpenter, et al., *Journal of Combinatorial Chemistry*, (2006) 8: 907-914; Aina, et al., *Molecular Pharm*. (2007) 4:631-651, 2007; Carpenter, et al., *J Medicinal Chemistry*. (2007) 50: 5863-5867; Peng, et al., *Molecular Cancer Therapeutics*. (2008) 7:432-437; Luo, et al., *Journal of Combinatorial Chemistry*, (2008) 10:599-604; Xiao, et al., *European Journal of Nuclear Medicine and Molecular Imaging*, (2008) 36: 94-103; Yao, et al., *J Med Chem* (2009) 52: 126-133; Yao, et al., *J Med Chem*. 52:6744-6751; Carpenter, et al., *Cancer Research*. (2010) 70: 5448-556; Zhang, et al., *Urol Oncol*. (2012) 30(5):635-45; Aina, et al., *Vet Immunol Immunopathol*. (2011) 143:11-19; Zwingenberger, et al., *Vet Immunol Immunopathol*. (2012) 145: 298-304; Zwingenberger, et al., *PLos One*, (2012) 7(4):e34404; and Lin, et al., Int J Nanomedicine. (2012) 7:2793-804. All of the foregoing listed publications are hereby incorporated herein by reference in their entirety for all purposes.

3. Methods of Making Cell-in-Gel Compositions

Further provided are methods of encapsulating and tethering a cell to a hydrogel, such that the cell retains viability and functionality (e.g., signaling through cell surface receptors, contractility).

In one embodiment, cell-surface proteins (e.g., integrins) are tethered to a hydrogel without tethering the glycans. In varying embodiments, the method entails: (1) binding ligand conjugates with the first or second binding partner of the binding partner pair to the cell, wherein the ligand conjugates bind to the binding partner of the ligand, (2) binding ligand-conjugates of the first binding partner or the second binding partner with the complementing binding partner of the binding partner pair and, (3) crosslinking the first or second binding partner with a Y—X—Y crosslinker, wherein X is a hydrophilic linear polymer (e.g., polyethylene glycol (PEG), poly(propylene glycol) (PPG), alginate, agarose, chitosan, and linear oligosaccharides), and Y is the complementing binding partner. In varying embodiments, the method entails: (1) binding biotin-ligand conjugates to the cell, wherein the biotin-ligand conjugates bind to the ligand binding partner of the ligand, (2) binding avidin molecules to the biotin-ligand conjugates and, (3) crosslinking the avidin molecules with a biotin-X-biotin crosslinker, wherein X is a hydrophilic linear polymer (e.g., polyethylene glycol (PEG), poly(propylene glycol) (PPG), alginate, agarose, chitosan, and linear oligosaccharides). In varying embodiments, the method entails: (1) binding avidin-ligand conjugates to the cell, wherein the avidin-ligand conjugates bind to the ligand binding partner of the ligand, (2) binding biotin molecules to the avidin-ligand conjugates and, (3) crosslinking the biotin molecules with an avidin-X-avidin crosslinker, wherein X is a hydrophilic linear polymer (e.g., polyethylene glycol (PEG), poly(propylene glycol) (PPG), alginate, agarose, chitosan, and linear oligosaccharides).

In varying embodiments, creating a cell-in-gel of the above configuration entails the following steps:

(a) contacting cells (e.g., myocytes) with a ligand conjugate with a first or second binding partner of a binding partner pair under conditions sufficient for the first binding partner to bind to the ligand binding partner of the ligand on the surface of the cell;

(b) contacting the cells bound to the ligand conjugate with the first or second binding partner with the complementing binding partner under conditions allowing the complementing binding partner to bind to the biotin of the ligand conjugate with the first or second binding partner;

(c) contacting the complexes comprised of first binding partner/second binding partner-ligand conjugate/cells with a Y—X—Y crosslinker, wherein X is a hydrophilic linear polymer (e.g., polyethylene glycol (PEG), poly(propylene glycol) (PPG), alginate, agarose, chitosan, and linear oligosaccharides), and Y is the second binding partner, under conditions sufficient for the Y—X—Y crosslinker to cross link the first binding partner and form a hydrogel with the single cells (e.g., myocytes) embedded in the gel matrix, and with the cell-surface ligand binding partner tethered to the gel of the first binding partner.

In varying embodiments, creating a cell-in-gel of the above configuration entails the following steps:

(a) contacting cells (e.g., myocytes) with a biotin-ligand conjugate under conditions sufficient for the biotin-ligand to bind to the ligand binding partner of the ligand on the surface of the cell;

(b) contacting the cells bound to the biotin-ligand conjugate with avidin under conditions allowing the avidin to bind to the biotin of the biotin-ligand conjugate;

(c) contacting the complexes comprised of avidin/biotin-ligand conjugate/cells with a biotin-X-biotin crosslinker, wherein X is a hydrophilic linear polymer (e.g., polyethylene glycol (PEG), poly(propylene glycol) (PPG), alginate, agarose, chitosan, and linear oligosaccharides), under conditions sufficient for the biotin-X-biotin crosslinker to cross link the avidin and form a hydrogel with the single cells (e.g., myocytes) embedded in the gel matrix, and with the cell-surface ligand binding partner tethered to the avidin gel.

In varying embodiments, creating a cell-in-gel of the above configuration entails the following steps:

(a) contacting cells (e.g., myocytes) with a biotin-ligand conjugate under conditions sufficient for the biotin-ligand to bind to the ligand binding partner of the ligand on the surface of the cell;

(b) contacting the cells bound to the biotin-ligand conjugate with avidin under conditions allowing the avidin to bind to the biotin of the biotin-ligand conjugate;

(c) contacting the complexes comprised of avidin/biotin-ligand conjugate/cells with a biotin-X-biotin crosslinker, wherein X is a hydrophilic linear polymer (e.g., polyethylene glycol (PEG), poly(propylene glycol) (PPG), alginate, agarose, chitosan, and linear oligosaccharides), under conditions sufficient for the biotin-X-biotin crosslinker to cross link the avidin and form a hydrogel with the single cells (e.g., myocytes) embedded in the gel matrix, and with the cell-surface ligand binding partner tethered to the avidin gel.

In varying embodiments, creating a cell-in-gel of the above configuration entails the following steps:

(a) contacting cells (e.g., myocytes) with an avidin-ligand conjugate under conditions sufficient for the avidin-ligand to bind to the ligand binding partner of the ligand on the surface of the cell;

(b) contacting the cells bound to the avidin-ligand conjugate with biotin under conditions allowing the biotin to bind to the biotin of the avidin-ligand conjugate;

(c) contacting the complexes comprised of biotin/avidin-ligand conjugate/cells with an avidin-X-avidin crosslinker, wherein X is a hydrophilic linear polymer (e.g., polyethylene glycol (PEG), poly(propylene glycol) (PPG), alginate, agarose, chitosan, and linear oligosaccharides), under conditions sufficient for the avidin-X-avidin crosslinker to cross link the biotin and form a hydrogel with the single cells (e.g., myocytes) embedded in the gel matrix, and with the cell-surface ligand binding partner tethered to the biotin gel.

Generally, the hydrogels comprises of cross-linked binding partner of binding partner pairs do not tether the cell-surface glycans, and thus can be used to selectively tether desired cell-surface molecules (e.g., that are not glycans), depending on the ligand binding partner bound by the ligand conjugate with the first or second binding partner employed. In the above embodiment, the Avidin-Biotin hydrogel does not tether the cell-surface glycans, and thus can be used to selectively tether desired cell-surface molecules (e.g., that are not glycans), depending on the ligand binding partner bound by the biotin-ligand conjugate or the avidin-ligand conjugate employed. Avidin has four biotin binding sites. Therefore, when avidin is mixed with biotin-X-biotin crosslinker or when biotin is mixed with an avidin-X-avidin crosslinker, a gel matrix is formed. When biotin-ligand conjugate or avidin-ligand conjugate is added to the preformed gel, the ligand conjugate will link avidin or biotin molecules, respectively, to display the ligand on the gel matrix. Alternatively, avidin, the biotin-X-biotin crosslinker and biotin-ligand conjugate can all be mixed together concurrently to form a gel decorated with ligand. Similarly, biotin, an avidin-X-avidin crosslinker and avidin-ligand conjugate can all be mixed together concurrently to form a gel decorated with ligand. In another embodiment outlined below, avidin or biotin can also be covalently linked to a biocompatible polymer (e.g., a polyvinyl alcohol). In that case, the biocompatible polymer serves as the tridimensional gel matrix backbone together with the biotin-X-biotin or avidin-X-avidin crosslinker. The hydrogel properties can be readily adjusted and tuned by mixing various ratios of biocompatible polymer (if included), crosslinker and avidin (or biotin).

In a related embodiment, both cell-surface proteins (e.g., integrins) and cell-surface glycans are tethered to a polymer-first or second binding partner-boronate hydrogel. The polymer-first or second binding partner-boronate hydrogel comprises: (1) biocompatible polymer conjugated to a first binding partner, (2) a boronate crosslinker, and (3) a second binding partner-ligand conjugate.

In varying embodiments, creating a cell-in-gel of the above configuration entails the following steps:

(a) contacting cells (e.g., myocytes) with a ligand conjugate with the first or second binding partner under conditions sufficient for the binding partner-ligand to bind to the binding partner of the ligand on the surface of the cell;

(b) contacting the cells bound to the second binding partner-ligand conjugate with a polymer-first binding partner conjugate under conditions sufficient to allow the first binding partner to bind to the second binding partner of the second binding partner-ligand conjugate;

(c) contacting the complexes comprised of polymer-first binding partner/second binding partner-ligand conjugate/cells with a boronate-X-boronate crosslinker, wherein X is a hydrophilic linear polymer (e.g., polyethylene glycol (PEG), poly(propylene glycol) (PPG), alginate, agarose, chitosan, and linear oligosaccharides), under conditions sufficient for the boronate-X-boronate crosslinker to cross link the polymer and the cells and form a hydrogel with the single cells (e.g., myocytes) embedded in the gel matrix, and with the cell-surface ligand binding partner tethered to the polymer-first binding partner.

In varying embodiments, creating a cell-in-gel of the above configuration entails the following steps:

(a) contacting cells (e.g., myocytes) with the biotin-ligand conjugate under conditions sufficient for the biotin-ligand to bind to the ligand binding partner of the ligand on the surface of the cell;

(b) contacting the cells bound to the biotin-ligand conjugate with a polymer-avidin conjugate under conditions sufficient to allow the avidin to bind to the biotin of the biotin-ligand conjugate;

(c) contacting the complexes comprised of polymer-avidin/biotin-ligand conjugate/cells with a boronate-X-boronate crosslinker, wherein X is a hydrophilic linear polymer (e.g., polyethylene glycol (PEG), poly(propylene glycol) (PPG), alginate, agarose, chitosan, and linear oligosaccharides), under conditions sufficient for the boronate-X-boronate crosslinker to cross link the polymer and the cells and form a hydrogel with the single cells (e.g., myocytes) embedded in the gel matrix, and with the cell-surface ligand binding partner tethered to the polymer-avidin.

In varying embodiments, creating a cell-in-gel of the above configuration entails the following steps:

(a) contacting cells (e.g., myocytes) with the avidin-ligand conjugate under conditions sufficient for the biotin-ligand to bind to the ligand binding partner of the ligand on the surface of the cell;

(b) contacting the cells bound to the avidin-ligand conjugate with a polymer-biotin conjugate under conditions sufficient to allow the biotin to bind to the avidin of the avidin-ligand conjugate;

(c) contacting the complexes comprised of polymer-biotin/avidin-ligand conjugate/cells with a boronate-X-boronate crosslinker, wherein X is a hydrophilic linear polymer (e.g., polyethylene glycol (PEG), poly(propylene glycol) (PPG), alginate, agarose, chitosan, and linear oligosaccharides), under conditions sufficient for the boronate-X-boronate crosslinker to cross link the polymer and the cells and form a hydrogel with the single cells (e.g., myocytes) embedded in the gel matrix, and with the cell-surface ligand binding partner tethered to the polymer-biotin.

In varying embodiments, the cells are suspended in a physiological saline (e.g., standard phosphate buffered saline or Tyrode solution) with pH in the range of $7.2<pH<7.4$ and incubated with the biotin-ligand for about 20-30 minutes at a temperature in the range of 4-37° C. (e.g., at room temperature of 20-25° C. or body temperature of 36-37° C.).

Boronate (e.g., bivalent, trivalent and/or tetravalent) spontaneously binds to the functional (e.g., diol) groups in polymer-avidin or polymer-biotin to form hydrogel with the single cells (e.g., myocytes) embedded in the gel matrix. The cell-surface glycans are also tethered to the gel through boronate binding to the cis-diols in the glycans and the polymer. The cell-surface proteins (e.g., integrins) or any other molecules can be tethered to the gel through biotin-ligand or avidin-ligand binding to the avidin or biotin 'hooks' in the gel, respectively. Hence the polymer-avidin-boronate hydrogel with avidin hooks or the polymer-biotin-boronate hydrogel with biotin hooks provides a versatile system for tethering any cell-surface molecules individually or collectively.

The ligand of the biotin-ligand or the avidin-ligand conjugate can be chosen to bind to any cell-surface molecules of interest. In varying embodiments, the cell surface ligand binding partner is an integrin. Different integrins bind to different adhesion partners in the extracellular matrix. Hence, the biotin-ligand conjugates and the avidin-ligand conjugates can serve as a surrogate to the adhesion molecules in the extracellular matrix.

4. Devices, Systems and Kits a. Devices

Further provided are devices that comprise the compositions described above and herein. In varying embodiments, the device comprises one or more cell-in-gel capsules in one or more perfusion chambers. The one or more perfusion chambers are perfused with a biocompatible, isotonic solution appropriate to the encapsulated or embedded cell and are in fluid communication with one another. In varying embodiments, for example when the encapsulated or embedded cell is a myocyte, the cell-in-gel capsule in the perfusion chamber is perfused with a modified Tyrode solution comprising pyruvic acid substituted for glucose. In varying embodiments, the modified Tyrode solution comprises a $Ca^{2+}$ concentration that is less than 50 µM, which allowed for a relaxed myocyte. Generally, the entire surface of the cell is encapsulated or embedded in the hydrogel, such that no external surface of the cell is in contact with a solid surface of the device (e.g., the inner sides of the perfusion chamber) or another cell within the hydrogel.

In varying embodiments, a mounting-grip is used to mount the cell-in-gel capsule onto the device, e.g., as illustrated in FIG. 10. The mounting-grip can be a comb-grip embedded in the gel, or an elastic membrane around the gel capsule. When used to pull the gel, the comb-grips in the gel allow nearly uniform strain fields across the gel. In varying embodiments, the cell-in-gel capsule is tethered in at least two directions, e.g., in two, four or six directions, e.g., along the x, y and/or z axes. As appropriate, the cell-in-gel capsule can be grabbed by the mounting-grip and then mounted between a micro-manipulator and a force transducer. The mechanical load on the cell-in-gel capsule is controlled by the micromanipulator and monitored by the force transducer. Accordingly, in varying embodiments, the device comprises mounting-grips that can pull on the gel, thereby introducing mechanical strain and/or stress on the gel and the cell encapsulated in the gel.

In varying embodiments, the gel is within an electric field controlled by an electrical stimulator that applies electrical signals to the one or more cells encapsulated in the gel. In varying embodiments, the device may further include an imaging system (e.g., for capturing cellular images) and/or a computer (e.g., for recording mechanical strain and stress imposed on the cell and the gel and/or for recording cellular images).

b. Systems

In varying embodiments, multiple devices in fluid communication with one another can be scaled up to build a high throughput screening system (e.g., of test compounds, e.g., pharmaceuticals) to search for new drugs that affect the myocytes mechano-chemo-transduction. In varying embodiments, the high throughput cell-in-gel system contains the following components.

(a) An array of two or more, e.g., 6, 8, 24, 48, 96, 192, 384 cell-in-gel capsules in fluid communication. In varying embodiments, the array can be in a 1-dimensional (e.g., linear) or a 2-dimensional arrangement.

(b) One or more perfusion channels through each cell-in-gel capsule;

(c) Optionally, an electrical stimulator (e.g., to pace the myocytes in-gel to undergo excitation-$Ca^{2+}$ signaling-contraction);

(d) Optionally, an imaging system equipped with an excitation light source, optical filters, and emission light detectors.

(e) Optionally, an analog-digital converter and a computer to record the imaging data; and/or (f) Optionally, a computer, which can be useful to control test compound perfusion of cell-in-gel capsule, data acquisition, image storage, and data analysis.

Accordingly, further provided are systems comprising the compositions and/or devices described herein. In varying embodiments, the systems comprise:

i) One or more perfusion chambers, each perfusion chamber comprising the composition comprising a cell-in-gel capsule as described herein. In varying embodiments, the one or more perfusion chambers are in fluid communication. In varying embodiments, the perfusion solution comprises a modified Tyrode solution, as described herein.

ii) First and second mounting-grips in contact with the gel, wherein the first and second grips can introduce tension on the gel in at least two dimensions. In varying embodiments, the first and second grips introduce tension in diametrically opposing directions.

iii) A computer in communication with the force transducer, wherein the computer can store the mechanical tension readings sensed by the force transducer. In varying embodiments, the computer is programmed to control and/or govern administration of a test stimulus to the perfusion chamber.

iv) Optionally, an imaging system that can capture images of the cell encapsulated in the gel, wherein the imaging system is in communication with one or both of the force transducer and the computer.

v) Optionally, an electrical stimulator that applies electrical signals to the cell encapsulated in the gel.

c. Kits

Further provided are kits. In varying embodiments, components for assembling a cell-in-gel compositions can be packaged from components provided in a kit. In one contemplated embodiment, the kit comprises: i) a solution comprising a biocompatible polymer conjugated to a first binding partner of a binding partner pair; and ii) a solution comprising a Y—X—Y crosslinker; wherein X is a linear hydrophilic polymer, and Y is a second binding partner of a binding partner pair. In one contemplated embodiment, the kit comprises: i) a solution comprising a biocompatible polymer conjugated to avidin; and ii) a solution comprising a biotin-X-biotin crosslinker; wherein X is a linear hydrophilic polymer. In one contemplated embodiment, the kit comprises: i) a solution comprising a biocompatible polymer conjugated to biotin; and ii) a solution comprising an avidin-X-avidin crosslinker; wherein X is a linear hydrophilic polymer. In varying embodiments, the kit further comprises a solution comprising a biotin-ligand conjugate or an avidin-ligand conjugate. Further embodiments of the polymer, avidin, biotin, crosslinker, biotin-ligand conjugate and avidin-ligand conjugate are as described above and herein. The components of this kit are useful to encapsulate or embed and tether cell-surface glycans and as well as any other cell surface molecules.

In one contemplated embodiment, the kit comprises: i) a solution comprising a biocompatible polymer conjugated to avidin; and ii) a solution comprising a boronate-X-boronate crosslinker; wherein X is a linear hydrophilic polymer. In one contemplated embodiment, the kit comprises: i) a solution comprising a biocompatible polymer conjugated to biotin; and ii) a solution comprising a boronate-X-boronate crosslinker; wherein X is a linear hydrophilic polymer. In varying embodiments, the kit further comprises a solution comprising a biotin-ligand conjugate or an avidin-ligand conjugate. Further embodiments of the polymer, avidin, biotin, crosslinker, biotin-ligand conjugate and avidin-ligand conjugate are as described above and herein. The components of this kit are useful to tether any cell-surface molecule without tethering glycans.

The kits can further contain instructions for assembly and use of the cell-in-gel compositions.

Methods of Measuring Cellular Mechanical Strain and Stress

Further provided are methods of monitoring and measuring mechanical strain and/or stress on a cell, comprising:
a) encapsulating a cell in a composition as described above and herein;
b) obtaining a first measurement of the mechanical strain and/or stress on the cell;
c) exposing the cell to a test stimulus;
d) obtaining a second measurement of the mechanical strain and/or stress on the cell; and
e) comparing the first and second measurements.

In varying embodiments, mechanical strain and/or stress can be imposed on the gel prior to and/or after exposing the cell to the test stimulus. One technique for introducing mechanical strain and/or stress on the gel is to pull on the gel, e.g., using a mounting-grip as described herein. The comb grips in the gel allow material to draw inward and translate a bit, a way to get nearly uniform strain fields across the gel. As appropriate or desired, the gel can be pulled in one, two, three, four, five or six directions, simultaneously or sequentially. The Cell-in-Gel capsule can be grabbed by the Comb-Grip and then mounted between a micro-manipulator and a force transducer. The mechanical load on the Cell-in-Gel capsule is controlled by the micro-manipulator and monitored by the force transducer. Mechanical preload on the cell can be imposed by using the micromanipulator to stretch the Cell-in-Gel capsule; the preload level is controlled by the extent of stretching or pulling on the gel. Mechanical afterload on the cell can be imposed by using electrical field to stimulate myocyte contraction in the Cell-in-Gel capsule; the afterload level is controlled by the stiffness of the gel. Combining the stretching with contraction imposes both the preload and the afterload on the cell. Hence this system allows controlling the mechanical preload and the afterload on the single cell.

In varying embodiments, the mechanical strain and/or stress is measured on a myocyte, e.g., a cardiac myocyte, a skeletal muscle myocyte or a smooth muscle myocyte. In varying embodiments, myocyte contraction is measured. In varying embodiments, the test stimulus is physical, chemical or pharmacological. In varying embodiments, the first and/or second measurements of mechanical strain and/or stress on the cell are recorded in a computer readable medium.

The mechanical strain and/or stress on a cell can be measured and quantified using known methods in the art. One such method involves using mathematical modeling of a 3D Cell-in-Gel system and is described in Shaw, et al., PLoS One. (2013) 8(10):e75492).

EXAMPLES

The following examples are offered to illustrate, but not to limit the claimed invention.

Example 1

Figure 3:
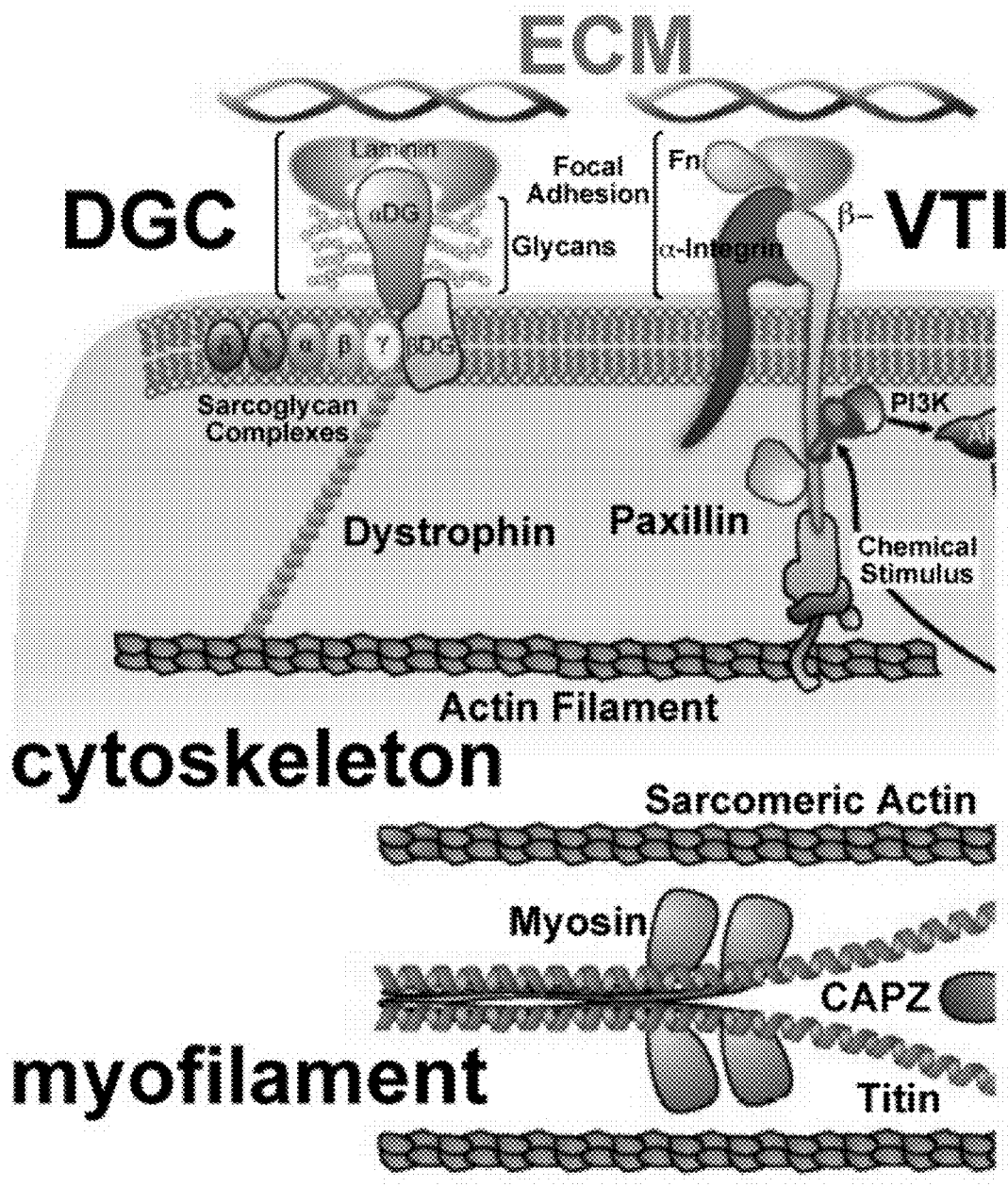
FIG. 3 illustrates DGC and VTI complex in a costamere (modified from Guo et al., (2011) *Journal of Molecular and Cellular Cardiology.* 50:606-12).

Cell-in-Gel System for Embedding Cells in 3D Elastic Matrix and Tethering Cell-surface Molecules 1.1 Design of the Gel Composition to Tether Different Types of Cell-surface Molecules In vivo, the cell surface is adhered to the extracellular matrix (ECM). Mechanosensors on the cell-surface are normally attached to their adhesion partners in the extracellular matrix. In cardiac myocytes, for example, the costamere that encircles the z-disks to provide structural support is composed of the dystrophin-glycoprotein complex (DGC) and the vinculin-talin-integrin complex (VTI). As depicted in FIG. 3, the cell-surface molecules in the DGC are dystroglycans and sarcoglycans (which link to laminin and collagen in the extracellular matrix); the cell-surface molecules in the VTI are integrins (which link to fibronectin, fibrinogen, vitronectin etc. in the extracellular matrix) (Guo, et al., *Journal of Molecular and Cellular Cardiology*. (2011) 50:606-12; Campbell, Cell. (1995) 80:675-9; and Anastasi, *Int J Mol Med*. (2009) 23:149-59). These cell-surface molecules serve as the structural link between the extracellular matrix and the intracellular cytoskeleton (and also myofilament in the case of muscle cells). These cell-surface molecules also serve as mechanosensors to activate the mechano-chemo-transduction through their macro-molecular complexes and downstream signaling pathways.

We have designed the gel compositions to tether different types of cell-surface molecules, which enables imposing mechanical stress on specific molecules to investigate their response to mechanical stress and the down-stream mechano-chemo-transduction mechanisms. Herein we describe three different gel compositions for tethering various cell-surface molecules including glycans, integrins, and any other molecules in general.

1.2 the PVA-Boronate Gel Composition for Tethering Cell-surface Glycans

The basic PVA-Boronate Gel composition for tethering the cell-surface glycans is described in Int. Publication No. WO 2010/148346. Although this gel was originally designed to support cancer cell growth in 3D scaffolding, its chemistry can also be used to bind glycans to the PVA gel. Hence we adapted it to embed cells, including cardiac myocytes, in the gel and tether the cell-surface glycans (e.g., dystroglycans, sarcoglycans of DGC).

Figure 4:
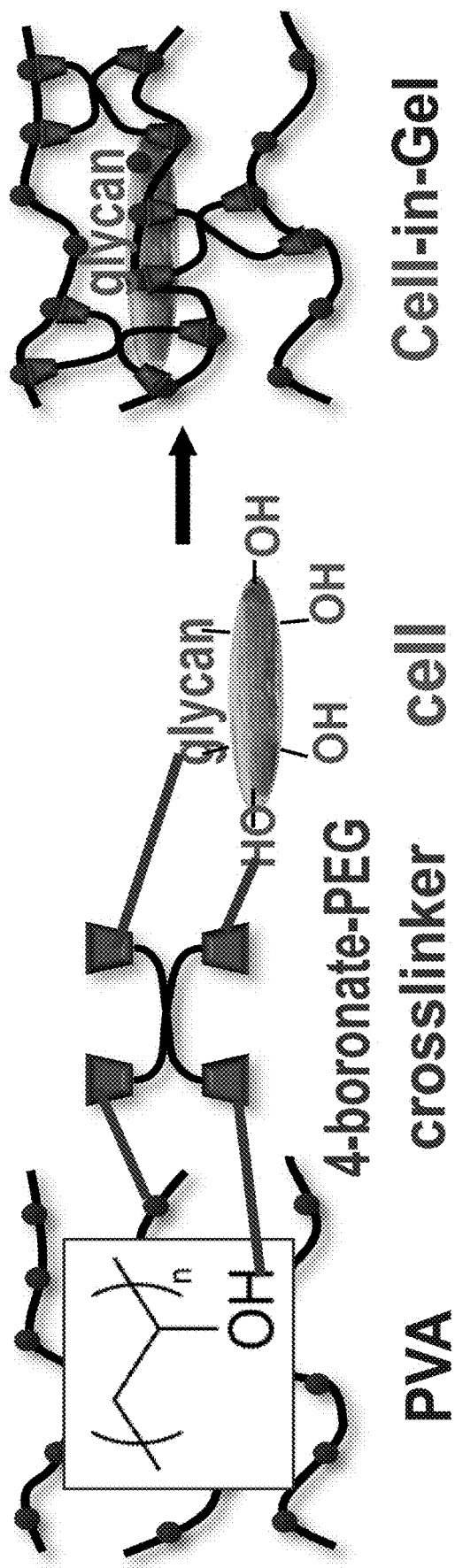
FIG. 4 illustrates that PVA-Boronate Gel tethers cell surface glycans and glycoproteins.

The PVA-Boronate Gel (FIG. 4) is composed of two parts: underivatized polyvinyl alcohol (PVA) and tetravalent 4-boronate-PEG crosslinker. Upon mixing the two components, the boronate spontaneously binds to the hydroxyl groups in PVA to form PVA hydrogel within 1-3 minutes at room temperature. This system can be used to create a Cell-in-Gel capsule by first suspending the freshly isolated cells, e.g., cardiac myocytes, in PVA solution, and then adding the crosslinker to form the PVA hydrogel with the single myocytes embedded in the gel matrix. The stiffness of the gel is tunable by adjusting the mixing ratio of the crosslinker and PVA. Hence we can engineer elastic gel of desired variable stiffness (e.g., in the range of about 0.5 kPa to about 50 kPa) to mimic various patho-physiological environments for cells. The gel can also be reversibly dissolved by adding sorbitol (or other sugars) in the bath solution to compete off and wash away the crosslinker.

1.3 the Avidin-Biotin Gel Composition for Tethering Cell-surface Integrins

In order to tether the cell-surface integrins without tethering the glycans, we designed a Avidin-Biotin Gel composed of three parts: Avidin, Biotin-PEG-Biotin crosslinker, and Biotin-Ligand (integrin binding ligand). This embodiment can be used to create a Cell-in-Gel configuration by doing the following:

(a) Incubate cells (e.g., myocytes) with Biotin-Ligand (which bind to the chosen integrin subtype).

(b) Suspend the cells (e.g., myocytes) in avidin solution.

(c) Add Biotin-PEG-Biotin crosslinker. Biotin and avidin spontaneously bind to form hydrogel with the single cells (e.g., myocytes) embedded in the gel matrix, and with the cell-surface integrin tethered to the avidin gel.

The Avidin-Biotin Gel does not tether the cell-surface glycans, and thus can be used to selectively tether the cell-surface integrins alone. Different subtypes of integrins can be tethers by using different Biotin-Ligand. For example, Table 1 lists several peptides that bind to different subtypes of integrins (Xiao, et al., *Molecular Cancer Therapeutics*. (2010) 9:2714-23; Yao, et al., *Journal of Medicinal Chemistry*. (2008) 52:126-33; Peng, et al., *Nat Chem Biol*. (2006) 2:381-9).

TABLE 1

| Peptides | Integrin Subtype | ECM binding partner |
|---|---|---|
| LXY3 | α3β1 | laminin |
| LLP2A | α4β1 | fibronectin (Fn), VCAM-1 |
| LXW7 | αvβ3 | fibronectin, fibrinogen, vitronectin |

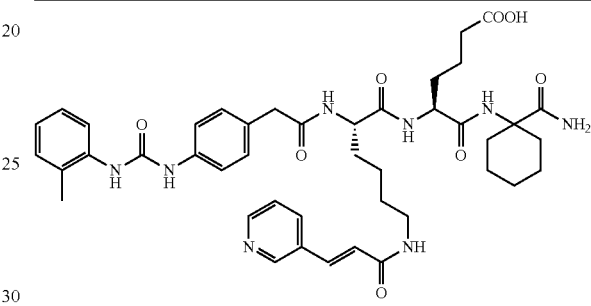

LLP2A

LXW7 is: cGRGDdvc
LXY3 is: cdG-Tyr(3-NO$_2$)-G-BNc; wherein B = hydroxyproline; lower letter represent D-amino acids; and Tyr(3-NO$_2$) is L-3-nitro-tyrosine.

Different integrins bind to different adhesion partners in the extracellular matrix. Hence, the biotin-peptide ligands can serve as a surrogate to the adhesion molecules in the extracellular matrix. When the cell (e.g., myocyte) is stretched or contracting against the gel, the biotin-peptide ligands will tug on the integrins to activate their mechano-chemo-transduction pathways, as would be activated if the cells were attached to the extracellular matrix in vivo. Here we use the advantage of our synthetic gel system (instead of matrigel or ECM extracts) to tug on each subtype of integrin individually to dissect out its role, and can also tug on a combination of integrins to investigate their collective effects.

1.4 Hybrid PVA-Avidin-Boronate Gel Composition for Tethering Cell-surface Molecules We also developed a hybrid PVA-Avidin-Boronate Gel which is designed to tether both glycans and integrins and any cell-surface molecules. The PVA-avidin-Boronate Gel is composed of three parts: PVA-avidin, 4-Boronate-PEG crosslinker, and Biotin-Ligand. The PVA-avidin is synthesized to build-in avidin 'hooks' in PVA for tethering biotin-conjugated molecules. The Biotin-Ligand can be chosen to bind to any cell-surface molecules of interest. For example, the ligand can be the peptides that bind to integrins or can be an antibody or antibody fragment that binds to a specific cell-surface molecule.

Figure 5:
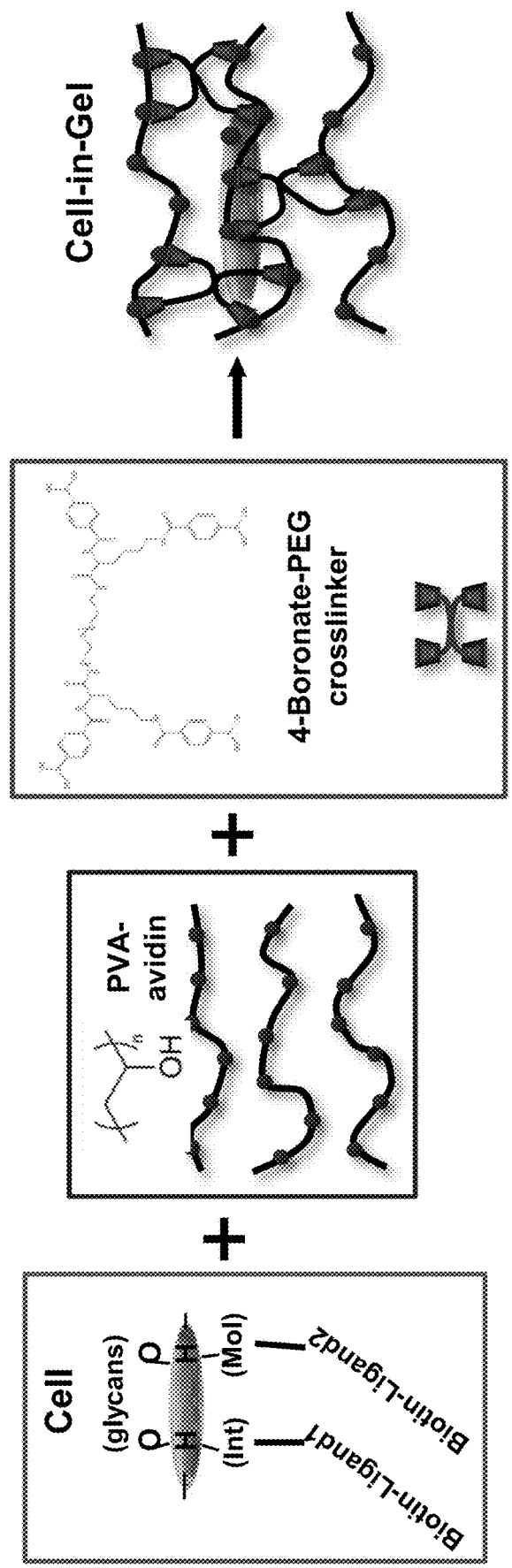
FIG. 5 illustrates that PVA-avidin-Boronate Gel can tether cell-surface glycans, glycoproteins, integrins, and any molecules of interest.

This hybrid system is used to create a Cell-in-Gel configuration by doing the following (see, FIG. 5).

(a) Incubate cells (e.g., myocytes) with the Biotin-Ligand which bind to chosen cell-surface molecule.

(b) Suspend the cells (e.g., myocytes) in PVA-avidin solution (see below for the PVAavidin synthesis procedure).

(c) Add 4-Boronate-PEG Crosslinker.

Boronate spontaneously binds to the hydroxyl groups in PVAavidin to form hydrogel with the single cells (e.g., myocytes) embedded in the gel matrix. The cell-surface glycans are tethered to the gel through boronate binding to the cis-diols in the glycans and the PVA. The cell-surface integrins or any other molecules can be tethered to the gel through Biotin-ligand binding to the avidin 'hooks' in the gel. Hence the PVA-avidin-Boronate Gel with avidin hooks provides a versatile system for tethering any cell-surface molecules individually or collectively.

1.5 the Biotin-ligands for Tethering Cell-surface Molecules to the Gel

The Cell-in-Gel system provides an experimental tool to impose mechanical stress on single cells and to tug on the cell-surface molecules. The cell-surface molecules are tethered to the gel either directly or through a biotin-ligand. An example of direct tethering is where the cell-surface glycans bind to boronate-based crosslinker and are thus tethered to the PVA gel. An example of using biotin-ligand as an intermediate link is where the biotin is conjugated to an integrin-binding-ligand which binds to the cell-surface integrin; at the other end, the biotin binds to the avidin in the PVA-avidin gel, thus tethering the integrin to the gel.

The PVA-avidin gel with biotin-ligand system provides a general method for tethering any cell-surface molecules. We have designed the following biotin-ligands to target cell-surface molecules either individually or collectively.

Figure 6:
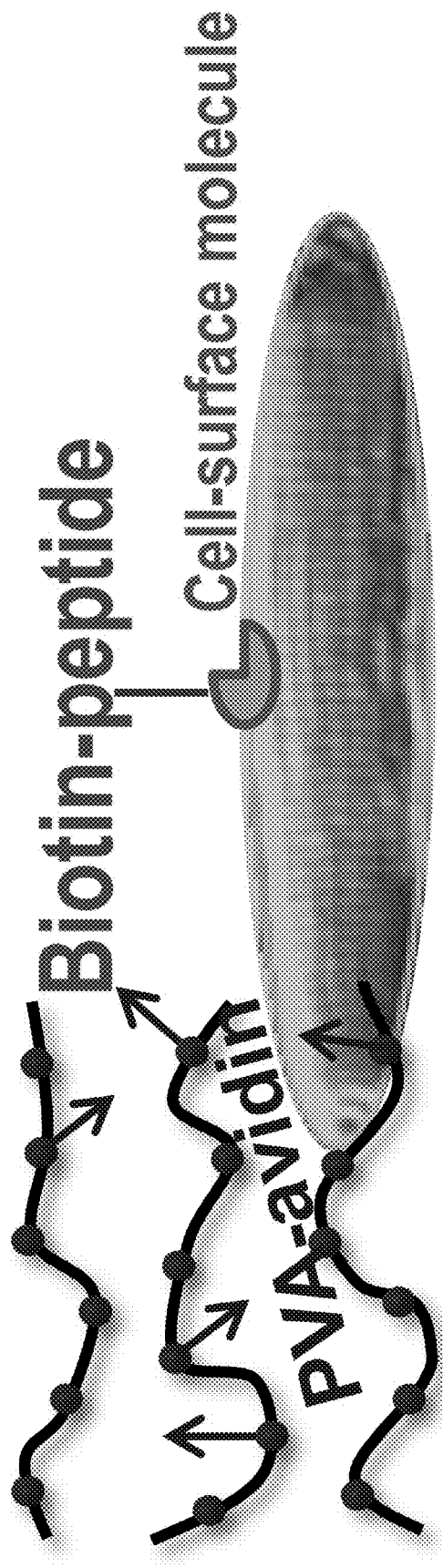
FIG. 6 illustrates a schematic of using biotin-peptide to tether cell-surface molecules to a PVA-avidin gel.

(a) Biotin-conjugated peptides (biotin-Peptide) provide another versatile method to tether cell-surface molecules to the gel (FIG. 6). The peptide can be the integrin binding peptide that binds to different subtypes of integrins. The peptides can also mimic the binding domains of the cell adhesion proteins in the extracellular matrix, and thus serve as their surrogate to bind to their adhesion partners on cell surface.

(b) Biotin-conjugated antibodies (biotin-antibody) provide a general method to tether any cell-surface molecules to the gel. A simple method is to use biotin-conjugated secondary antibody (biotin-$2^{nd}$ antibody) against IgG; the biotin-$2^{nd}$ antibody can bind to the primary antibody ($1^{st}$ antibody) that target a chosen cell-surface molecule and thus tether the molecule to the gel (FIG. 7A). An alternative approach is to use biotin-conjugated primary antibody (biotin-$1^{st}$ antibody) to bind to a chosen cell-surface molecule (FIG. 7B). Using biotin-$2^{nd}$ antibody provides a more versatile method than using biotin-$1^{st}$ antibody. We use a set of biotin conjugated secondary antibodies to bind to the IgG of different species (mouse, rat, rabbit, goat, and sheep) that are commonly used for generating the primary antibodies. This allows using any primary antibody to tether any cell-surface molecules of interest.

1.6 the Gel Compositions and Biotin-ligands for Tethering Cell-surface Molecules in Cardiac Myocytes As a proof of the principle for the above designs, we have conducted experiments to use biotin-ligands to tether cell-surface molecules in the cardiac myocytes. Of particular interest to the myocyte function and diseases are the DGC and VTI molecular complexes that transduce mechanical stress to biochemical reactions, as illustrated in FIG. 8. The cell-surface mechano-sensor of DGC are dystroglycans and sarcoglycans; of VTI are integrins. We used PVA-boronate gel to tether the glycans (FIG. 8A); used Avidin-Biotin gel to tether integrins (FIG. 8B); and used PVA-avidin-Boronate gel to tether both DGC and VTI (FIG. 8C). The experimental results of using the PVA-Boronate gel to activate DGC are described in Example 7, below. The data in FIG. 9 (upper panels) show that using PVA-Boronate gel to tug on DGC generated $Ca^{2+}$ sparks in the myocyte (seen as bright fluorescence spots in the 3D image presentation in FIG. 9A). The $Ca^{2+}$ sparks were cleaned out by inhibiting nNOS (FIG. 9B). Hence tugging on the glycans activated DGC and its associated nNOS, which in turn increased the ryanodine receptor activity to generate $Ca^{2+}$ sparks. Inhibiting eNOS (FIG. 9C) did not affect $Ca^{2+}$ sparks, indicating that eNOS was not activated by DGC and thus not involved in $Ca^{2+}$ spark generation.

Figure 2:
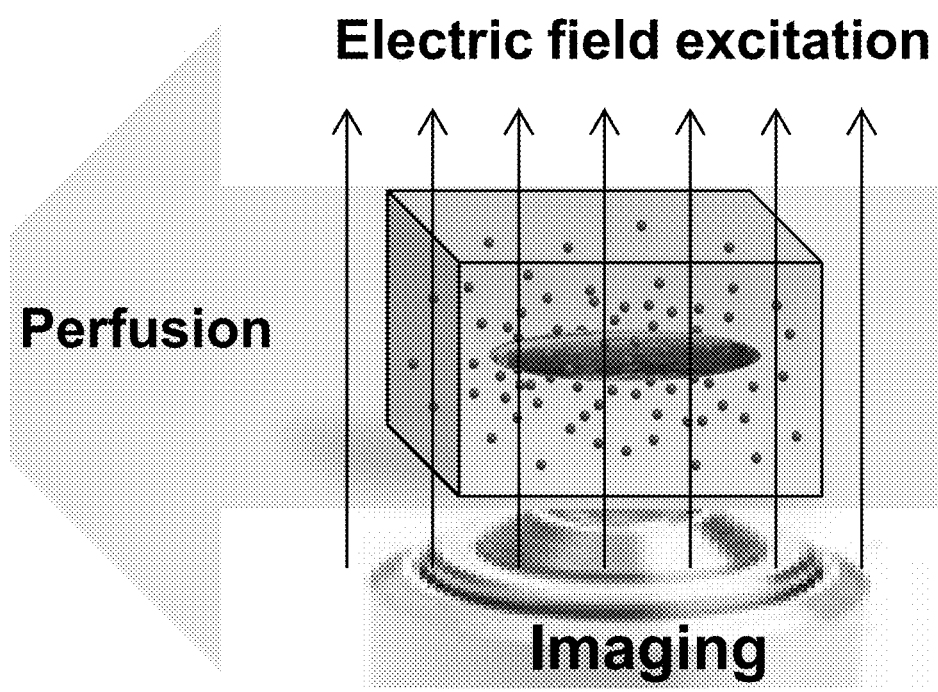
FIG. 2 illustrates the Cell-in-Gel system used in an experiment. The solution is continuously perfused to maintain the physiological condition (pH, temperature, ionic milieu etc.) in the hydrogel. Electric field is used to stimulation myocyte contraction. Microscopy is used to image the myocyte contraction and the mechano-chemo-transduction signaling events at cellular and molecular levels.

The results of using PVA-avidin-Boronate gel and Biotin-ligand to tether both DGC and VTI are shown in FIG. 9 (lower panels). In this experiment, we used the peptides listed in Table 1 to tether the three subtypes of integrins. The data in FIG. 9 show that tugging on both DGC and VTI during myocyte contraction in-gel caused the myocytes to generate $Ca^{2+}$ sparks (FIG. 9E, 2D image presentation). The $Ca^{2+}$ sparks were not cleaned out by inhibiting nNOS alone (FIG. 9F), but were eliminated by inhibiting both nNOS and eNOS (FIG. 9G). Therefore, tugging on DGC and VTI activated both nNOS and eNOS (also see FIG. 8C).

A useful alternative to tethering cell-surface molecules to the gel is to shield a specific molecule from being tethered to the gel. This can be achieved by using a non-conjugated antibody to bind to the specific molecule and thus masking it from being tethered to the gel. For example, we pre-incubated myocytes with an antibody against α-dystroglycan, and then embedded the cell in PVA-Boronate gel described above and herein. The gel tethers all other glycans on the cell surface (e.g., sarcoglycans, β-dystroglycan, etc.) except α-dystroglycan. This method can be used to remove α-dystroglycan from the mechano-chemo-transduction chain of command. Our experimental data showed that the $Ca^{2+}$ spark rate was reduced when α-dystroglycan was un-tethered, revealing the role of α-dystroglycan in transducing mechanical stress to generating $Ca^{2+}$ spark.

These experimental results demonstrate the feasibility of using the various gel compositions and Biotin-ligands to tether chosen cell-surface molecules.

1.7 the Cell-in-Gel Kit: Gel Components and Biotin-ligands for Tethering Cell-surface Molecules Components for assembling a Cell-in-Gel capsules can be packaged in a kit. At least two configurations are contemplated: (1) a kit containing the PVA-avidin gel can be used to tether cell-surface glycans and any other molecules; (2) a kit containing the Avidin-Biotin gel can be used to tether any cell-surface molecules without tethering glycans. The Biotin-ligand can be optionally included; users can also use other biotin-conjugated ligand or antibodies from other sources.

Example 2

Procedures for Synthesizing and Purifying the Gel Components

The procedures for synthesizing and purifying the Cell-in-Gel components are described in this example.

2.1 PVA-avidin

The PVAavidin was synthesized by using PVA (98 kDa) as the starting material. Avidin was added to PVA by conjugation. Then the access avidin was removed by filtration. An illustrative step-by-step procedure for synthesizing and purifying PVA-avidin is detailed below.

(a) 10 mL of 2% polyvinyl alcohol solution (PVA, 98 kDa) in dry DMSO was treated with NaH (0.05 equ, 0.23 mmol, 9.1 mg of NaH in mineral oil with 60% of purity) under $N_2$ atmosphere at room temperature with magnetic stirring for 2 hrs.

(b) Excess of epichlorophydrin (0.5 equ) was then introduced into the reaction and agitated overnight. 5 times volume of ethanol was added into the DMSO solution to precipitate epoxy-PVA.

(c) The polymer was further washed with ethanol for 3 times and dried under vacuum.

(d) Polymer was then dissolved in 20 mL PBS, followed by the addition of (0.05 equ) mL of avidin.

(e) The reaction mixture was further stirred at 4° C. for 24 hrs.

(f) The reaction mixture was then centrifuge filtered with a 100 kDa centrifuge filter device to remove excess unconjugated avidin.

(g) After each centrifuge filtration step, the final volume of the retentate solution was brought back to the starting volume by the addition of PBS.

2.2 Biotin-PEG-Biotin

The Biotin-PEG-Biotin was synthesized by using $NH_2$-PEG-$NH_2$ (20 kDa) as starting material. D-Biotin (6 equ.) was coupled onto the amino groups of PEG using 1,3-Diisopropylcarbodiimide (DIC) (6 equ.) and 6-chloro-1-hydroxybenzotriazole (Cl-HOBt)(6 equ.) as coupling reagents in DMF for overnight. The completion of the coupling was monitored by Kaiser test: yellow color indicates no amino group left, blue color indicates the presence of amino groups. PEGylated molecules were precipitated by adding cold ether and washed with ether for 3 times. This biotin-PEG-biotin was subsequently dialyzed and lyophilized to yield a white powder. An illustrative step-by-step procedure for synthesizing Biotin-PEG-Biotin is detailed below.

(a) Weight out $NH_2$-PEG-$NH_2$ (20K), and 6 equivalency of Cl-HOBt, D-Biotin and DIC, respectively.

(b) Add D-Biotin into 10-15 mL coupling DMF and heat with microwave for around 30s until all powder completely dissolved in the DMF, then add $NH_2$-PEG-$NH_2$ and Cl-HOBt into the solution and vortex until all reagents dissolved, finally add DIC.

(c) Transfer the whole reaction solution into a 100 ml plastic bottle and shake the bottle at 200 rpm overnight.

(d) On the following day, take out around 200 µl of reaction solution, precipitate the solution with cold ether and perform Kaiser test on product.

(e) With negative Kaiser test, proceed to precipitate all the reaction solution and wash the products for three times with cold ether.

(f) Put the reaction products under vacuum until the powder is complete dry.

(g) Dissolve the final biotin-PEG-biotin into coupling DMF and dialyzes the solution with membrane pore size between 6-8 k.

(h) Finally, lyophilize the solution and the powder is ready to use.

Example 3

Protocols and Solutions for Working with Live Cells in the Cell-in-Gel System

The solutions for working with live cells are based on the standard Tyrode solution or phosphate buffered saline (PBS). Each of the gel components is dissolved in the Tyrode (e.g., 119 mM NaCl, 5 mM KCl, 25 mM HEPES buffer, 2 mM $CaCl_2$, 2 mM $MgCl_2$, 6 g/liter glucose, pH adjusted to 7.4 with NaOH) or PBS with the physiological pH (7.2-7.4) value. We modified the Tyrode solution to remove glucose (which is normally present), and substitute it with pyruvic acid (a down-stream metabolite of glucose for energy supply). This is because the glucose competed with the boronate crosslinker to slowly soften the gel over extended incubation times. Substituting glucose with pyruvic acid solved this problem.

Below is an illustrative step-by-step protocol to quickly embed cells in the gel, to tether specific cell-surface molecules to the gel, and at the same time to avoid cell damage in order to preserve the function of live cells.

(a) Freshly isolated cells (ventricular myocytes) are suspended in the modified Tyrode solution (see below for recipe) and stored at room temperature. Add 20 µM Biotin-ligand solutions into the cell suspension, gently mix, and incubate for 15-20 minutes.

(b) Wash away the unbound Biotin-Ligand with Tyrode, and condensed the cell concentration by letting the cells to sink down in a 1.5 ml Eppendorf vial and remove the supernatant to leave 0.5 ml solution. Gently mix to suspend the cells. Note: To prevent myocyte contraction under mechanical disturbance, reduce the $Ca^{2+}$ concentration in the Tyrode solution from 1 mM to 20 µM to relax the cells so the cells will be embedded at relaxed state.

(c) Gently mix 15 µl cell suspension into 35 µl PVA-avidin solution.

(d) Pipette 15 µl cells suspended in PVA-avidin into a chamber atop a No. 1 glass coverslip. As depicted in FIG. 6 below, the chamber is made to contain a Cell-in-Gel capsule of about 100 µm thickness. The No. 1 glass coverslip (thickness about 0.15 mm) at the bottom of the chamber allows imaging on the microscope using objectives of short working distance (fluorescence imaging at high magnification requires using the objectives of large Numerical Aperture, NA, and hence short working distance).

(e) Let the cells settle in PVAavidin solution for 2-3 minutes. Then add 15 µl crosslinker on top, and mix quickly but gently. The hydrogel spontaneously form within 3-5 minutes to embed the single cell in the 3D gel matrix. Note: Only a small volume is needed for embedding a single cell (cardiac myocyte size ~120×40×30 µm; cancer cell size ~15-20 µm in diameter), hence we recommend to make a small Cell-in-Gel capsule to facilitate diffusion of the crosslinker and to avoid mechanical mixing. This is especially important for myocytes, because mechanical disturbance can cause myocyte contraction.

(f) Incubate the Cell-in-Gel capsule for 5 minutes at room temperature in a moisture chamber (enclosed petri dish with wet filter paper) for the gel to form.

(g) Mount the glass coverslip with the Cell-in-Gel capsule into a perfusion chamber, and quickly cover the gel with Tyrode solution. Now the Cell-in-Gel system is assembled and ready for experiments.

TABLE 2

| | Tyrode solution based recipes | | |
|---|---|---|---|
| Chemicals | Normal Tyrode Concentration (mM) | Low $Ca^{2+}$ Tyrode Concentration (mM) | Pyruvate Tyrode Concentration (mM) |
| NaCl | 145 | 145 | 145 |
| KCl | 4 | 4 | 4 |
| $CaCl_2$ | 1 | 0.02 | 1 |
| $NaH_2PO_4$ | 0.33 | 0.33 | 0.33 |

TABLE 2-continued

Tyrode solution based recipes

| Chemicals | Normal Tyrode Concentration (mM) | Low $Ca^{2+}$ Tyrode Concentration (mM) | Pyruvate Tyrode Concentration (mM) |
|---|---|---|---|
| $MgSO_4$ | 1 | 1 | 1 |
| HEPES | 10 | 10 | 10 |
| Glucose | 10 | 10 | 0 |
| Pyruvic acid | 0 | 0 | 5 |
| pH (NaOH adjusted) | 7.3 | 7.3 | 7.3 |

Example 4

Cell-in-Gel Capsule and Device for Controlling Mechanical Preload and Afterload on Cells We designed a comb-like mounting grip to mount the Cell-in-Gel capsule onto the experimental apparatus, as illustrated in FIG. 10. The comb grips in the gel allow material to draw inward and translate a bit, a way to get nearly uniform strain fields across the gel. The Cell-in-Gel capsule can be grabbed by the Comb-Grip and then mounted between a micro-manipulator and a force transducer. The mechanical load on the Cell-in-Gel capsule is controlled by the micromanipulator and monitored by the force transducer.

Mechanical preload on the cell can be imposed by using the micromanipulator to stretch the Cell-in-Gel capsule; the preload level is controlled by the extent of stretch. Mechanical afterload on the cell can be imposed by using electrical field to stimulate myocyte contraction in the Cell-in-Gel capsule; the afterload level is controlled by the stiffness of the gel. Combining the stretching with contraction imposes both the preload and the afterload on the cell. Hence this system allows controlling the mechanical preload and the afterload on the single cell.

The Comb Grip for the Cell-in-Gel capsule can also be custom-designed to fit any apparatus, for example, the IonOptix MyoStretcher (originally designed to grab single myocyte with a pair of glass rods (Tribe, *Circ Res.* (2009) 104:787-95), IonOptix LLC, USA).

Example 5

The Cell-in-Gel Array for High Throughput Drug Screening

The Cell-in-Gel system can be scaled up to build a large throughput drug screening system to search for new drugs that affect the myocytes mechano-chemo-transduction. The high throughput Cell-in-Gel system contains the following components.

(a) Array of the Cell-in-Gel Capsules;

(b) Perfusion channel through each Cell-in-Gel Capsule;

(c) Electrical stimulator to pace the myocytes in-gel to undergo excitation-$Ca^{2+}$ signaling-contraction;

(d) Imaging system equipped with laser excitation light source, optical filters, and emission light detectors.

(e) A analog-digital converter and a computer to record the imaging data;

(f) Software for computer control of the drug perfusion of Cell-in-Gel Capsule, data acquisition, and data analysis.

Example 6

Testing of the Cell-in-Gel System 6.1 The Gel Components and their Assembly are Non-toxic to Live Cells We designed the gel to contain avidin 'hooks' which allows tethering of any biotin-ligands to the gel through spontaneous avidin-biotin binding. The basic components of the gel contains: PVA, PVA-avidin, 4-boronate-PEG crosslinker, and all components are dissolved in physiological saline (phosphate buffered saline PBS, or in the Tyrode solution, with pH 7.3). We tested the cytotoxicity of each component by pre-incubating freshly isolated myocytes in each gel component, and then measured the myocyte contraction as a sensitive functional output. Our data show that the myocyte contraction was not altered by any of these components. Then we mixed these components to form hydrogel with myocytes embedded in the 3D elastic gel matrix. The myocytes were able to undergo excitation-contraction coupling in the gel. Hence the myocytes were able to perform their natural physiological function in the gel and also in each gel component without showing any apparent damage, in a time span that is usually expected for a freshly isolated myocyte to function normally in physiological saline (without gel).

6.2 Mechanical Analysis of the Cell-in-Gel System

To quantify the mechanical strain and stress in the myocyte during contraction under afterload, we performed mathematical modeling of the 3D Cell-in-Gel system (Shaw, et al., *PLoS One.* (2013) 8(10):e75492). The results show (B) the cell experiences a highly non-uniform distribution of both normal and shear traction (force/unit area) on its surface during in-gel contraction. (C) The 3D Stress Map of the longitudinal stress shows that the stress state within the cell interior is nearly uniform, yet the exterior (gel) stress field is quite in-homogeneous with 'hot spots' at the apex and waist of the myocyte on its surface. Stress maps of other stress components, such as lateral stresses are similar (but compressive within the cell) indicating the cell experiences multi-axial loading. Hence, the mechano-chemo-transduction (MCT) complexes at different geometric locations on the cell surface should experience varying levels of normal and shear stress. It is reassuring that the highest stress level at the apex coincides with the Intercalated Disc—a known stress bearing structure. This is the first time that such 3D stress mapping of myocyte architecture has been quantitatively analyzed. Currently our analytical solutions are expressed in dimensionless (normalized) terms which readily lend themselves to parametric studies.

Example 7

Mechano-chemo-transduction During Cardiac Contraction Mediated by Localized Nitric Oxide Signaling Cardiac myocytes contract against a mechanical load during each heartbeat, and excessive mechanical stress leads to heart diseases. Using a novel Cell-in-Gel system that imposes an afterload during myocyte contraction, we identified nitric oxide synthase (NOS) as key molecules involved in transducing mechanical load to alter $Ca^{2+}$ dynamics. In mouse ventricular myocytes, afterload during cell contraction increases systolic $Ca^{2+}$ transient and diastolic spontaneous $Ca^{2+}$ sparks, which are due to increased ryanodine receptor (RyR) sensitivity since the SR load remains unchanged. Afterload-induced $Ca^{2+}$ sparks are prevented by either pharmacological inhibition or genetic deletion of nNOS, but not of eNOS. This differential effect may arise from closer physical proximity of nNOS to RyR compared to that of eNOS to RyR, as resolved by super-resolution imaging. In addition to NOS, $Ca^{2+}$-calmodulin dependent protein kinase II (CaMKII) and nicotinamide adenine dinucleotide phosphate oxidase 2 (NOX2) are also involved in the mechano-chemo-transduction. In a mouse model of cardiomyopathy with increased myofilament $Ca^{2+}$ sensitivity, the mechanotransduction is further intensified to cause frequent $Ca^{2+}$ sparks as well as $Ca^{2+}$ waves. The spontaneous $Ca^{2+}$ activities are eliminated by inhibiting nNOS and CaMKII but not NOX2, demonstrating independent activation of NOS and NOX by the mechanotransduction complex. In conclusion, our data reveal nNOS and CaMKII as novel key mediators in mechano-chemo-transduction during cardiac contraction, which provides new mechanistic insight and therapeutic targets for treating mechanical stress induced $Ca^{2+}$ dysregulation, arrhythmias and cardiomyopathy.

Introduction

The heart must pump blood against mechanical loads that constantly change with physical activity, posture, emotion, and pathophysiological states. The Anrep effect (1-4) describes an enhancement of cardiac contractility resulting from increased afterload, which is complementary to the Frank-Starling mechanism describing enhanced contractility from increased preload (5). A pioneering study by Petroff et al. (6) found that stretching cardiac myocytes to increase preload can induce spontaneous $Ca^{2+}$ sparks through activating the nitric oxide synthase 3 (eNOS). Recent studies by Prosser et al. (7, 8) showed that stretching the myocyte activates nicotinamide adenine dinucleotide phosphate oxidase 2 (NOX2) to cause $Ca^{2+}$ sparks. Preload-induced changes in $Ca^{2+}$ handling contribute to the Frank-Starling mechanism. However, it remained unknown whether afterload might also cause changes in $Ca^{2+}$ handling and whether analogous mechano-chemo-transduction mechanisms could be activated in the myocytes contracting against a mechanical load. Excessive afterload under pathological conditions such as hypertension, asynchronous contraction, and infarction are known to lead to cardiac remodeling, hypertrophy, arrhythmias and heart failure (9-11). Here we identified nNOS, eNOS, NOX2 and $Ca^{2+}$-calmodulin dependent protein kinase II (CaMKII) as key mediators of mechano-chemo-transduction pathways that link mechanical afterload to $Ca^{2+}$ handling. This enriches mechanistic understanding of the Anrep effect and helps to identify possible molecular targets for treating mechanical stress induced heart diseases.

Materials and Methods

All laboratory procedures conform to the Guide for the Care and Use of Laboratory Animals published by the US National Institutes of Health. The animal usage was approved by the local Institutional Animal Care and Use Committee.

Cell isolation. Wild-type and transgenic mice, 8 weeks old male, were purchased from Jackson Laboratories (USA): C57BL/6J (wild-type), B6.129S4-Nos1tm1Plh/J (NOS1−/−), B6.129P2-Nos3tm1Unca/J (NOS3−/−). Transgenic mouse with R92Q mutation in cardiac troponin T was created in Tardiff's lab (22) and bred in Chen-Izu's lab. A standard enzymatic technique (40) was used to isolate the ventricular myocytes using Worthington collagenase type II and Sigma protease type XIV. All experiments were conducted at 21-22° C.

Cell-in-Gel system. Elastic gel matrix was made of a poly vinyl alcohol (PVA) hydrogel system comprised of underivatized PVA (98 KD) and a tetravalent boronate-PEG crosslinker (12). Freshly isolated myocytes were first suspended in 7% PVA solution; then 7.5% crosslinker solution was added in equal volume (Gel7.5%). Upon mixing, the boronate group crosslinks PVA hydrogel, embedding the cell in the 3D gel matrix. The boronate group also crosslinks the cis-diols of the cell-surface glycans to PVA, thereby tethering the cell surface to the gel. We used Gel7.5% for all the experiments in this study except one group in FIG. 11G using Gel5%.

The present Cell-in-Gel system has several useful properties. (1) Upon electrical field stimulation, the myocyte undergoes excitation-contraction in the elastic gel, and the gel matrix resists the shortening and broadening of the cell during contraction, thereby exerting multi-axial mechanical stress on the cell. (2) The stiffness of the gel is tunable by the mixing ratio of the crosslinker and PVA [41]. In most experiments, equal volume of 7.5% crosslinker and 7% PVA were mixed to form 7.5% Gel. In a few experiments, 5% crosslinker and 7% PVA were mixed to form a softer 5% Gel. (3) The gel matrix is porous to allow rapid bath solution exchange for studying drug effects. (4) The gel matrix is optically transparent for real-time imaging of cell contraction and also fluorescence imaging of $Ca^{2+}$ signals.

Figure 12:
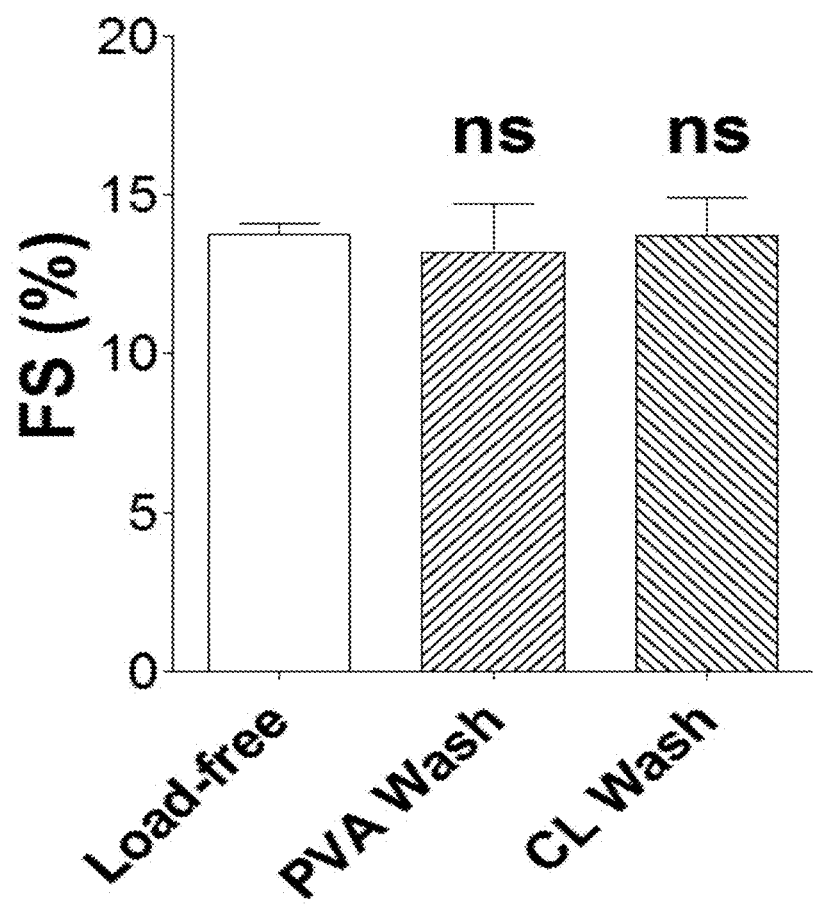
FIG. 12 illustrates PVA or crosslinker alone did not affect myocyte contraction. Fractional shortening (FS) of cardiac myocytes post-incubation in either PVA (n=27 cells) or crosslinker (CL, n=8 cells), in comparing to the load-free control in the normal Tyrode solution (n=6 cells). One-way ANOVA test show no significant difference (p=0.86). Hence the individual gel components alone do not alter myocyte contraction, indicating none-toxicity.

We conducted control experiments to examine the effect of PVA or crosslinker alone on the myocytes by pre-incubating the cells in PVA or CL for 10 minutes, and then perfuse the cells with the normal Tyrode solution and measure the cell contraction. FIG. 12 shows that pre-incubation with PVA or CL alone did not change the contraction of rabbit myocyte. We also further examined the spontaneous $Ca^{2+}$ activities induced by myocyte contraction in-Gel (see below). The data show that the cell sitting in the gel before electrical pacing did not have $Ca^{2+}$ sparks; then the cell contraction in-Gel generated diastolic spontaneous $Ca^{2+}$ sparks and waves; and then stop pacing abolished cell contraction and eliminated spontaneous $Ca^{2+}$ activities. These evidences clearly rule out the possibility that the gel alone would alter the $Ca^{2+}$ signaling and cell contraction.

The current technology to control mechanical stress at the single cell level can be classified below. 1D (uniaxial) techniques by using a pair of micro-cantilevers (carbon fiber [42], glass rod [43]) to stretch the cell have produced valuable data, but it differs from the 3D environment in vivo. 2D techniques to culture cells on a deformable membrane or microposts are used to stretch neonatal myocytes [44] etc., but freshly isolated adult myocytes do not easily attach to the membrane. 3D technique by encasing cells in a fibrinogen-thrombin gel [45] and later in agar [6], but the cell surface does not adhere to agar. Also, skinned ('dead' cell) muscle or myofibril preparations are commonly used to study passive muscle mechanics, but mechano-chemo-transduction need to be studied in live intact myocytes. Therefore, our Cell-in-Gel system more closely mimics the physiological environment by tethering the cell surface to gel and imposing 3D mechanical stress on a single live adult cardiac myocyte.

Our data are consistent with the conclusion that cell surface adhesion to the 3D gel matrix (mimicking adhesion to the extracellular matrix in vivo) plays an important role in mechano-chemo-transduction. Our working hypothesis is that in the Cell-in-Gel system, the cell-surface glycans are linked to the PVA gel matrix through boronate binding. Since the cell surface experiences both the normal and the shear stresses during myocyte contraction [13], it is plausible that the gel tugs the cell-surface glycoproteins including dystroglycans and sarcoglycans to impose mechanical strain and stress on these mechano-sensing molecules in the dystrophin-glycoprotein complex. It is known that dystrophin links to nNOS [46]. This notion is consistent with our finding that nNOS is activated in the myocytes contracting in-Gel.

Furthermore, the cardiac myocytes in vivo most likely experience both preload and afterload during a cardiac cycle when the myocardium is stretched at the end-diastolic period and then contracts against a mechanical load. The 'Cell-in-Gel' system provides an experimental tool for investigating the afterload effects [6] [42] [43]. This system can be further developed to also impose preload by stretching the gel. The present study is our first effort focusing on the afterload-induced mechano-chemo-transduction, which complements the previous studies of the preload effects. Our study here paves foundation for the next phase of investigation to impose both preload and afterload to study their combined effects.

Mechanical analysis of myocyte contraction in 3D elastic matrix. The stiffness of the PVA gel was measured using a TA-XT2 Texture Analyzer (Stable Micro Systems, England). PVA gel sample of 50 mm diameter and 1.5 mm thickness was submitted to a unidirectional strain. The applied strain of 10% was small enough to remain in the linear region of the stress-strain response, and the Young's modulus was calculated from the slope of stress verses strain plot. The stiffness of the gel was controlled by the mixing ratio of the crosslinker and PVA [41]. Unless indicated otherwise, experiments in this study were conducted using Gel7.5% with Young's modulus of 1 KPa. We have conducted 3D mechanical analysis for the myocyte contraction in elastic gel [13]. The major findings include (1) the stress state is uniform inside the cell; the axial stress along the longitudinal axis is about 15 times of the lateral stress along the transverse axis. (2) The surface traction (shear stress) is highly non-uniform; it is minimal at the cell's waist, gradually rises along the length, and reaches a maximum near the apex. (3) The fractional shortening of myocyte in-Gel is less than that of load-free contraction. The knock-down factor is determined by the geometric dimensions of the cell and the relative stiffness of the cell to gel; a slender or softer cell has less fractional shortening. The above results from the rigorous 3D mechanical analysis establish using the Cell-in-Gel system to impose longitudinal tension, lateral compression, and surface traction to the single myocyte in mimicking the mechanical environment in vivo.

Confocal imaging of $Ca^{2+}$ signals. Myocytes were loaded with $Ca^{2+}$ indicator, Fluo-4, and then embedded in the gel. Confocal imaging was performed using standard method (41).

For confocal imaging of the $Ca^{2+}$ signals, freshly isolated myocytes were continuously perfused in Tyrode solution containing (in mM): 150 NaCl, 5.4 KCl, 1.2MgCl$_2$, 1 CaCl$_2$, at pH 7.4, loaded with $Ca^{2+}$ indicator Fluo-4, and then embedded in the PVA gel. The cell was paced at 0.5 Hz frequency by electrical field stimulation using short (4 ms) depolarization pulses with bipolar switching (switch positive and negative polarity in consecutive stimulus pulses). The platinum electrodes were used in conjunction with continues perfusion of fresh Tyrode solution to maintain constant bath condition (pH, glucose, ionic composition, temperature etc.).

Confocal images were obtained using an Olympus FluoView 1000 Confocal Microscope (inverted configuration) with a water immersion fluorescence objective UPlanSApo 60X, NA1.2, corrected for the thickness of the No. 1 glass coverslip that is used at the bottom of the perfusion chamber. Fluo-4 was excited with 488 nm laser beam (laser power set to 5%), and the emitted fluorescence light was passed through a bandpass filter BA505-605 and collected with a PMT. The PMT voltage, gain, and offset were set to avoid any saturation and to obtain high fidelity images. The line-scan images were obtained using the highest scan speed of 2 μs/pixel.

$Ca^{2+}$ sparks were detected automatically using a home-made program based on our spark identification algorithm and adapted for x-t linescans [47]. As in our 2-D program, sparks are identified in two stages. In the first stage, putative sparks are detected based on Cheng et al.'s description [48] and bright but spatially small events were eliminated using the 'live-or-die' algorithm described in our previous publication [49]. In the second stage, the putative sparks were classified as sparks or noise based on the statistical sieve as described previously in our publication [47]. This analysis software provides automated and objective (agnostic via statistical sieving) detection and classification of the $Ca^{2+}$ signaling events. Confocal imaging of the Flou-4 signals was primarily used to detect the $Ca^{2+}$ sparks and waves, because Fluo-4 is one of the best indicators available for detecting small changes in the local $Ca^{2+}$ signals owning to its high quantum yield.

Mechanical load effects on the myocyte contraction and systolic $Ca^{2+}$ transient. To establish that the diastolic spontaneous $Ca^{2+}$ sparks are indeed caused by the mechanical load, we examined the $Ca^{2+}$ spark rate in the myocytes contracting under different mechanical loads as shown in FIG. 11G. We also examined the systolic $Ca^{2+}$ transient and the myocyte contraction under these conditions of varying loads. FIG. 13A shows that, in comparing to load-free contraction, myocyte contraction in soft gel (Gel5%, made of 5% crosslinker) under moderate mechanical load did not significantly alter the $Ca^{2+}$ transient; however, myocyte contraction in stiffer gel (Gel7.5%, made of 7.5% crosslinker) under higher mechanical load significantly increased the $Ca^{2+}$ transient due to mechano-chemo-transduction, although the contraction amplitude decreased due to larger load (FIG. 13B). Blebbistatin (10 μM) treatment, which decoupled cell contraction from $Ca^{2+}$ signaling (FIG. 13B), removed mechano-chemo-transduction and restored the $Ca^{2+}$ transient to the load-free condition (FIG. 13A); this normalization of the $Ca^{2+}$ transient is also consistent with the normalization of $Ca^{2+}$ spark rate after removing mechanical load (FIG. 11G).

Whole cell $Ca^{2+}$ transient measurement using Fura-2 ratiometric method. In order to more precisely measure the whole cell $Ca^{2+}$ concentration, we used Fura-2 ratiometric method (40) rather than Fluo-4 single wavelength measurement. Fura-2 loading was done by incubating the cells with 2.5 μM Fura-2/AM and 0.75 μM Pluronic-127 (in 20% DMSO) at room temperature for 30 minutes. After washing out Fura-2/AM, the cells were incubated for an additional 45 minutes, and then used for experiment within 2 hours. An IonOptix system (IonOptix Inc., USA) with a Hyperswitch and mounted on the Olympus X71 inverted microscope with a water immersion fluorescence objective UPlanSPao 40x, 1.15 NA, corrected for the thickness of the No. 1 glass coverslip. The excitation light was generated using a high intensity ARC lamp (Cairn). The Hyperswitch (galvanometer based switching between 340 mm and 380 nm at 500 Hz frequency, using a 340/370d/380 filter cube) was used to deliver dual excitation beams at 340 nm and 380 nm, switching between the two wavelengths. Fura-2 fluorescence emission light was passed through a bandpass filter D510/40m, and then collected in a photomultiplier tube (PMT). The gain of the PMT was set to avoid any saturation and to obtain high fidelity photon count.

The Fura-2 fluorescence emission (F) from the excitation at 340 nm and 380 nm were recorded from the cell. The background fluorescence (BG) at 340 nm and 380 nm wavelengths were obtained in the solution and in the gel without cell. The BG signals were found slightly higher in the gel than in solution, but both were substantially lower than the Fura-2 fluorescence emissions from the cell. The Fura-2 fluorescence ratio, RFura, was calculated after background subtraction.

For measuring the systolic $Ca^{2+}$ transient, the cell was first paced to reach steady-state (>2 minutes), and then the Fura-2 fluorescence was recorded for at least 10 beats during steady-state. For SR content measurement, after the cell reaching steady-state the field stimulation was stopped to keep the cell at resting state for 15 seconds; then caffeine at high concentration (20 mM) was applied to rapidly deplete the SR load (FIG. 14A,B). The rapidity of the SR $Ca^{2+}$ release was accessed by the rising velocity of the caffeine-induced $Ca^{2+}$ transient, and the peak $Ca^{2+}$ value was used as an index to measure the SR load. As noted, the SR $Ca^{2+}$ content using either fura-2 (FIG. 14D) or other indicators did not show any discernable difference between the Cell-in-Gel and the load-free contraction. Since RyR sensitivity to intra-SR [$Ca^{2+}$] is steep, we also acknowledge that small changes in SR $Ca^{2+}$ that we could not detect could have functional impact.

Myocyte contraction measurement. Contraction measurement using Fluo-4 confocal image was determined from the confocal x-t linescan by the difference in the positions of the left and right boundaries demarcated by the bright fluo-4 signal and the dimmer signal from the PVA gel or the bathing solution. Myocyte length was calculated by converting the fluorescence signal along each x into a binary vector. Fluorescence values above background plus a threshold were considered 1, otherwise 0. The numbers of "1" pixels was then multiplied by a scaling factor (determined by using a Ronchi ruling with 2.5 spacing) to get the cell shortening in microns. The threshold was set to half of the maximum calcium fluorescence.

Contraction measurement using IonOptix system (IonOptix Co., USA) with sarcomere detection was done by using a high speed camera (Myocam-S, 240 up to 1000 frame/s) the record the sarcomere movement during contraction. The sarcomere pattern in the myocyte was then used to calculate the sarcomere length change using a Fast Fourier Transform algorithm (FFT).

We decided to use the IonOptix sarcomere detection and FFT method to measure the myocyte contraction in our experiments rather than Flou-4 confocal imaging edge detection, because the latter may involve some imprecision if the cell ends move out of the focal plan during myocyte contraction. The sarcomere FFT method usually provides more stable (immune to the edge movement) and precise measurement of the myocyte contraction in terms of the average sarcomere length shortening.

Effects of inhibiting nNOS versus eNOS on the $Ca^{2+}$ transient and myocyte contraction in-Gel. Mechanical load-induced spontaneous $Ca^{2+}$ sparks were suppressed by inhibiting nNOS but not eNOS (FIG. 15); this differential effect prompted us to ask whether the systolic $Ca^{2+}$ transient was also suppressed by inhibiting nNOS but not eNOS. FIG. 16 shows that using L-NPA (5 μM) to inhibit nNOS indeed reduced the $Ca^{2+}$ transient (panel A); using L-Nio (10 μM) to inhibit eNOS not only reduced the $Ca^{2+}$ transient (A) but also slowed the speed of $Ca^{2+}$ transient decline (prolonged tau in B). Taken together, nNOS inhibition significantly suppresses diastolic $Ca^{2+}$ sparks and slightly reduces the systolic $Ca^{2+}$ transient, whereas eNOS inhibition does not suppress $Ca^{2+}$ sparks but significantly reduces the $Ca^{2+}$ transient and also slows down the $Ca^{2+}$ removal from cytosol. These data are consistent with the conclusion that differential effects of nNOS versus eNOS on modulating different $Ca^{2+}$ handling pathways. Our working hypothesis is that nNOS might predominantly modulate RyR and SERCA due to its closer proximity to SR, whereas eNOS might predominantly affect the $Ca^{2+}$ handling protein near sarcolemma including Na+/$Ca^{2+}$ exchange, sarcolemma $Ca^{2+}$ pump, and L-type $Ca^{2+}$ channels. This tantalizing hypothesis needs to be tested by a full scale investigation on the nNOS versus eNOS effects on all these $Ca^{2+}$ handling molecules.

Inhibition of nNOS and eNOS also reduces the myocyte contraction (measured as Fractional Shortening, FS in FIG. 16C), in accordance to their effects on reducing the $Ca^{2+}$ transient. Interpretation of the contraction data needs to take into account the following complexity. When the myocyte is pulling mechanical load, the contraction amplitude is expected to decrease. However, if without the mechano-chemo-transduction mediated increase of $Ca^{2+}$ transient, the decrease in contraction would be more severe. In other words, if the myocyte was purely elastic, the contraction would be less than that measured in a live myocyte with active mechano-chemo-transduction regulation to increase the $Ca^{2+}$ transient. To address this issue, we have performed mechanical analysis of the Elastic-model assuming no mechano-chemo-transduction [13], which provides analytical solutions that readily lend themselves to parametric calculations. For example, the Knockdown Factor (KF=ratio of the myocyte shortening in-Gel to that in load-free condition) is a function of the mechanical load. For a canonical myocyte in-Gel under our experimental condition, the Elastic-model predicts KF is 0.2. However, the experimentally measured KF is about 0.4 (FIG. 16C), because the mechano-chemo-transduction caused increase of $Ca^{2+}$ transient enhances contractility. Inhibiting nNOS or eNOS disrupts the mechano-chemo-transduction signaling and thus reduces KF towards the basal level (FIG. 16C).

The Cell-in-Gel system provides a powerful technique to enable such investigation. Here, we focus on establishing the Cell-in-Gel technique and investigating the nNOS versus eNOS effect on RyR.

Antibody labeling of freshly isolated ventricular myocytes. Antibody labeling of freshly isolated ventricular myocytes were done based on our previously described protocol [49] with minor modifications. Briefly, cells were washed in the normal Phosphate Buffer Solution (PBS) at room temperature, and then fixed in 1% Paraformaldehyde PBS solution for 10 minute. After being washed twice in cold PBS (on ice or in refrigerator at 4° C.), the cells were then permeablized in cold 0.1% Triton X-100 PBS solution for 10 minute. The cells were incubated with the primary antibody (1:100 dilution) solution containing 5% bovine serum albumin, 3% goat serum 0.01% and Triton X-100 in PBS for 2 hour at room temperature; washed twice in cold PBS, and then incubated with the secondary antibody (1:100 dilution, Molecular Probes, USA) solution for 2 hour at room temperature or overnight at 4° C. For antibody labeling of RyR, nNOS, and eNOS, we used anti-RyR monoclonal antibody (clone C3-33, Affinity BioReagents Inc. USA), anti-nNOS polyclonal antibody (Thermo Scientific), and anti-eNOS polyclonal antibody (Thermo Scientific), respectively.

For colocalization study, we dual labeled the cells using two primary antibodies from different species to simultaneously label molecule A and B (AB pair) in the same cell; fluorophore-conjugated secondary antibodies targeting each of the primary antibodies were then used simultaneously to visualize A and B. The fluorophores were chosen to detect A and B in two separate emission channels with sufficient spectral separation. For example, nNOS was labeled with Alexa555-conjugated anti-rabbit IgG antibody, while RyR was labeled with Alexa488-conjugated anti-mouse IgG antibody. The 'Sequential Mode' on the confocal microscope was enabled to excite the two fluorophores separately in order to minimize crosstalk. We used the above method to label the nNOS/RyR pair and the eNOS/RyR pair which were then imaged using confocal microscopy and structured illumination microscopy. The pseudo-color coding of the molecules are the following: red for RyR, green for nNOS, and cyan for eNOS.

The quality of antibody labeling was evaluated by the maintenance of cell morphology (i.e. rod-like, clear striations), brightness of labeling, and uniformity of labeling. For example, in well-preserved and well-labeled cells, the peripheral RyR labeling show clean and smooth outline and the intercalated RyR units are clearly visible; the labeling is bright and uniformly distributed throughout the entire cell [49]. Examples of the cell images are shown in FIG. 17.

Confocal imaging of antibody labeled cells. Confocal images were obtained using an Olympus FlowView 1000 Confocal Microscope (inverted configuration) with a water immersion fluorescence objective UPlanSApo 60X, NA1.2, corrected for the thickness of the No. 1 glass coverslip that is used at the bottom of the perfusion chamber. Water immersion objective was used to match the refractive index of the solution in which the cells are kept atop a No. 1 glass cover slip at the bottom of a containing chamber, so to minimize spherical aberration. The confocal images were acquired using 2D scan. The confocal aperture (CA) was set to 1 Airy unit to obtain the thinnest optical sectioning for highest spatial resolution.

For imaging dual labeled cells, the "Sequential Mode" was used to switch between the two excitation beams, for example 488 nm and 543 nm per line-scan in order to minimize crosstalk between the spectra of the two different fluorophores. The emitted fluorescence lights were separated by dichroic mirror into two channels and passed through corresponding bandpass filters (BA505-525 for green and BA560-660 for red colors), and then collected with a PMT in each channel. The PMT voltage, gain, and offset were set to avoid any saturation and to obtain high fidelity images. The spatial resolution of the images were defined by the highest confocal resolution, normally with the x,y-resolution of ~0.3 μm and z-resolution of 0.8-1.0 μm.

Super-resolution imaging using structured illumination microscopy (SIM). SIM was use to achieve super-resolution imaging with spatial resolution of x,y~100 nm and z~250 nm. Co-localization of nNOS-RYR and eNOS-RyR is measured using the Pearson's co-localization analysis (42); the nearest-neighbor distance is calculated from the smallest pairwise distance between the center of mass of the respective molecular clusters (43). We used a DeltaVision OMX V3.0 Blaze system (Applied Precision Inc, a GE Healthcare Company, Issaquah, Wash.) to acquire the fluorescence images of antibody labeled myocytes. The detailed SIM imaging procedure has been previously described [40]. Briefly the system uses 488 and 532 nm lasers as the light source for illumination. A grating in the beam path is used to generate three coherent beams that create three dimensional structured illumination patterns in the sample. The antibodies labeled cells were immersed in the antifade reagent ProLong Gold with 1.47 RI, and placed on the sample stage. Fluorescence emission is collected with a 60X, 1.42NA objective immersed in oil with 1.514 RI. Fluorescence of different colors are separated by a dichroic mirror and filtered by bandpass emission filters before being collected by two fast sCMOS cameras (PCO-TECH Inc., Romulus, Mich.). To acquire 3D images, the sample is moved along the z-direction at a step size of 125 nm. For each slice, the illumination pattern is rotated three times and shifted five times, resulting in a total of 15 exposures per channel. Acquired raw images were processed with a proprietary software package (SoftWoRx v5.0, Applied Precision Inc.) to reconstruct super-resolution 3D images. Reconstructed images of different colors are then registered using custom-built software to correct chromatic aberrations and image distortions. Prior to experiment, the system and the color registration software had been calibrated using multicolor polymeric beads of 0.1 micron (tetra-spectra beads, Molecular Probes, Eugene, Oreg.). The spatial resolution of the system is found to be ~110 nm for x-, y- and ~250 nm for z-axis. The color registration error is found smaller than a pixel, i.e., 40 nm. 3D rendering of the SIM images was performed with Volocity plus Visualization package.

The colocalization of nNOS-RYR pair and eNOS-RyR pair were analyzed using a software package Volocity with Quantitation (Perking Elmer, Waltham, Mass.), implementing the standard Pearson's colocalization analysis [39]. By following the procedure described previously [40], a user-defined threshold was carefully set to separate signal from background and Manders overlapping coefficients (M1 and M2) were calculated. M1 and M2 were used as index of the extent of colocalization, as shown in FIG. 17D (bars at the left). The bars represent the voxel volume of nNOS(green)-RyR(red) pair, and eNOS(cyan)-RyR(red) pair, each normalized to the RyR voxel volume. The M1 and M2 values were depicted by the overlapping regions (mixed color) in the bars. For example, M1=0.349 and M2=0.524 for nNOS (green)-RyR(red) pair. This is seen as the green and red mixing region occupies 34.9% of the nNOS bar (green) and 52.4% of the RyR bar (red) in the leftmost bar column in FIG. 17D. Note that the above indexes give a somewhat general evaluation for the extent of colocalization. They do not quantify the distances between different molecules.

The nearest-neighbor distance between NOS isoform clusters and RyR clusters is defined to be the smallest pairwise distance between the center of mass of the respective clusters. Objects (blobs) having a volume smaller than 0.00189 (which might arise from photon noise) were excluded in the pairwise distance calculations. The center of mass and the nearest-neighbor distances were determined using the Volocity with Quantitation software package. The probability density function (PDF) for the nearest-neighbor distances between nNOS-RYR pair and between eNOS-RyR pair are shown in FIG. 17D (the curves at the right). The peak nearest-neighbor distances between nNOS-RYR and eNOS-RyR are 0.19 μm and 0.37 μm, respectively.

Previously, nNOS was found to be associated with various molecules at different subcellular locales, including SERCA in the SR membrane [50], PMCA in the caveolae [19], and dystrophin near the sarcolemma and t-tubules [46]. Our SIM imaging data (FIG. 15G) also show more than one population of nNOS-RyR distance (indicated by a kink in the histogram); the first peak occurs at 0.19 μm and this puts a subpopulation of nNOS in the close proximity to RyR.

In Vitro CaMKII activity measurements with Camui sensor. Design and synthesis of the wild-type, phosphorylation resistant, and oxidation resistant Camui constructs were previously described [51]. HEK293 cells were cultured in Eagle's medium plus 5% fetal bovine serum and penicillin/streptomycin for 24 hour and then transfected with plasmids encoding Camui (or a mutant isoform) using a mammalian transfection kit (Stratagene). After an additional 24 hour, Camui expression was checked by fluorescence microscopy. HEK cells expressing Camui were lysed in $Ca^{2+}$-free buffer containing 50 mM Tris-HCl buffer (pH 7.5), 5 mM MgCl2, and protease inhibitors. Fluorescence measurements were performed using a MS SpectraMax plate reading spectrophotometer (Molecular Devices) with excitation and emission slits set to 4 nm, excitation wavelength set to 440 nm, emission wavelengths set to 477 nm (FCFP) and 527 nm (FYFP), respectively. The cytosolic fraction of the transfected HEK cells was diluted in Camui fluorescence was measured in the presence of 10 μM CaM and 200 μM $Ca^{2+}$. EGTA 1 mM was used to chelate $Ca^{2+}$ and autonomous CaMKII activity was measured in the presence of 1 mM EGTA and either 50 μM or 500 μM SNAP.

Figure 18:
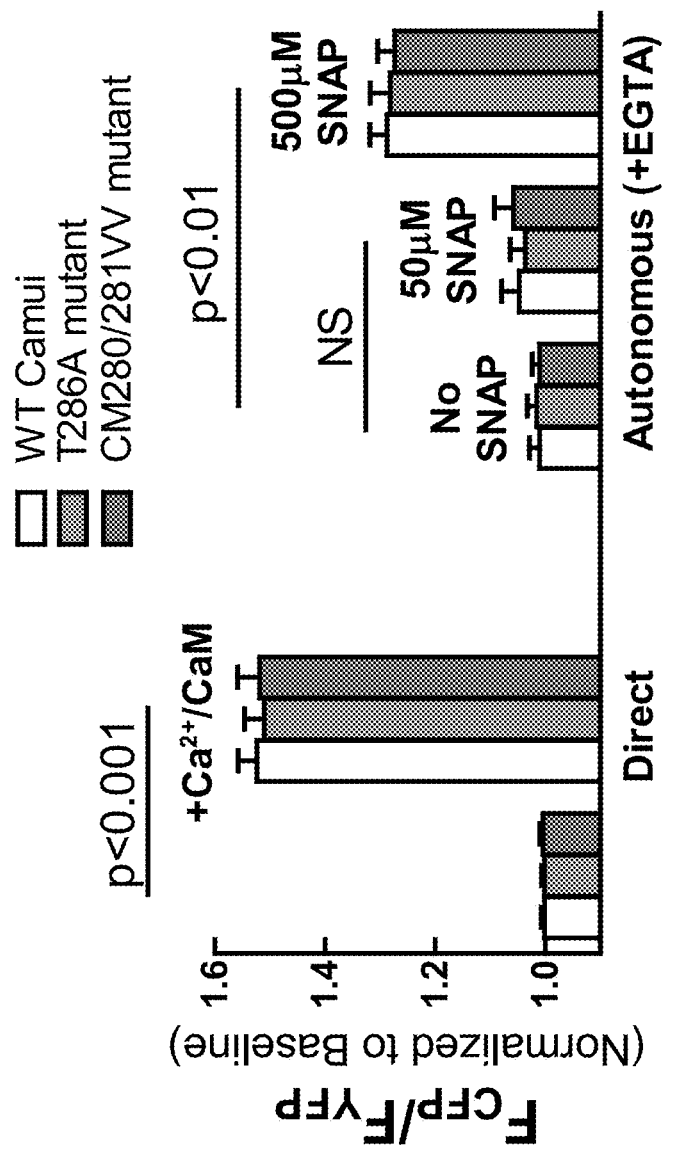
FIG. 18 illustrates NO-dependent CaMKII activation. FRET measurements using the Camui sensor show direct activation of wild-type, non-auto-phosphorylatable (T286A), and non-oxidizable (CM280/281VV) mutant CaMKII by $Ca^{2+}$/CaM (two sets of bars at the left). When $Ca^{2+}$ is buffered by +EGTA, the activation of CaMKII drops (bars labeled No SNAP). Autonomous CaMKII activation was seen with increasing [SNAP] to 500 µM but not 50 µM. Notably, the SNAP/NO-dependent autonomous activation is not secondary to either phosphorylation (T286A) or oxidation (CM/VV), consistent with a direct NO effect. n=6 samples in each bar. One-way ANOVA with Bonferroni post-test was used for pair-wise comparison; p value shows the significance of difference between each pair (same color) under different conditions.

CaMKII activity was known to be increased by autophosphorylation [52] and by oxidation [53]. Here we measure the effect of nitric oxide (NO) on CaMKII activity using the FRET-based biosensor Camui which detects conformational changes in CaMKII during activation. To determine whether NO can activate CaMKII, we expressed the CaMKII activity sensor Camui [51] in HEK cells and measured autonomous activation induced by the NO donor SNAP. Camui comprises of full length CaMKII with a CFP/YFP pair on either end of the kinase, which produce substantial FRET in the closed (autoinhibited) state. If autoinhibition is disrupted, either directly by $Ca^{2+}$/CaM binding or autonomously by post-translational modification of the kinase, FRET is reduced, resulting in an increase in FCFP/FYFP. As shown in FIG. 18, we found no effect on FCFP/FYFP in HEK cell lysates treated with EGTA and 50 μM SNAP (compared to lysates treated with EGTA only), but application of 500 μM SNAP resulted in a significant increase in CaMKII activation (to about 50% of $Ca^{2+}$/CaM dependent activity). CaMKII is known to be autonomously activated by T286 phosphorylation [52] and by CM280/281 oxidation [53]. To test whether one or both of these mechanisms were responsible for SNAP-induced CaMKII activation, we repeated the HEK cell experiment using mutant versions of Camui lacking either the phosphorylation (T286) or oxidation (CM280/281) target sites. In both cases, SNAP dependent activation of CaMKII was preserved. Taken together, our data indicate that CaMKII is subject to NO-induced activation, and that this activation occurs through a mechanism that is independent of previously described phosphorylation and oxidation pathways.

Statistics. The numerical values are calculated for the Mean Value, the Standard Deviation (SD), and the Standard Error of Mean (SEM). Mean± SEM values are shown in the bar charts. Mean± SD values are reported in text. The number of cells in each group was reported in the figure captions and the cells in each group came from 3-6 individual animals. Given the biological variability among cells, each cell is treated as independent in the statistical tests, although multiple cells may come from one animal. The cells from at least 3 individual animals are pooled in each group.

For the data with a normal distribution, Student's t-test or ANOVA is used to evaluate the statistical difference between data groups. The data shown in the bar charts are Mean± SEM values calculated from a number of cells (N=# of cells are given in the figure captions) under the same condition in each group. The cell-to-cell variability (biological variability) in each group is expected to follow normal distribution. For example, the spark rate of each cell was calculated from the number of sparks per 100 μm per second in the confocal linescan image (100 μm*s as a unit area in the image, see FIG. 11G); such numerical spark rate data from 18 cells in the load-free group were then calculated for the Mean, SD, SEM values. Student's t-test (unpaired with unequal variance) is used to evaluate the difference in the mean values of two different groups. The difference is deemed significant if $p<0.05$, and denoted *$p<0.05$, $p<0.01$, $p<0.001$* by the convention in the field. One-way ANOVA is used to compare more than two groups and Bonferroni post-test is then used for pair-wise comparisons. Two-way ANOVA test is used to compare multiple groups with two distinct factors. For example, in FIGS. 19A and 19B, the $Ca^{2+}$ spark rate was compared between two different mouse strains (R92Q versus WT) and also between the drug treated versus untreated groups within the same strain. Hence, two-way ANOVA test is used, which show significant difference in the $Ca^{2+}$ spark rate between the R92Q versus WT strains ($p<0.0001$), significant drug effects ($p<0.0001$) within each strain, and also significant interaction ($p<0.0001$). Bonferroni post-test was used for pair-wise comparison and show significant difference for the drug effect compared to Cell-in-Gel without drug ($p<0.001$***) on each strain, as well as significantly higher spark rate in R92Q than WT for Cell-in-Gel condition ($p<0.05$#) and for Gp91ds effect ($p<0.001$###).

For the data with a non-normal distribution, Mann-Whitney test is used to compare two groups. For example, in FIG. 15C the intermolecular distance histogram has a non-normal distribution. Therefore, Mann-Whitney test is used to compare the nNOS-RyR distance versus the eNOS-RyR distance histograms, and the difference is found significant with $p<0.0001$. All statistical tests were performed using GraphPad PRISM software (http://www.graphpad.com/, USA).

Results

Cell-in-Gel System to Impose Mechanical Load During Single Myocyte Contraction

Previously, investigations on mechano-chemo-transduction mechanisms had been limited by difficulties in controlling the mechanical load on myocyte contraction at the single cell level. We developed a novel 'Cell-in-Gel' system by embedding freshly isolated myocytes in a 3D elastic matrix made of polyvinyl alcohol hydrogel and boronic acid crosslinker; the boronate group also crosslinks the cell-surface glycans and thereby tethering the cell surface to the gel (FIG. 11A, FIG. 20) (12). When the myocyte in-gel contracts against the gel matrix, the elastic matrix resists the shortening and broadening of the cell during contraction and the converse during relaxation (FIG. 11B). Control experiments demonstrate that the gel components are non-toxic and do not affect the cell function (FIG. 12). This Cell-in-Gel system mimics the in vivo mechanical environment in two important aspects: one is to impose multi-axial 3D mechanical stress during contraction; another is to tether the cell surface to the gel to impose both normal and shear stresses to the cell surface. (13)

Afterload-induced Changes in $Ca^{2+}$ Handling During Systole and Diastole

We studied the mechanical stress effects during myocyte contraction under mechanical afterload using the Cell-in- Gel system. The myocyte was paced at 0.5 Hz to reach steady state contraction while continuously perfused with Tyrode solution. Compared to load-free contractions (FIG. 11C), the myocyte contracting in-Gel (FIG. 11D) displayed less fractional shortening (FIG. 11E); it also showed augmented $Ca^{2+}$ transient in systole (FIG. 11F) as well as spontaneous $Ca^{2+}$ sparks during diastole (FIG. 11G). The $Ca^{2+}$ spark rate (sparks per unit area) is low under load-free condition, slightly increased in soft gel (Gel5%), and significantly increased in stiffer gel (Gel7.5%); using blebbistatin to decouple contraction restored the $Ca^{2+}$ transient and spark rate to the load-free condition (FIG. 11G), demonstrating a positive correlation between the mechanical load and the spontaneous $Ca^{2+}$ spark generation. Therefore, afterload on the myocyte during contraction increases the systolic $Ca^{2+}$ transient which enhances contractility to counter mechanical load, but also leads to spontaneous $Ca^{2+}$ sparks during diastole which may lead to arrhythmogenic activities. In all experiments below, we used the Cell-in-Gel system with Gel7.5% to impose mechanical afterload during myocyte contraction.

The temporal response (FIG. 14A, 14B) shows that during the initial several beats of contraction, diastolic $Ca^{2+}$ sparks are few, but then arise prominently during subsequent beats. Upon cessation of pacing, the sparks disappear almost immediately. The initial latency indicates a build-up process for mechano-chemo-transduction to activate the signaling pathways that lead to RyR modulation and increased $Ca^{2+}$ sparks. Such latency agrees with a slow onset of the Anrep effect that takes minutes to develop fully at the tissue level (3). The fact that the $Ca^{2+}$ sparks disappeared immediately after cessation of pacing is also consistent with a reversible NO signaling effect (14, 15).

To test whether the increase of $Ca^{2+}$ transient and $Ca^{2+}$ spark rate could be due to elevated sarcoplasmic reticulum (SR) $Ca^{2+}$ content, we measured the cytosolic $Ca^{2+}$ concentration and SR content using the Fura-2 ratiometric method. As shown in FIG. 14C, the myocyte was paced at 0.5 Hz; after reaching reach steady state, pacing was stopped and 15 second later caffeine was rapidly applied to release the SR $Ca^{2+}$ content. Although the systolic $Ca^{2+}$ transient was increased in the myocyte contracting in-Gel versus load-free (FIG. 14D), the SR $Ca^{2+}$ content did not show detectable change (FIG. 14E). Thus, the fractional SR $Ca^{2+}$ release is higher for the myocytes contracting in-Gel (Peak $Ca^{2+}$ transient to SR content ratio: 85±6% in-Gel versus 77±7% load-free), demonstrating an increase of RyR sensitivity. Increased RyR sensitivity can also explain the increase of diastolic $Ca^{2+}$ sparks. High RyR sensitivity and diastolic SR $Ca^{2+}$ leak would reduce SR $Ca^{2+}$ content (16) unless it was compensated by enhanced SR $Ca^{2+}$ uptake via SERCA or reduced $Ca^{2+}$ removal via Na+/$Ca^{2+}$ exchanger. Indeed, the systolic $Ca^{2+}$ transient decline was unaltered (FIG. 14F, FIG. 16B) which indicates that SR $Ca^{2+}$ uptake remains able to reduce $(Ca^{2+})i$ despite greater release. Moreover, the myocyte in-Gel showed slower decline of the caffeine-induced $Ca^{2+}$ transient (FIG. 14G), indicating reduced $Ca^{2+}$ removal flux through Na+/$Ca^{2+}$ exchange and sarcolemma $Ca^{2+}$ pump. The above concomitant changes allow the myocyte to maintain normal SR $Ca^{2+}$ content despite the increased SR $Ca^{2+}$ release.

Localized nNOS and eNOS Signaling in Mechano-chemo-transduction

To decipher the mechano-chemo-transduction mechanisms that mediate afterload-induced changes in $Ca^{2+}$ handling, we examined the involvement of nitric oxide signaling. Myocytes were paced at 0.5 Hz until contraction reached steady-state. Myocytes in-Gel displayed high spontaneous $Ca^{2+}$ spark rate (FIG. 15A). L-NAME, which inhibits all NOS isoforms, effectively suppressed $Ca^{2+}$ sparks (FIG. 15B), indicating that NOS signaling is essential for mechano-chemo-transduction. Next, we distinguished between the neuronal isoform (nNOS or NOS1) and the endothelial isoform (eNOS or NOS3) of NOS that are constitutively expressed in ventricular myocytes (17). To our surprise, selective inhibition of eNOS using L-Nio-dihydrochloride (L-Nio) failed to suppress $Ca^{2+}$ sparks (FIG. 15A, 15B). However, selective inhibition of nNOS using Nw-Propyl-L-arginine hydrochloride (L-NPA) effectively suppressed $Ca^{2+}$ sparks (FIG. 15A, 15B). These data are consistent with the conclusion that nNOS, but not eNOS, mediates afterload-induced spontaneous $Ca^{2+}$ sparks. To rule out possible non-specific effects of pharmacological inhibitors, we also conducted experiments using genetic knockout nNOS−/− and eNOS−/− mice. The nNOS−/− myocytes showed very few afterload-induced $Ca^{2+}$ sparks (FIG. 15A, 15C). In contrast, eNOS−/− myocytes exhibited high $Ca^{2+}$ spark rate during contraction in-Gel (FIG. 15A, 15D); inhibiting nNOS in the eNOS−/− myocyte effectively suppressed $Ca^{2+}$ sparks (FIG. 15A, 15D). Therefore nNOS, but not eNOS, mediates the afterload-induced spontaneous SR $Ca^{2+}$ release.

A plausible explanation for the selective effect of nNOS versus eNOS on $Ca^{2+}$ sparks is the proximity of nNOS to RyR, as NO is known to be a short-lived local signaling molecule. In cardiac myocytes, eNOS was reportedly in caveolae (18) while nNOS was localized at the SR (19) and also sarcolemma (20). However, the intermolecular distance of RyR to nNOS versus eNOS had not been measured. Since confocal resolution is not enough to resolve these distances (FIG. 17A), we used super-resolution structured illumination microscopy (SIM) to quantify the colocalization of nNOS-RyR versus eNOS-RyR. SIM images show that nNOS is closely colocalized with RyR (FIG. 17B), whereas eNOS is located farther from RyR (FIG. 15F). Colocalization analyses yield an overlap coefficient of 0.438 for nNOS-RyR and 0.125 for eNOS-RyR (FIG. 17C). Nearest neighbor distance histogram (FIG. 17D) also show significantly different patterns with nNOS-RyR distance peaking at 0.19 μm and eNOS-RyR distance at 0.37 μm, a two-fold difference. The effective NO signaling range should be influenced by the distance of diffusion, the amount of NO produced by NOS, the degradation/removal and buffering capacity, and the target modification kinetics. The 2-fold change in signaling distance would translate to 4-fold slower diffusion time and 8-fold decrease in NO concentration at the target site. The above structural data combined with the functional data consistent with the conclusion that the effective range of nNOS versus eNOS signaling is highly localized in sub-micron domains in cardiac myocytes.

Mechano-chemo-transduction in Healthy Heart and in Cardiomyopathy

To further explore the relationship between mechanical stress and $Ca^{2+}$ dynamics, we also studied a Familial Hypertrophic Cardiomyopathy model with R92Q mutation in troponin T. The R92Q mutation in human or mouse heart causes increased myofilament $Ca^{2+}$ sensitivity and exhibit arrhythmias and sudden cardiac death (21) (22) (23) (24) (25). A major unresolved question is how mutations in contractile proteins lead to arrhythmias (26) (27). Hence we investigated the mechano-chemo-transduction in R92Q myocytes. The afterload-induced spontaneous $Ca^{2+}$ spark rate is significantly higher in R92 myocytes (FIG. 19A, 19B) than wild-type myocytes (FIG. 19B). Consistently, the sparks are suppressed by inhibiting nNOS but not eNOS (FIG. 19A, 19B). Our data are consistent with the conclusion that increased sensitivity of mechano-chemo-transduction that lead to increased spontaneous $Ca^{2+}$ activities, and thus provide a mechanistic explanation for $Ca^{2+}$ induced arrhythmogenesis in the R92Q FHC heart (28-31).

To extend the signaling analysis, we tested whether NOX2-ROS signaling, which is activated by preload (8), might also be engaged by afterload. FIG. 19B shows that using gp91ds-tat to inhibit NOX2 reduced afterload-induced $Ca^{2+}$ sparks in the wild-type but not R92Q myocytes; this shows a complex involvement of NOX2. Since NOX2 was found to be activated by nNOS signaling (32), a complex interplay between the two is expected. CaMKII is activated by ROS (53), and we show it also activated by NO signaling (FIG. 18); CaMKII can then phosphorylate RyR to stimulate $Ca^{2+}$ sparks (33). Indeed, we found that CaMKII inhibition prevented the afterload-induced increase in $Ca^{2+}$ sparks in both WT and R92Q mice (FIG. 19B).

Discussion

In summary, using the present Cell-in-Gel system we have identified key molecules involved in mechano-chemo-transduction that respond to the mechanical load during myocyte contraction to cause changes in $Ca^{2+}$ handling. The systolic $Ca^{2+}$ transient is increased by afterload, which may well contribute mechanistically to the Anrep effect (3, 4, 34, 35). The afterload-induced spontaneous $Ca^{2+}$ sparks are suppressed by inhibiting nNOS, but not eNOS, although both NOS isoforms are involved in increasing the $Ca^{2+}$ transient. The divergent effects of nNOS versus eNOS on modulating RyR may be explained by highly localized NO signaling; the data from super-resolution imaging are consistent with the conclusion that the intracrine NO signaling to be within sub-micron range in the myocytes. In addition to NOS, NOX2 and CaMKII were found to be involved in the enhanced SR $Ca^{2+}$ release triggered by mechanical afterload during myocyte contraction. The present study of afterload effects complements previous studies of the preload effects where nNOS was not involved and CaMKII was not studied (6, 8). Furthermore, we found that selective inhibition of nNOS and CaMKII can effectively suppress afterload-induced spontaneous $Ca^{2+}$ activities in a familiar hypertrophic cardiomyopathy model which is known to suffer high incidence of cardiac arrhythmias (25) (36) (37). Hence the mechano-NOS-CaMKII pathways we describe here provide fundamental mechanistic working model (FIG. 19C), in addition to other known pathways involving NOX (8), angiotensin II (38), transient receptor potential canonical channels (39) and more (review by (4)), for understanding the Anrep effect. The mechano-chemo-transduction through NOS and CaMKII signaling pathways provide therapeutic insights on treating mechanical stress induced $Ca^{2+}$ dysregulation, arrhythmias, and cardiomyopathy.

REFERENCES FOR EXAMPLE 7

1 von Anrep, G. (1912) On the part played by the suprarenals in the normal vascular reactions of the body. J. Physiol. 45, 307-317
2 Sarnoff, S. J., Mitchell, J. H., Gilmore, J. P. and Remensnyder, J. P. (1960) Homeometric autoregulation in the heart. Circ. Res. 8, 1077-1091
3 Nichols, C. G., Hanck, D. A. and Jewell, B. R. (1988) The Anrep effect: an intrinsic myocardial mechanism. Can J Physiol Pharmacol. 66, 924-929
4 Cingolani, H. E., Perez, N. G., Cingolani, O. H. and Ennis, I. L. (2013) The Anrep effect: 100 years later. American Journal of Physiology—Heart and Circulatory Physiology. 304, H175-H182
5 ter Keurs, H. E. D. J. (1996) Heart failure and Starling's law of the heart. Can. J. Cardiol. 12, 1047-1057
6 Petroff, M. G., Kim, S. H., Pepe, S., Dessy, C., Marban, E., Balligand, J. L. and Sollott, S. J. (2001) Endogenous nitric oxide mechanisms mediate the stretch dependence of $Ca^{2+}$ release in cardiomyocytes. Nat Cell Biol. 3, 867-873
7 Prosser, B. L., Ward, C. W. and Lederer, W. J. (2010) Subcellular $Ca^{2+}$ signaling in the heart: the role of ryanodine receptor sensitivity. The Journal of General Physiology. 136, 135-142
8 Prosser, B. L., Ward, C. W. and Lederer, W. J. (2011) X-ROS Signaling: Rapid Mechano-Chemo Transduction in Heart. Science. 333, 1440-1445
9 Chirinos, J. A. and Segers, P. (2010) Noninvasive Evaluation of Left Ventricular Afterload. Hypertension. 56, 563-570
10 Toischer, K., Rokita, A. G., Unsold, B., Zhu, W., Kararigas, G., Sossalla, S., Reuter, S. P., Becker, A., Teucher, N., Seidler, T., Grebe, C., Preub, L., Gupta, S. N., Schmidt, K., Lehnart, S. E., Kruger, M., Linke, W. A., Backs, J., Regitz-Zagrosek, V., Schafer, K., Field, L. J., Maier, L. S. and Hasenfuss, G. (2010) Differential Cardiac Remodeling in Preload Versus Afterload. Circulation. 122, 993-1003
11 Shin, S.-H., Hung, C.-L., Uno, H., Hassanein, A. H., Verma, A., Bourgoun, M., Kober, L., Ghali, J. K., Velazquez, E. J., Califf, R. M., Pfeffer, M. A., Solomon, S. D. and Investigators, f. t. V. i. A. M. I. T. (2010) Mechanical Dyssynchrony After Myocardial Infarction in Patients With Left Ventricular Dysfunction, Heart Failure, or Both. Circulation. 121, 1096-1103
12 Onofiok E, Lam K S, Luo J. Three dimensional cell adhesion matrix. International Patent # WO/2010/148346 (2010).
13 Shaw, J., Izu, L. and Chen-Izu, Y. (2013) Mechanical Analysis of Single Myocyte Contraction in a 3-D Elastic Matrix. PLoS ONE. 8, e75492
14 Stoyanovsky, D., Murphy, T., Anno, P. R., Kim, Y.-M. and Salama, G. (1997) Nitric oxide activates skeletal and cardiac ryanodine receptors. Cell Calcium. 21, 19-29
15 Lim, G., Venetucci, L., Eisner, D. A. and Casadei, B. (2008) Does nitric oxide modulate cardiac ryanodine receptor function? Implications for excitation-contraction coupling. Cardiovascular Research. 77, 256-264
16 Eisner, D. A., Choi, H. S., Diaz, M. E., O'Neill, S. C. and Trafford, A. W. (2000) Integrative analysis of calcium cycling in cardiac muscle. Circ Res. 87, 1087-1094
17 Barouch, L. A., Harrison, R. W., Skaf, M. W., Rosas, G. O., Cappola, T. P., Kobeissi, Z. A., Hobai, I. A., Lemmon, C. A., Burnett, A. L., O'Rourke, B., Rodriguez, E. R., Huang, P. L., Lima, J. A. C., Berkowitz, D. E. and Hare, J. M. (2002) Nitric oxide regulates the heart by spatial confinement of nitric oxide synthase isoforms. Nature. 416, 337-339
18 Feron, O., Belhassen, L., Kobzik, L., Smith, T. W., Kelly, R. A. and Michel, T. (1996) Endothelial Nitric Oxide Synthase Targeting to Caveolae: SPECIFIC INTERACTIONS WITH CAVEOLIN ISOFORMS IN CARDIAC MYOCYTES AND ENDOTHELIAL CELLS. Journal of Biological Chemistry. 271, 22810-22814
19 Williams, J. C., Armesilla, A. L., Mohamed, T. M. A., Hagarty, C. L., McIntyre, F. H., Schomburg, S., Zaki, A. O., Oceandy, D., Cartwright, E. J., Buch, M. H., Emerson, M. and Neyses, L. (2006) The Sarcolemmal Calcium Pump, α-1 Syntrophin, and Neuronal Nitric-oxide Synthase Are Parts of a Macromolecular Protein Complex. Journal of Biological Chemistry. 281, 23341-23348

20 Mohamed, T. M. A., Oceandy, D., Zi, M., Prehar, S., Alatwi, N., Wang, Y., Shaheen, M. A., Abou-Leisa, R., Schelcher, C., Hegab, Z., Baudoin, F., Emerson, M., Mamas, M., Di Benedetto, G., Zaccolo, M., Lei, M., Cartwright, E. J. and Neyses, L. (2011) Plasma Membrane Calcium Pump (PMCA4)-Neuronal Nitric-oxide Synthase Complex Regulates Cardiac Contractility through Modulation of a Compartmentalized Cyclic Nucleotide Microdomain. Journal of Biological Chemistry. 286, 41520-41529

21 Szczesna, D., Zhang, R., Zhao, J., Jones, M., Guzman, G. and Potter, J. D. (2000) Altered regulation of cardiac muscle contraction by troponin T mutations that cause familial hypertrophic cardiomyopathy. J Biol Chem. 275, 624-630

22 Chandra, M., Rundell, V. L. M., Tardiff, J. C., Leinwand, L. A., de Tombe, P. P. and Solaro, R. J. (2001) $Ca^{2+}$ activation of myofilaments from transgenic mouse hearts expressing R92Q mutant cardiac troponin T. AJP—Heart and Circulatory Physiology. 280, H705-H713

23 Yanaga, F., Morimoto, S. and Ohtsuki, I. (1999) $Ca^{2+}$ sensitization and potentiation of the maximum level of myofibrillar ATPase activity caused by mutations of troponin T found in familial hypertrophic cardiomyopathy. J Biol Chem. 274, 8806-8812

24 Morimoto, S., Yanaga, F., Minakami, R. and Ohtsuki, I. (1998) $Ca^{2+}$-sensitizing effects of the mutations at Ile-79 and Arg-92 of troponin T in hypertrophic cardiomyopathy. Am J Physiol. 275, C200-207

25 Watkins, H., McKenna, W. J., Thierfelder, L., Suk, H. J., Anan, R., O'Donoghue, A., Spirito, P., Matsumori, A., Moravec, C. S., Seidman, J. G. and et al. (1995) Mutations in the genes for cardiac troponin T and alpha-tropomyosin in hypertrophic cardiomyopathy. N Engl J Med. 332, 1058-1064

26 Hernandez, O. M., Housmans, P. R. and Potter, J. D. (2001) Plasticity in Skeletal, Cardiac, and Smooth Muscle: Invited Review: Pathophysiology of cardiac muscle contraction and relaxation as a result of alterations in thin filament regulation. Journal of Applied Physiology. 90, 1125-1136

27 Tardiff, J. C. (2005) Sarcomeric proteins and familial hypertrophic cardiomyopathy: linking mutations in structural proteins to complex cardiovascular phenotypes. Heart Fail Rev. 10, 237-248

28 Boyden, P. A., Barbhaiya, C., Lee, T. and ter Keurs, H. E. (2003) Nonuniform $Ca^{2+}$ transients in arrhythmogenic Purkinje cells that survive in the infarcted canine heart. Cardiovasc Res. 57, 681-693

29 Berlin, J. R., Cannell, M. B. and Lederer, W. J. (1989) Cellular origins of the transient inward current in cardiac myocytes. Role of fluctuations and waves of elevated intracellular calcium. Circ Res. 65 115-126

30 Kass, R. S., Lederer, W. J., Tsien, R. W. and Weingart, R. (1978) Role of calcium ions in transient inward currents and aftercontractions induced by strophanthidin in cardiac Purkinje fibres. J Physiol. 281, 187-208

31 Ferrier, G. R. and Moe, G. K. (1973) Effect of calcium on acetylstrophanthidin-induced transient depolarizations in canine Purkinje tissue. Circ Res. 33, 508-515

32 Girouard, H., Wang, G., Gallo, E. F., Anrather, J., Zhou, P., Pickel, V. M. and Iadecola, C. (2009) NMDA receptor activation increases free radical production through nitric oxide and NOX2. J Neurosci. 29, 2545-2552

33 Guo, T., Zhang, T., Mestril, R. and Bers, D. M. (2006) $Ca^{2+}$/Calmodulin-Dependent Protein Kinase II Phosphorylation of Ryanodine Receptor Does Affect Calcium Sparks in Mouse Ventricular Myocytes. Circ Res. 99, 398-406

34 Kentish, J. C. and Wrzosek, A. (1998) Changes in force and cytosolic $Ca^{2+}$ concentration after length changes in isolated rat ventricular trabeculae. J Physiol. 506 (Pt 2), 431-444

35 Alvarez, B. V., Perez, N. G., Ennis, I. L., Camilion de Hurtado, M. C. and Cingolani, H. E. (1999) Mechanisms underlying the increase in force and $Ca(^{2+})$ transient that follow stretch of cardiac muscle: a possible explanation of the Anrep effect. Circ Res. 85, 716-722

36 Moolman, J. C., Corfield, V. A., Posen, B., Ngumbela, K., Seidman, C., Brink, P. A. and Watkins, H. (1997) Sudden death due to troponin T mutations. J Am Coll Cardiol. 29, 549-555

37 Maron, B. J., Gardin, J. M., Flack, J. M., Gidding, S. S., Kurosaki, T. T. and Bild, D. E. (1995) Prevalence of hypertrophic cardiomyopathy in a general population of young adults. Echocardiographic analysis of 4111 subjects in the CARDIA Study. Coronary Artery Risk Development in (Young) Adults. Circulation. 92, 785-789

38 Kockskamper, J., von Lewinski, D., Khafaga, M., Elgner, A., Grimm, M., Eschenhagen, T., Gottlieb, P. A., Sachs, F. and Pieske, B. (2008) The slow force response to stretch in atrial and ventricular myocardium from human heart: Functional relevance and subcellular mechanisms. Progress in Biophysics and Molecular Biology. 97, 250-267

39 Seo, K., Rainer, P. P., Lee, D. I., Hao, S., Bedja, D., Birnbaumer, L., Cingolani, O. H. and Kass, D. A. (2014) Hyperactive Adverse Mechanical-Stress Responses in Dystrophic Heart are Coupled to TRPC6 and Blocked by cGMP-PKG Modulation. Circulation Research 40 Chen-Izu, Y., Chen, L., Banyasz, T., McCulle, S. L., Norton, B., Scharf, S. M., Agarwal, A., Patwardhan, A. R., Izu, L. T. and Balke, C. W. (2007) Hypertension-induced remodeling of cardiac excitation-contraction coupling in ventricular myocytes occurs prior to hypertrophy development. Am J Physiol Heart Circ Physiol. 293, H3301-3310

41 Kirk, M. M., Izu, L. T., Chen-Izu, Y., McCulle, S. L., Wier, W. G., Balke, C. W. and Shorofsky, S. R. (2003) Role of the transverse-axial tubule system in generating calcium sparks and calcium transients in rat atrial myocytes. The Journal of Physiology Online. 547, 441-451

42 Barlow, A. L., Macleod, A., Noppen, S., Sanderson, J. and Guerin, C. J. (2010) Colocalization analysis in fluorescence micrographs: verification of a more accurate calculation of pearson's correlation coefficient. Microscopy and microanalysis: the official journal of Microscopy Society of America, Microbeam Analysis Society, Microscopical Society of Canada. 16, 710-724

43 Zhang, T., Osborn, S., Brandow, C., Dwyre, D., Green, R., Lane, S. and Wachsmann-Hogiu, S. (2013) Structured illumination-based super-resolution optical microscopy for hemato- and cyto-pathology applications. Analytical Cellular Pathology. 36, 27-35

Example 8

Defective Mechano-chemo-transduction in Heart Disease Models Revealed by Cell-in-Gel Experiments In this example, we systematically investigate the chain-of-command in DGC by disrupting mechano-transduction at dystroglycan (by untethering it from the gel matrix) and at dystrophin (using mdx mouse model) sites. The outcome elucidates how DGC links mechanical stress to modulate $Ca^{2+}$ handling pathways in cardiomyocytes. We used our 'Cell-in-Gel' technology to studying how Duchenne muscular dystrophy (DMD) mutations may cause cardiac dysregulation at the single cell and molecular levels. We discovered that during cardiac muscle contraction, mechanical stress on the cell is transduced to biochemical signals inside the cell. This mechano-chemo-transduction process is carried out by the dystrophin-glycoprotein complex. Importantly, DMD patients have mutations in this macromolecular complex, which disrupts mechano-chemo-transduction to cause $Ca^{2+}$ dysregulation and cardiac dysfunction. In this example, we used our Cell-in-Gel system to further investigate how various DMD mutations disrupt mechano-chemo-transduction process, what are the key molecules involved in causing cardiac dysfunction, and to test a new drug target.

Defective DGC disrupts M-C transduction. To study the role of DGC as an M-C transduction complex, we disrupted mechanical link at various sites in DGC macromolecular complex (FIG. 21). Our gel chemistry tethers cell-surface glycans to the gel matrix (by boronate binding to cis-diols). Hence dystroglycan (DG) is tethered to the gel and subject to mechanical stress during myocyte contraction. To prevent α-DG from tethering, we pre-treated cells with α-DG antibody before embedding the cell in the gel. Such 'masking' of α-DG suppressed diastolic $Ca^{2+}$ sparks (FIG. 21B vs. FIG. 21A). This also demonstrated that α-DG is a cell-surface mechanosensor. Next, we studied how defective DGC affects $Ca^{2+}$ signaling using mdx mouse model. (5C) shows that, unlike wild-type (wt) cells, mdx cardiomyocytes contraction in-gel did not generate diastolic $Ca^{2+}$ sparks. These data are consistent with previous findings by us and colleagues that (1) in mdx, dystrophin is missing and nNOS dislocalized in skeletal and cardiac myocytes (Lai, et al., Proceedings of the National Academy of Sciences (2013) 110:525-530; Li, et al., *Journal of Cell Science* (2010) 123:2008-2013; Bia, et al., *Journal of Molecular and Cellular Cardiology* (1999) 31:1857-1862; Wehling-Henricks, et al., Human Molecular Genetics (2005) 14:1921-1933); and (2) nNOS generated NO can increase RyR activity to cause $Ca^{2+}$ sparks (Jian, et al., *Sci Signal*. (2014) Mar. 18; 7(317):ra27). Therefore, our data are consistent with the conclusion that breaking the chain of command at α-DG or at dystrophin point can disconnect mechano-chemo-transduction from DGC to NOS signaling and to $Ca^{2+}$ handling system.

Investigate specific MCT complex by selectively tethering cell-surface mechanosensors. In one feature of our Cell-in-Gel system, avidin is engineered into the gel polymer to 'hook' on biotin-conjugated molecules. This enabled tethering specific cell-surface molecules to the gel matrix. In Jian, et al., supra, dystroglycans were bound to the gel by boronate-PEG crosslinker, which transduce mechanical stress through DGC to generate $Ca^{2+}$ sparks in wild-type cardiomyocytes (FIG. 22A). However, in dystrophin-null mdx mouse cardiomyocytes, missing dystrophin and nNOS broke the chain-of-command in mechano-chemo-transduction; hence it decoupled mechanical stress from generating $Ca^{2+}$ sparks (FIG. 22B).

Next, we tethered both dystroglycans and integrins to the gel by using PVA-avidin gel with a primary antibody against β1-integrin subunit and a biotin-conjugated secondary antibody. Tethering both DGC and VTI to the gel produced drastically different effects than tethering DGC alone. The mechanical stress induced $Ca^{2+}$ sparks increased in wt cardiomyocytes (FIG. 22C). However, the mdx cardiomyocytes are devoid of $Ca^{2+}$ sparks when DGC is tethered (FIG. 22D), but exhibit high frequency of spontaneous $Ca^{2+}$ sparks and waves when both DGC and VTI are tethered (as both are tethered to extracellular matrix in vivo). This is consistent with a vulnerability of mdx to mechanical load (pressure overload). This 'tethering' technique can be used in conjunction with 'masking' to investigate various mechano-chemo-transduction complexes (integrin isoforms, other mechanosensors).

Physiological and pathophysiological implications of DGC being a mechano-chemo-transducer. Our data are consistent with the conclusion that DGC functions as a mechano-chemo-transduction complex in the contractile autoregulatory feedback loop. This can explain why defective DGC in Duchenne muscular dystrophy (DMD) can break the feedback loop leading to impaired contractile autoregulation. At the whole-heart level, impaired autoregulation would manifest itself as poorer regulation of cardiac output in response to changing afterload. In fact, many DMD patients show symptoms consistent with this prediction. For example, echocardiographic measurements show reduced fractional shortening in young DMD patients (Ramaciotti, et al., *J. Child Neurol*. (2002) 17:191-194) and the dystrophin-null mdx mouse is extremely vulnerable to pressure overload (Kamogawa, et al., *Cardiovascular Research* (2001) 50:509-515). Conversely, reducing cardiac workload (ACE inhibitor and β-blocker treatment) aids the heart (Jefferies, et al., *Circulation* (2005) 112:2799-2804). Previous studies also show that mdx cardiomyocytes have delocalized nNOS, unchanged eNOS, and upregulation of iNOS (Bia, et al., *Journal of Molecular and Cellular Cardiology* (1999) 3:1857-1862). Expressing nNOS in mdx mice reduced ECG abnormalities (Wehling-Henricks, et al., Human Molecular Genetics (2005) 14:1921-1933). These data support our new findings on an important role of DGC in M-C transduction.

Previous studies in the muscular dystrophy field mainly focused on the role of DGC as a structural support for membrane integrity, whereas the role of DGC in M-C transaction has not been fully explored and remains unclear. The Cell-in-Gel system provides an enabling tool for investigating the M-C transduction through DGC at both the molecular and cellular levels. Here, our data are demonstrate that DGC transduces mechanical stress to affect NOS signaling which modulates $Ca^{2+}$ dynamics in cardiomyocytes. Identifying the key moleculaes involved will provide fresh drug targets for developing new therapies for treating muscular dystrophy associated cardiomyopathy.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A hydrogel composition comprising a cell encapsulated in a hydrogel, wherein the hydrogel is comprised of:
 a first binding partner of a binding partner pair, wherein the first binding partner is avidin, and wherein the avidin is optionally conjugated to a biocompatible polymer,
 a second binding partner of the binding partner pair, wherein the second binding partner is biotin, which is conjugated to a PEG polymer to form a biotin-PEG-biotin crosslinker,
 wherein the avidin binds with the biotin-PEG-biotin crosslinker to form the hydrogel; and wherein the cell is attached to a biotin-ligand conjugate via the ligand and the resultant biotin-ligand-cell conjugate is bound, via the biotin, to the avidin of the hydrogel, thereby encapsulating the cell in the hydrogel.

2. The composition of claim 1, wherein the avidin is selected from avidin, streptavidin, neutravidin and captavidin.

3. The composition of claim 1, wherein the biocompatible polymer is selected from the group consisting of polyvinyl alcohol (PVA), agarose and alginate.

4. The composition of claim 1, wherein the hydrogel comprises a stiffness or Young's modulus value in the range of about 0.1 kPa to about 100 kPa.

5. The composition of claim 1, wherein the hydrogel is optically transparent.

6. The composition of claim 1, wherein the ligand binds to a cell surface molecule.

7. The composition of claim 6, wherein the surface molecule is selected from the group consisting of an integrin, a glycan, a glycoprotein, and a cell surface receptor.

8. The composition of claim 1, wherein the ligand is selected from a polypeptide, a linear peptide, a circularized peptide, a peptidomimetic, an antigen binding molecule, an antibody and an antibody fragment.

9. The composition of claim 1, wherein the ligand is a polypeptide selected from the group consisting of collagen, laminin, fibronectin, fibrinogen, vitronectin, VCAM-1, cadherin, and subsequences thereof.

10. The composition of claim 1, wherein the cell is a cardiac myocyte, a skeletal muscle myocyte or a smooth muscle myocyte.

11. A system comprising:
   i) one or more perfusion chambers, each perfusion chamber comprising the hydrogel composition of any one of claims 1, 2, 3, 4, 5, 6-9, or 10;
   ii) first and second mounting grips in contact with the hydrogel, wherein the first and second grips introduce tension on the hydrogel composition in at least two dimensions;
   iii) a force transducer connected to the first grip and a tension manipulator connected to the second grip, wherein the force transducer senses mechanical tension imposed on the hydrogel composition which is used to calculate the stress in the cell and the hydrogel composition;
   iv) a computer in communication with the force transducer, wherein the computer stores the resultant mechanical tension readings sensed by the force transducer.

12. A method of producing a composition of claim 1, comprising:
   a) incubating one or more cells with a biotin-ligand conjugate under conditions allowing the ligand to bind to one or more cell surface molecules on the one or more cells;
   b) contacting the cells bound to the biotin-ligand conjugate with avidin and optionally conjugated to a biocompatible polymer under conditions sufficient for avidin to bind the biotin-ligand conjugate; and
   c) contacting the cells from step b) with a biotin-PEG-biotin crosslinker under conditions sufficient to crosslink the avidin, thereby encapsulating the cells in a hydrogel.

13. A kit comprising:
   i) a solution comprising a first binding partner of a binding partner pair, wherein the first binding partner is avidin, and wherein avidin is optionally conjugated to a biocompatible polymer;
   ii) a solution comprising a Y-X-Y crosslinker; wherein X is a PEG polymer and Y is a second binding partner of the binding partner pair, wherein the second binding partner is biotin; and
   iii) a solution of biotin conjugated to a ligand wherein the ligand is capable of binding to a cell.

* * * * *